US012672862B2

(12) United States Patent
Grant et al.

(10) Patent No.: US 12,672,862 B2
(45) Date of Patent: Jul. 7, 2026

(54) IMPLANT FOR VASCULAR CLOSURE

(71) Applicant: Vivasure Medical Limited, Galway (IE)

(72) Inventors: Peter Grant, Galway (IE); Mark McGoldrick, Athlone (IE); Christopher Martin, Oughterard (IE); Gerard Brett, Claregalway (IE)

(73) Assignee: Vivasure Medical Limited, Galway (IE)

(*) Notice: Subject to any disclaimer, the term of this patent is extended or adjusted under 35 U.S.C. 154(b) by 150 days.

(21) Appl. No.: 18/704,643

(22) PCT Filed: Oct. 27, 2022

(86) PCT No.: PCT/EP2022/080140
§ 371 (c)(1),
(2) Date: Apr. 25, 2024

(87) PCT Pub. No.: WO2023/073137
PCT Pub. Date: May 4, 2023

(65) Prior Publication Data
US 2025/0032107 A1     Jan. 30, 2025

Related U.S. Application Data

(60) Provisional application No. 63/407,137, filed on Sep. 15, 2022, provisional application No. 63/341,953, (Continued)

(51) Int. Cl.
A61B 17/00     (2006.01)

(52) U.S. Cl.
CPC .................... A61B 17/0057 (2013.01); *A61B 2017/00004* (2013.01); *A61B 2017/00367* (2013.01); (Continued)

(58) Field of Classification Search
CPC .................. A61M 29/00; A61M 25/04; A61M 2025/1093; A61F 2/82; A61F 2/06; (Continued)

(56) References Cited

U.S. PATENT DOCUMENTS 321,721 A      7/1885   Hassan
2,001,638 A    5/1935   Gustaf
(Continued)

FOREIGN PATENT DOCUMENTS

CN      101400308 A     4/2009
CN      104287803 A     1/2015
(Continued)

OTHER PUBLICATIONS

International Search Report for PCT/EP2022/080140, 6 pages (mailed Feb. 13, 2023).
(Continued)

*Primary Examiner* — Mohamed G Gabr
(74) *Attorney, Agent, or Firm* — Choate, Hall & Stewart LLP; William R. Haulbrook; Peter A. Flynn

(57) ABSTRACT

An implantable device for sealing an aperture in a tissue of a body vessel, includes: an external fixation disposed on the outside of a vessel wall; a scaffold disposed on the inside of the vessel wall and interfacing with the external fixation, at least a portion of the scaffold disposed through an aperture in the vessel wall; and a patch disposed on the inside of the vessel wall and sandwiched between the external fixation and the scaffold, the patch substantially covering the full area of the aperture, thereby sealing the aperture.

11 Claims, 77 Drawing Sheets

Related U.S. Application Data filed on May 13, 2022, provisional application No. 63/274,466, filed on Nov. 1, 2021.

(52) U.S. Cl.
CPC ............... *A61B 2017/00477* (2013.01); *A61B 2017/00592* (2013.01); *A61B 2017/00615* (2013.01); *A61B 2017/00623* (2013.01); *A61B 2017/00654* (2013.01); *A61B 2017/00862* (2013.01); *A61B 2017/00871* (2013.01)

(58) Field of Classification Search
CPC ...... A61B 17/0057; A61B 2017/00004; A61B 2017/00637; A61B 2017/00597; A61B 2017/00623; A61B 2017/00592; A61B 2017/00867; A61B 2017/00893; A61B 2017/00615; A61B 2017/00646; A61B 2017/00889; A61B 2017/22038; A61B 2560/0412; A61B 17/00234; A61B 17/0218

See application file for complete search history.

(56) References Cited

U.S. PATENT DOCUMENTS

| | | | |
|---|---|---|---|
| 2,560,162 | A | 7/1951 | Ferguson |
| 2,778,254 | A | 1/1957 | Carapellotti |
| 3,874,388 | A | 4/1975 | King et al. |
| 4,299,230 | A | 11/1981 | Kubota |
| 4,583,540 | A | 4/1986 | Malmin |
| 4,650,472 | A | 3/1987 | Bates |
| 4,705,040 | A | 11/1987 | Mueller et al. |
| 4,744,364 | A | 5/1988 | Kensey |
| 4,852,568 | A | 8/1989 | Kensey |
| 4,890,612 | A | 1/1990 | Kensey |
| 4,896,668 | A | 1/1990 | Popoff et al. |
| 5,021,059 | A | 6/1991 | Kensey et al. |
| 5,037,433 | A | 8/1991 | Wilk et al. |
| 5,053,046 | A | 10/1991 | Janese |
| 5,085,661 | A | 2/1992 | Moss |
| 5,127,412 | A | 7/1992 | Cosmetto et al. |
| 5,171,258 | A | 12/1992 | Bales et al. |
| 5,192,301 | A | 3/1993 | Kamiya et al. |
| 5,219,335 | A | 6/1993 | Willard et al. |
| 5,269,804 | A | 12/1993 | Bales et al. |
| 5,282,827 | A | 2/1994 | Kensey et al. |
| 5,320,461 | A | 6/1994 | Stanesic |
| 5,330,488 | A | 7/1994 | Goldrath |
| 5,336,231 | A | 8/1994 | Adair |
| 5,342,393 | A | 8/1994 | Stack |
| 5,350,399 | A | 9/1994 | Erlebacher et al. |
| 5,366,480 | A | 11/1994 | Corriveau et al. |
| 5,391,182 | A | 2/1995 | Chin |
| 5,431,639 | A | 7/1995 | Shaw |
| 5,462,560 | A | 10/1995 | Stevens |
| 5,470,337 | A | 11/1995 | Moss |
| 5,501,691 | A | 3/1996 | Goldrath |
| 5,501,700 | A | 3/1996 | Hirata |
| 5,507,755 | A | 4/1996 | Gresl et al. |
| 5,527,322 | A | 6/1996 | Klein et al. |
| 5,531,759 | A | 7/1996 | Kensey et al. |
| 5,545,178 | A | 8/1996 | Kensey et al. |
| 5,549,633 | A | 8/1996 | Evans et al. |
| 5,593,422 | A | 1/1997 | Muijs Van de Moer et al. |
| 5,601,557 | A | 2/1997 | Hayhurst |
| 5,601,571 | A | 2/1997 | Moss |
| 5,620,461 | A | 4/1997 | Muijs Van De Moer et al. |
| 5,653,716 | A | 8/1997 | Malo et al. |
| 5,662,681 | A | 9/1997 | Nash et al. |
| 5,665,096 | A | 9/1997 | Yoon |
| 5,676,689 | A | 10/1997 | Kensey et al. |
| 5,690,674 | A | 11/1997 | Diaz |
| 5,700,273 | A | 12/1997 | Buelna et al. |
| 5,700,277 | A | 12/1997 | Nash et al. |
| 5,707,393 | A | 1/1998 | Kensey et al. |
| 5,722,981 | A | 3/1998 | Stevens |
| 5,755,727 | A | 5/1998 | Kontos |
| 5,782,861 | A | 7/1998 | Cragg et al. |
| 5,797,939 | A | 8/1998 | Yoon |
| 5,814,065 | A | 9/1998 | Diaz |
| 5,817,074 | A | 10/1998 | Racz |
| 5,827,281 | A | 10/1998 | Levin |
| 5,860,990 | A | 1/1999 | Nobles et al. |
| 5,861,003 | A | 1/1999 | Latson et al. |
| 5,868,762 | A | 2/1999 | Cragg et al. |
| 5,916,236 | A | 6/1999 | Muijs Van de Moer et al. |
| 5,935,147 | A | 8/1999 | Kensey et al. |
| 5,941,899 | A | 8/1999 | Granger et al. |
| 5,954,732 | A | 9/1999 | Hart et al. |
| 5,997,515 | A | 12/1999 | de la Torre et al. |
| 6,007,563 | A | 12/1999 | Nash et al. |
| 6,033,427 | A | 3/2000 | Lee |
| 6,056,768 | A | 5/2000 | Cates et al. |
| 6,080,183 | A | 6/2000 | Tsugita et al. |
| 6,126,675 | A | 10/2000 | Shchervinsky et al. |
| 6,136,010 | A | 10/2000 | Modesitt et al. |
| 6,179,863 | B1 | 1/2001 | Kensey et al. |
| 6,190,400 | B1 | 2/2001 | Van De Moer et al. |
| 6,200,328 | B1 | 3/2001 | Cragg et al. |
| 6,206,895 | B1 | 3/2001 | Levinson |
| 6,241,768 | B1 | 6/2001 | Agarwal et al. |
| 6,245,080 | B1 | 6/2001 | Levinson |
| 6,296,658 | B1 | 10/2001 | Gershony et al. |
| 6,319,263 | B1 | 11/2001 | Levinson |
| 6,350,274 | B1 | 2/2002 | Li |
| 6,375,671 | B1 | 4/2002 | Kobayashi et al. |
| 6,383,208 | B1 | 5/2002 | Sancoff et al. |
| 6,395,015 | B1 | 5/2002 | Borst et al. |
| 6,398,796 | B2 | 6/2002 | Levinson |
| 6,425,911 | B1 | 7/2002 | Akerfeldt et al. |
| 6,461,364 | B1 | 10/2002 | Ginn et al. |
| 6,485,481 | B1 | 11/2002 | Pfeiffer |
| 6,500,184 | B1 | 12/2002 | Chan et al. |
| 6,508,828 | B1 | 1/2003 | Akerfeldt et al. |
| 6,520,951 | B1 | 2/2003 | Carrillo, Jr. et al. |
| 6,596,012 | B2 | 7/2003 | Akerfeldt et al. |
| 6,596,014 | B2 | 7/2003 | Levinson et al. |
| 6,638,286 | B1 | 10/2003 | Burbank et al. |
| 6,669,707 | B1 | 12/2003 | Swanstrom et al. |
| 6,669,735 | B1 | 12/2003 | Pelissier |
| 6,702,835 | B2 | 3/2004 | Ginn |
| 6,730,112 | B2 | 5/2004 | Levinson |
| 6,764,500 | B1 | 7/2004 | Muijs Van De Moer et al. |
| 6,770,070 | B1 | 8/2004 | Balbierz |
| 6,779,701 | B2 | 8/2004 | Bailly et al. |
| 6,786,915 | B2 | 9/2004 | Akerfeldt et al. |
| 6,800,082 | B2 | 10/2004 | Rousseau |
| 6,860,895 | B1 | 3/2005 | Akerfeldt et al. |
| 6,890,342 | B2 | 5/2005 | Zhu et al. |
| 6,932,824 | B1 | 8/2005 | Roop et al. |
| 6,939,363 | B2 | 9/2005 | Akerfeldt |
| 6,942,674 | B2 | 9/2005 | Belef et al. |
| 6,949,107 | B2 | 9/2005 | McGuckin, Jr. et al. |
| 6,949,114 | B2 | 9/2005 | Milo et al. |
| 6,964,668 | B2 | 11/2005 | Modesitt et al. |
| 6,969,397 | B2 | 11/2005 | Ginn |
| 6,974,244 | B1 | 12/2005 | Lin |
| 6,984,219 | B2 | 1/2006 | Ashby et al. |
| 6,989,022 | B2 | 1/2006 | Nowakowski |
| 6,997,940 | B2 | 2/2006 | Bonutti |
| 7,001,398 | B2 | 2/2006 | Carley et al. |
| 7,001,400 | B1 | 2/2006 | Modesitt et al. |
| 7,008,440 | B2 | 3/2006 | Sing et al. |
| 7,008,441 | B2 | 3/2006 | Zucker |
| 7,008,442 | B2 | 3/2006 | Brightbill |
| 7,094,248 | B2 | 8/2006 | Bachinski et al. |
| 7,144,411 | B2 | 12/2006 | Ginn et al. |
| 7,169,168 | B2 | 1/2007 | Muijs Van De Moer et al. |
| 7,326,221 | B2 | 2/2008 | Sakamoto et al. |
| 7,462,188 | B2 | 12/2008 | McIntosh |
| 7,534,248 | B2 | 5/2009 | Mikkaichi et al. |
| 7,569,063 | B2 | 8/2009 | Bailly et al. |
| 7,662,161 | B2 | 2/2010 | Briganti et al. |

(56) References Cited

U.S. PATENT DOCUMENTS

| | | |
|---|---|---|
| 7,678,133 B2 | 3/2010 | Modesitt |
| 7,753,935 B2 | 7/2010 | Brett et al. |
| 7,846,180 B2 | 12/2010 | Cerier |
| 7,850,710 B2 | 12/2010 | Huss |
| 7,918,868 B2 | 4/2011 | Marshall et al. |
| 7,998,169 B2 | 8/2011 | Modesitt |
| 8,002,791 B2 | 8/2011 | Modesitt |
| 8,002,792 B2 | 8/2011 | Modesitt |
| 8,002,793 B2 | 8/2011 | Modesitt |
| 8,012,168 B2 | 9/2011 | Modesitt |
| 8,083,767 B2 | 12/2011 | Modesitt |
| 8,137,380 B2 | 3/2012 | Green et al. |
| 8,177,795 B2 | 5/2012 | Niese et al. |
| 8,241,325 B2 | 8/2012 | Modesitt |
| 8,267,942 B2 | 9/2012 | Szabo et al. |
| 8,361,092 B1 | 1/2013 | Asfora |
| 8,529,431 B2 | 9/2013 | Baker et al. |
| 8,597,324 B2 | 12/2013 | Briganti et al. |
| 8,652,166 B2 | 2/2014 | Åkerfeldt |
| 8,821,507 B2 | 9/2014 | Axelson, Jr. et al. |
| 8,906,050 B2 | 12/2014 | Brett et al. |
| 9,060,751 B2 | 6/2015 | Martin et al. |
| 9,610,070 B2 | 4/2017 | Martin |
| 9,662,099 B2 | 5/2017 | Grant et al. |
| 9,850,013 B2 | 12/2017 | Grant et al. |
| 10,206,668 B2 | 2/2019 | McGoldrick et al. |
| 10,307,145 B2 | 6/2019 | Shipp |
| 10,314,727 B2 | 6/2019 | Liu et al. |
| 10,433,826 B2 | 10/2019 | Grant et al. |
| 11,141,142 B2 | 10/2021 | McGoldrick et al. |
| 11,311,280 B2 | 4/2022 | McGoldrick et al. |
| 11,357,486 B2 | 6/2022 | Martin et al. |
| 11,478,235 B2 | 10/2022 | Grant et al. |
| 12,016,542 B2 | 6/2024 | Grant et al. |
| 12,082,798 B2 | 9/2024 | Grant et al. |
| 12,274,427 B2 | 4/2025 | Martin et al. |
| 12,364,469 B2 | 7/2025 | McGoldrick et al. |
| 12,453,543 B2 | 10/2025 | Grant et al. |
| 2001/0044631 A1 | 11/2001 | Akin et al. |
| 2002/0019648 A1 | 2/2002 | Akerfeldt et al. |
| 2002/0019649 A1 | 2/2002 | Sikora et al. |
| 2002/0055767 A1 | 5/2002 | Forde et al. |
| 2002/0107506 A1 | 8/2002 | McGuckin et al. |
| 2002/0169377 A1 | 11/2002 | Khairkhahan et al. |
| 2002/0177864 A1 | 11/2002 | Camrud |
| 2002/0198562 A1 | 12/2002 | Akerfeldt et al. |
| 2003/0050665 A1 | 3/2003 | Ginn |
| 2003/0060846 A1 | 3/2003 | Egnelov et al. |
| 2003/0078598 A1 | 4/2003 | Ginn et al. |
| 2003/0093093 A1 | 5/2003 | Modesitt et al. |
| 2003/0120305 A1 | 6/2003 | Jud et al. |
| 2003/0144695 A1 | 7/2003 | McGuckin et al. |
| 2003/0216756 A1 | 11/2003 | Klein et al. |
| 2004/0082906 A1 | 4/2004 | Tallarida et al. |
| 2004/0092964 A1 | 5/2004 | Modesitt et al. |
| 2004/0092969 A1 | 5/2004 | Kumar |
| 2004/0093025 A1 | 5/2004 | Egnelov |
| 2004/0098044 A1 | 5/2004 | Van de Moer et al. |
| 2004/0133238 A1 | 7/2004 | Cerier |
| 2004/0176798 A1 | 9/2004 | Epstein et al. |
| 2004/0243122 A1 | 12/2004 | Auth et al. |
| 2005/0021055 A1 | 1/2005 | Toubia et al. |
| 2005/0021059 A1 | 1/2005 | Cole et al. |
| 2005/0033326 A1 | 2/2005 | Briganti et al. |
| 2005/0070957 A1 | 3/2005 | Das |
| 2005/0143817 A1 | 6/2005 | Hunter et al. |
| 2005/0149065 A1 | 7/2005 | Modesitt |
| 2005/0181008 A1 | 8/2005 | Hunter et al. |
| 2005/0209613 A1 | 9/2005 | Roop et al. |
| 2005/0251201 A1 | 11/2005 | Roue et al. |
| 2005/0267520 A1 | 12/2005 | Modesitt |
| 2005/0273135 A1 | 12/2005 | Chanduszko et al. |
| 2005/0288706 A1 | 12/2005 | Widomski et al. |
| 2006/0100665 A1 | 5/2006 | Von Oepen et al. |
| 2006/0106418 A1 | 5/2006 | Seibold et al. |
| 2006/0142784 A1 | 6/2006 | Kontos |
| 2006/0142797 A1 | 6/2006 | Egnelov |
| 2006/0265008 A1 | 11/2006 | Maruyama et al. |
| 2006/0287673 A1 | 12/2006 | Brett et al. |
| 2007/0112385 A1 | 5/2007 | Conlon |
| 2007/0135826 A1 | 6/2007 | Zaver et al. |
| 2007/0179509 A1 | 8/2007 | Nagata et al. |
| 2007/0179527 A1 | 8/2007 | Eskuri et al. |
| 2007/0197858 A1 | 8/2007 | Goldfarb et al. |
| 2007/0255313 A1 | 11/2007 | Modesitt |
| 2007/0282351 A1 | 12/2007 | Harada et al. |
| 2007/0282373 A1 | 12/2007 | Ashby et al. |
| 2008/0004689 A1 | 1/2008 | Jahnke et al. |
| 2008/0109017 A1 | 5/2008 | Herweck et al. |
| 2008/0228204 A1 | 9/2008 | Hamilton et al. |
| 2008/0243148 A1 | 10/2008 | Mikkaichi et al. |
| 2008/0312646 A9 | 12/2008 | Auth et al. |
| 2009/0012521 A1 | 1/2009 | Axelson, Jr. et al. |
| 2009/0018574 A1 | 1/2009 | Martin |
| 2009/0048559 A1 | 2/2009 | Grathwohl |
| 2009/0088723 A1 | 4/2009 | Khosravi et al. |
| 2009/0112257 A1 | 4/2009 | Preinitz et al. |
| 2009/0143815 A1 | 6/2009 | Eidenschink et al. |
| 2009/0143821 A1 | 6/2009 | Stupak |
| 2009/0192435 A1 | 7/2009 | Gregersen |
| 2009/0287118 A1 | 11/2009 | Malek |
| 2009/0312786 A1 | 12/2009 | Trask et al. |
| 2009/0319017 A1 | 12/2009 | Berez et al. |
| 2010/0022823 A1 | 1/2010 | Goldfarb et al. |
| 2010/0094425 A1 | 4/2010 | Bentley et al. |
| 2010/0114159 A1 | 5/2010 | Roorda et al. |
| 2010/0125296 A1 | 5/2010 | Modesitt |
| 2010/0152772 A1 | 6/2010 | Brett et al. |
| 2010/0222796 A1 | 9/2010 | Brett et al. |
| 2010/0228184 A1 | 9/2010 | Mavani et al. |
| 2010/0292717 A1 | 11/2010 | Petter-Puchner et al. |
| 2010/0324608 A1 | 12/2010 | Albertorio et al. |
| 2011/0077667 A1 | 3/2011 | Singhatat et al. |
| 2011/0082495 A1 | 4/2011 | Ruiz |
| 2011/0087270 A1 | 4/2011 | Penner et al. |
| 2011/0224728 A1 | 9/2011 | Martin et al. |
| 2011/0270284 A1 | 11/2011 | Beauchamp et al. |
| 2012/0059399 A1 | 3/2012 | Hoke et al. |
| 2012/0089166 A1 | 4/2012 | Modesitt |
| 2012/0165957 A1 | 6/2012 | Everland et al. |
| 2012/0226308 A1 | 9/2012 | Martin et al. |
| 2012/0226309 A1 | 9/2012 | Jonsson |
| 2012/0296275 A1 | 11/2012 | Martin et al. |
| 2012/0302987 A1 | 11/2012 | Jonsson |
| 2013/0116799 A1 | 5/2013 | Derwin et al. |
| 2013/0218125 A1 | 8/2013 | Stopek et al. |
| 2013/0218201 A1 | 8/2013 | Obermiller et al. |
| 2013/0274795 A1 | 10/2013 | Grant et al. |
| 2014/0018846 A1 | 1/2014 | Grant et al. |
| 2014/0018847 A1 | 1/2014 | Grant et al. |
| 2014/0058439 A1 | 2/2014 | White |
| 2014/0088343 A1 | 3/2014 | Arcand et al. |
| 2014/0180314 A1 | 6/2014 | Asfora |
| 2014/0194926 A1 | 7/2014 | Bailly et al. |
| 2014/0200597 A1 | 7/2014 | Klein et al. |
| 2014/0207183 A1 | 7/2014 | Shipp |
| 2014/0277113 A1 | 9/2014 | Stanley et al. |
| 2014/0345109 A1* | 11/2014 | Grant ................... B65B 39/007<br>29/446 |
| 2015/0045818 A1 | 2/2015 | Kim et al. |
| 2016/0051239 A1 | 2/2016 | Martin et al. |
| 2016/0166241 A1* | 6/2016 | McGoldrick .......... B05D 3/002<br>606/213 |
| 2016/0174953 A1 | 6/2016 | Grant et al. |
| 2017/0181736 A1 | 6/2017 | McGoldrick et al. |
| 2017/0281142 A1 | 10/2017 | Martin et al. |
| 2017/0333014 A1 | 11/2017 | Grant et al. |
| 2018/0325505 A1 | 11/2018 | Phillips |
| 2019/0021710 A1* | 1/2019 | McGoldrick ...... A61B 17/0057 |
| 2020/0138421 A1 | 5/2020 | Grant et al. |
| 2022/0218322 A1 | 7/2022 | McGoldrick et al. |
| 2022/0218323 A1 | 7/2022 | Martin et al. |
| 2022/0257225 A1 | 8/2022 | Grant et al. |
| 2023/0000477 A1 | 1/2023 | Grant et al. |

(56) References Cited

U.S. PATENT DOCUMENTS

| | | | |
|---|---|---|---|
| 2023/0157679 A1 | 5/2023 | Walters et al. | |
| 2023/0165578 A1 | 6/2023 | Walters et al. | |
| 2024/0325010 A1 | 10/2024 | McGoldrick et al. | |
| 2024/0366205 A1 | 11/2024 | Grant et al. | |
| 2025/0312022 A1 | 10/2025 | McGoldrick et al. | |
| 2025/0366838 A1 | 12/2025 | Grant et al. | |

FOREIGN PATENT DOCUMENTS

| | | |
|---|---|---|
| CN | 104771200 A | 7/2015 |
| CN | 105073064 A | 11/2015 |
| DE | 19711288 B4 | 11/2004 |
| DE | 102010048908 A1 | 4/2012 |
| DE | 102013101338 A1 | 8/2014 |
| EP | 0551198 A1 | 7/1993 |
| EP | 0761250 A1 | 3/1997 |
| EP | 0894475 A1 | 2/1999 |
| EP | 1 046 375 A1 | 10/2000 |
| EP | 2260770 A2 | 12/2010 |
| EP | 2 292 147 A1 | 3/2011 |
| EP | 2 628 592 A1 | 8/2013 |
| EP | 2 777 543 A1 | 9/2014 |
| EP | 4190248 A1 | 6/2023 |
| WO | WO-1994/008513 A1 | 4/1994 |
| WO | WO-00/07520 A1 | 2/2000 |
| WO | WO-2000/033744 A1 | 6/2000 |
| WO | WO-2002/102236 A2 | 12/2002 |
| WO | WO-2004/012601 A2 | 2/2004 |
| WO | WO-2004/012603 A2 | 2/2004 |
| WO | WO-2004/012627 A1 | 2/2004 |
| WO | WO-2006/117766 A2 | 11/2006 |
| WO | WO-2007/011353 A2 | 1/2007 |
| WO | WO-2007/057933 A1 | 5/2007 |
| WO | WO-2007/089603 A2 | 8/2007 |
| WO | WO-2008/042229 A2 | 4/2008 |
| WO | WO-2008/152617 A2 | 12/2008 |
| WO | WO-2009/070651 A1 | 6/2009 |
| WO | WO-2009/149455 A1 | 12/2009 |
| WO | WO-2010/027693 A2 | 3/2010 |
| WO | WO-2010/123821 A1 | 10/2010 |
| WO | WO-2011/080588 A2 | 7/2011 |
| WO | WO-2012/090069 A2 | 7/2012 |
| WO | WO-2012/156819 A2 | 11/2012 |
| WO | WO-2013/007534 A1 | 1/2013 |
| WO | WO-2013/128292 A2 | 9/2013 |
| WO | WO-2013/188351 A2 | 12/2013 |
| WO | WO-2014/140325 A1 | 9/2014 |
| WO | WO-2014/141209 A1 | 9/2014 |
| WO | WO-2014/149642 A2 | 9/2014 |
| WO | WO-2016/096930 A1 | 6/2016 |
| WO | WO-2016/096932 A1 | 6/2016 |
| WO | WO-2017/102941 A1 | 6/2017 |
| WO | WO-2020/141122 A1 | 7/2020 |
| WO | WO-2022/175321 A1 | 8/2022 |
| WO | WO-2023/073137 A1 | 5/2023 |

OTHER PUBLICATIONS

Written Opinion for PCT/EP2022/080140, 12 pages (mailed Feb. 13, 2023).

U.S. Appl. No. 62/092,212, filed Dec. 15, 2014, McGoldrick et al..

U.S. Appl. No. 62/092,235, filed Dec. 15, 2014, Grant et al..

U.S. Appl. No. 62/092,240, filed Dec. 15, 2014, Grant et al..

European Patent Office Partial Supplementary Search Report. Application No. 12784868.7, Jan. 12, 2015, 5 pages.

Extended European Search Report, Application No. EP 11852355.4, Sep. 28, 2015, 7 pages.

Grant, et al., Hales' 1733 Haemastaticks, Anesthesiology, 112(1) (2010).

Hales, Stephen, Statical Essays, vol. 2 (1773).

International Preliminary Report on Patentability, PCT/IB2010/003461, Jul. 12, 2012, 10 pages.

International Preliminary Report on Patentability, PCT/IE2006/000043, Oct. 30, 2007, 10 pages.

International Search Report, International Application No. PCT/EP2022/053810, Jun. 13, 2022, 8 pages.

International Search Report, PCT/EP2015/079904, 7 pages, Mar. 1, 2016.

International Search Report, PCT/EP2015/079906 (Closure Apparatus With Flexible Sealable Member and Flexible Support Member, filed Dec. 15, 2015), 7 pages, May 24, 2016.

International Search Report, PCT/EP2016/081183, 5 pages, Mar. 20, 2017.

International Search Report, PCT/IB2010/003461, Oct. 11, 2011, 6 pages.

International Search Report, PCT/IB2011/003295, Jun. 29, 2012, 4 pages.

International Search Report, PCT/IB2012/001101, Jan. 30, 2013, 3 pages.

International Search Report, PCT/IB2013/000839, Jan. 14, 2014, 6 pages.

International Search Report, PCT/IB2014/059848, Jul. 7, 2014, 5 pages.

Written Opinion, International Application No. PCT/EP2022/053810, Jun. 13, 2022, 8 pages.

Written Opinion, PCT/EP2015/079904, 8 pages, Mar. 1, 2016.

Written Opinion, PCT/EP2015/079906 (Closure Apparatus With Flexible Sealable Member and Flexible Support Member, filed Dec. 15, 2015), 11 pages, May 24, 2016.

Written Opinion, PCT/EP2016/081183, 12 pages, Mar. 20, 2017.

Written Opinion, PCT/IB2010/003461, Oct. 11, 2011, 9 pages.

Written Opinion, PCT/IB2011/003295, Jun. 29, 2012, 5 pages.

Written Opinion, PCT/IB2012/001101, Jan. 30, 2013, 5 pages.

Written Opinion, PCT/IB2013/000839, Jan. 14, 2014, 11 pages.

Written Opinion, PCT/IB2014/059848, Jul. 7, 2014, 8 pages.

Written Opinion, PCT/IE2006/000043, Oct. 29, 2007, 9 pages.

* cited by examiner

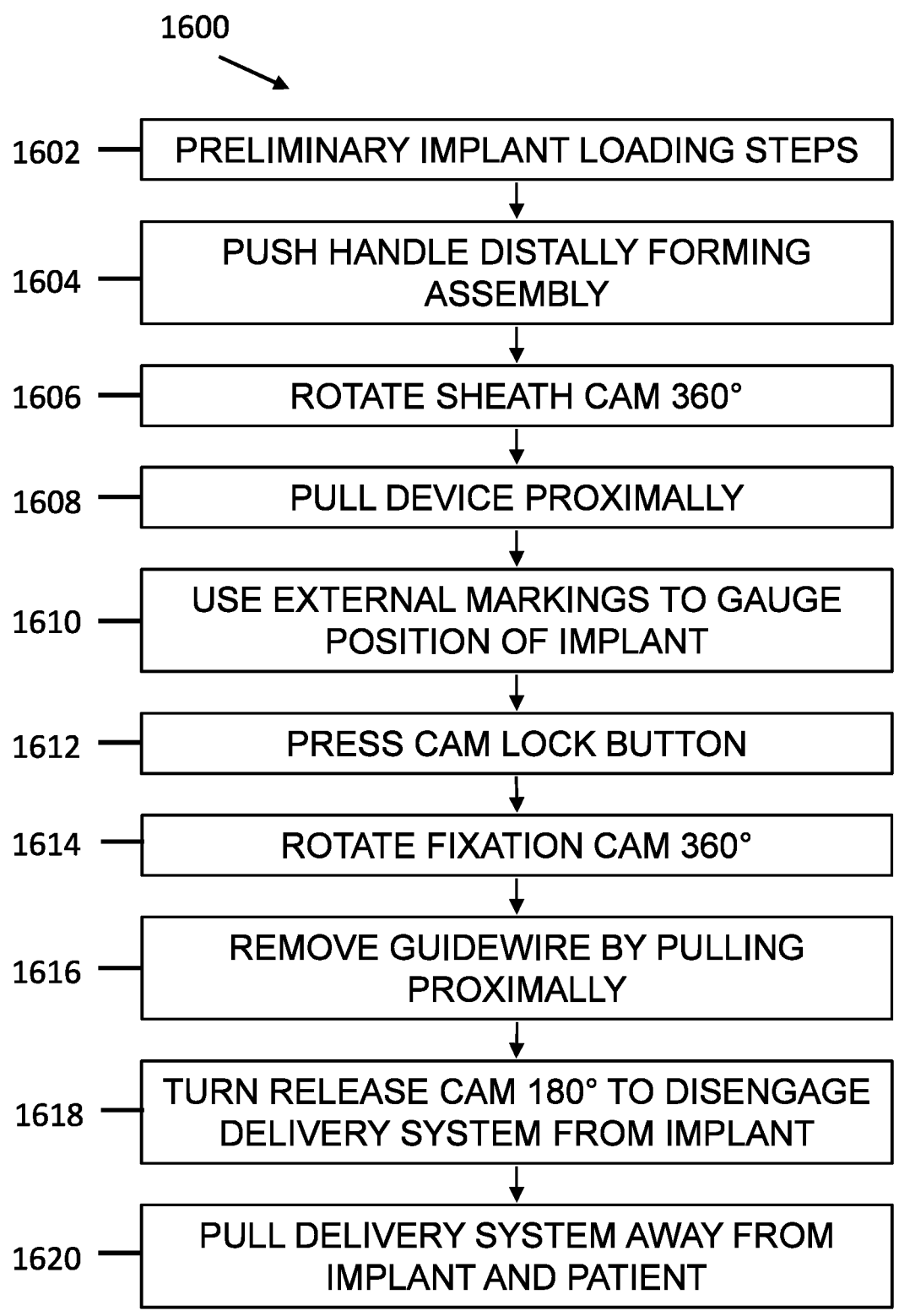

1600

1602 — PRELIMINARY IMPLANT LOADING STEPS

1604 — PUSH HANDLE DISTALLY FORMING ASSEMBLY

1606 — ROTATE SHEATH CAM 360°

1608 — PULL DEVICE PROXIMALLY

1610 — USE EXTERNAL MARKINGS TO GAUGE POSITION OF IMPLANT

1612 — PRESS CAM LOCK BUTTON

1614 — ROTATE FIXATION CAM 360°

1616 — REMOVE GUIDEWIRE BY PULLING PROXIMALLY

1618 — TURN RELEASE CAM 180° TO DISENGAGE DELIVERY SYSTEM FROM IMPLANT

1620 — PULL DELIVERY SYSTEM AWAY FROM IMPLANT AND PATIENT

FIG. 116

IMPLANT FOR VASCULAR CLOSURE

CROSS-REFERENCE TO RELATED APPLICATIONS

This application is a 371 National Stage entry of International Application No. PCT/EP2022/080140, filed Oct. 27, 2022, which claims priority to U.S. Provisional Application No. 63/407,137, filed Sep. 15, 2022, U.S. Provisional Application No. 63/341,953, filed May 13, 2022, and U.S. Provisional Application No. 63/274,466, filed Nov. 1, 2021. The disclosures of each of the above-referenced applications are incorporated by reference herein in their entireties.

BACKGROUND

During a surgical or endoscopic operation or surgery on a body vessel of a patient, e.g., a blood vessel, an aperture or opening or wound may be formed (e.g., from an arteriotomy or a venotomy) in the tissue of the vessel. Following the procedure, the aperture needs to be closed in order for the vessel to heal. One relatively new type of closure apparatus has a flexible disc that is delivered into the body vessel to seal the aperture. The disc retains the tissue in apposition until the aperture in the vessel is healed, allowing the wound to heal from the inside of the vessel.

In certain patients, the area surrounding the tissue within the body vessel may be diseased and/or may have accumulations (e.g., plaque or calcified lesions on the tissue wall). Due to the irregular surface topology of such areas, the effectiveness of the seal made by certain closure apparatuses is reduced, as channels are formed between the disc and the tissue surface.

There are benefits in improving the seal formed by a closure apparatus when closing an aperture formed in the tissue of the body vessel.

SUMMARY

The provided technologies provide an implant closure device having a mesh layer formed on a flexible substrate, collectively forming a sealable member or patch, which improves a seal of an aperture in the body vessel. During closure of the aperture, the patch is held against the inner-luminal tissue of the vessel wall such that the textured surface of the mesh layer is oriented against the tissue. The meshing facilitates a faster and more secure adherence of the patch to the surrounding edges at the puncture site. Furthermore, the provided technologies promote platelet-capture and encourage platelet aggregation on the mesh layer. The platelet impregnated mesh layer facilitates cellular adhesion, enabling the patch to act, in essence, as a "biological glue." Thus, faster time to hemostasis, improved security of the sealing, and improved apposition of the implant to the vessel wall can be obtained.

In some embodiments, the patch is sized such that the patch forms a tamponade of the aperture when the patch is positioned against an interior luminal surface of the tissue adjacent the aperture. The patch may be held in place at the aperture by an internal scaffold and by an external fixation, with the internal scaffold and external fixation mechanically held together with the patch and the tissue of the vessel sandwiched between them so that the patch covers the aperture. The combination of the patch, the scaffold, the external fixation and other components may be collectively termed a vascular closure device. In some embodiments, a delivery device may be used to position the components of the vascular closure device at the aperture. The combination of the vascular closure device and the delivery device may be collectively termed a vascular closure system.

Further features and aspects of example embodiments of the present invention are described in more detail below.

In one aspect, the present embodiments include an implantable device for sealing an aperture in a tissue of a body vessel, the implantable device comprising: an external fixation disposed on the outside of a vessel wall; a scaffold disposed on the inside of the vessel wall and interfacing with the external fixation, at least a portion of the scaffold disposed through an aperture in the vessel wall; and a patch disposed on the inside of the vessel wall and sandwiched between the external fixation and the scaffold, the patch substantially covering the full area of the aperture, thereby sealing the aperture.

In one aspect, the present disclosure provides a system for sealing an aperture in a tissue of a body vessel of a subject, which comprises (1) an implantable device comprising a flexible (e.g., rollable) patch that (a) is positionable against an internal surface of the tissue adjacent the aperture in the tissue when the implantable device is in a sealing position, (b) comprises a flexible substrate and a mesh layer disposed on (e.g., in contact with) the flexible substrate, and (c) has an elongated shape so that a longitudinal dimension of the flexible patch is greater than a lateral dimension of the flexible patch (e.g., wherein the flexible patch is oval in shape) (e.g., wherein the longitudinal dimension is at least 10, 20, 30, 40 or 50% greater than the lateral dimension); and (ii) a delivery device for delivering the implantable device into the subject for positioning of the flexible patch against the internal surface of the tissue adjacent the aperture.

In some embodiments, an average thickness of the flexible patch is greater than 100 µm (e.g., within a range of 100 µm to 500 µm, 200 µm to 400 µm, 200 µm to 300 µm, 200 µm to 280 µm or 200 µm to 250 µm).

In some embodiments, the aperture is located in a blood vessel, and a longitudinal axis of the flexible patch is aligned with (e.g., parallel to) a longitudinal axis of the blood vessel.

In some embodiments, the longitudinal dimension of the flexible patch is within a range of about 6 mm to about 10 mm and the lateral dimension of the flexible patch is within a range of about 4 mm to about 8 mm (e.g., wherein an outer diameter of the aperture is about 10 F).

In some embodiments, the longitudinal dimension of the flexible patch is within a range of about 10 mm to about 14 mm and the lateral dimension of the flexible patch is within a range of about 7 mm to about 11 mm (e.g., wherein an outer diameter of the aperture is about 15 F).

In some embodiments, the longitudinal dimension of the flexible patch is within a range of about 13 mm to about 17 mm and the lateral dimension of the flexible patch is within a range of about 10 mm to about 14 mm (e.g., wherein an outer diameter of the aperture is about 20 F).

In some embodiments, the longitudinal dimension of the flexible patch is within a range of about 18 mm to about 22 mm and the lateral dimension of the flexible patch is within a range of about 13 mm to about 17 mm (e.g., wherein an outer diameter of the aperture is about 26 F).

In some embodiments, the longitudinal dimension of the flexible patch is within a range of about 21 mm to about 25 mm and the lateral dimension of the flexible patch is within a range of about 15 mm to about 19 mm (e.g., wherein an outer diameter of the aperture is about 30 F).

In some embodiments, the longitudinal dimension of the flexible patch is within a range of about 25 mm to about 29 mm and the lateral dimension of the flexible patch is within a range of about 18 mm to about 22 mm (e.g., wherein an outer diameter of the aperture is about 35 F).

In some embodiments, an average thickness of the flexible substrate is within a range of 100 µm to 500 µm, 150 µm to 300 µm, 150 µm to 250 µm, or 190 µm to 220 µm.

In some embodiments, an average thickness of the mesh layer is within a range of 5 µm to 200 µm, 20 µm to 100 µm, or 20 µm to 80 µm.

In some embodiments, the mesh layer is in contact with the aperture when in the sealing position.

In some embodiments, the implantable device further comprises a support member or scaffold.

In some embodiments, the support member or scaffold comprises a base plate and a column or neck, the neck is disposed in and through the aperture, and the base is disposed in the body vessel to retain the patch against the interior surface of the tissue of the body vessel when the device is in the sealing position.

In some embodiments, the delivery system contains the implantable device, and the flexible patch is in a rolled conformation therein.

In some embodiments, the mesh layer comprises a plurality of electrospun fibers (e.g., facilitates tissue adhesion to the flexible patch by promoting platelet aggregation, or blood clotting with fibrin reinforcement of a platelet plug, etc., in the sealing position).

In some embodiments, the mesh layer comprises a synthetic agent and/or a biological agent.

In some embodiments, the implantable device comprises at least one material selected from the group consisting of polydioxanone, poly-L-lactide, poly-D-lactide, poly-DL-lactide, polyglycolide, ε-caprolactone, polyethylene glycol, and copolymers thereof.

In some embodiments, the implantable device comprises an external fixation positionable near an exterior surface of the tissue adjacent to the aperture when the device is in the sealing position. In some embodiments, the external fixation is moveable to be positioned near the exterior surface of the tissue adjacent to the aperture such that a portion of the tissue is disposed between the external fixation and the patch when the device is in the sealing position (e.g., wherein the neck comprises an engagement portion to secure the external fixation to the scaffold).

In some embodiments, the mesh layer comprises a plurality of fibers each having a diameter in a range from 0.3 µm to 8 µm.

In some embodiments, the plurality of fibers makes up from 1 volume % to 35 volume % or 5 volume % to 25 volume % of the mesh layer.

In some embodiments, the system includes a closure pin disposed within the scaffold neck for sealing the guidewire lumen after the guidewire is removed from the guidewire lumen. The closure pin may include an angled tip, a substantially circular pin head, a pair of first and second distally extending arms, a rupture portion, an offset bore, an angled pin, a slidable rod, and/or an L-shaped closure pin. Distally pushing the closure pin into the scaffold neck causes the closure pin to seal the guidewire lumen.

In some embodiments, the scaffold neck includes an internal taper, a gradual tapered portion, a ramp portion, a sleeve portion, an angled surface, and/or a partial bore.

In some embodiments, the scaffold neck extends externally at an angle from the base plate, the neck including at least one lumen disposed therethrough.

In some embodiments, the scaffold neck includes at least two retaining tabs, wherein the retaining tabs are disposed circumferentially around the exterior of the scaffold neck and extend radially away from the scaffold neck, and wherein the retaining tabs interface with a collar of the external fixation, thereby causing the external fixation to be coupled to the scaffold, with the patch sandwiched between the base plate of the scaffold and the external fixation.

In some embodiments, the external fixation includes: a collar; a base ring; an anterior rib connecting the collar and the base ring; and a posterior post connecting the collar and the base ring. In some embodiments, the external fixation further includes a tab disposed at an angle from the collar, the tab including a protrusion.

In some embodiments, the scaffold comprises a threaded portion at the base of the neck, the threads of the threaded portion interacting with the opening of the patch to hold the patch against the upper surface of the base plate of the scaffold.

In some embodiments, the closure pin includes: a cylindrical body; a tip disposed at the distal end of the cylindrical body that comprises at least one of an angled tip and a stepped tapered tip; and a substantially cylindrical head disposed at the proximal end of the cylindrical body.

In some embodiments, the pin head comprises a rectangular cutout, the rectangular cutout interfacing with the protrusion on the external fixation.

In some embodiments, the scaffold neck comprises at least one of an internal taper, a gradual tapered portion, and a ramp portion.

In some embodiments, each retaining tab of the scaffold neck includes: a first protrusion; a notch; a flat portion; and a second protrusion, wherein the first protrusion, the notch, the flat portion, and the second protrusion are arranged longitudinally within the retaining tab along an axial direction of the scaffold neck, wherein the first protrusion and the second protrusion extend out radially from the surface of the scaffold neck, wherein the first protrusion extends further radially outwardly than the second protrusion, and wherein the notch is disposed at a smaller radius that the second protrusion.

In some embodiments, a longitudinal dimension of the patch is within a range of about 6 to about 29 mm and a lateral dimension of the patch is within a range of about 4 mm to about 22 mm.

In some embodiments, the patch includes: a base layer having a thickness within a range of 190-220 µm; and an electrospun layer having a thickness within a range of 20-80 µm, wherein a total thickness of the patch is within a range of 210-300 µm.

In some embodiments, the patch comprises an opening disposed at the center of the patch, the scaffold neck passing through the opening in the patch.

In another aspect, the present embodiments are directed to a vascular closure system for sealing an aperture in a tissue of a body vessel, the system including: the implantable device; and a device delivery system, wherein the implantable device is stowed within the delivery system with the patch in a rolled configuration prior to delivery of the implantable device to the aperture in the tissue of the body vessel.

In some embodiments, the delivery system includes: an introducer sheath; a guidewire; a pusher shaft (or push tube); a delivery shaft; a loading cannula; a receiving funnel; an outer shaft (or fixation shaft); and a handle.

In some embodiments, the patch includes: a base layer comprising a thickness within a range of 190-220 µm; and an electrospun layer comprising a thickness within a range of 20-80 μm, wherein the total thickness of the patch is within a range of 210-300 μm.

In some embodiments, the handle comprises a handle body, a rotatable sheath cam, a cam lock, a rotatable fixation cam, and a rotatable release cam. In some embodiments, rotating the rotatable sheath cam causes the sheath to retract proximally, thereby allowing the scaffold and patch to exit from the introducer sheath and expand within the vessel. In some embodiments, rotating the rotatable fixation cam causes the external fixation to advance distally toward the scaffold and patch, thereby allowing the neck of the scaffold to engage with the collar of the external fixation.

In some embodiments, rotating the release cam causes the closure pin to be pushed into the neck of the scaffold, and causes the implantable device to be released.

In another aspect, the present embodiments are directed to a method of sealing an aperture in a body vessel using an implantable closure device and a closure system, including the following steps: inserting an introducer sheath of the closure system into a surgical opening and into the aperture; loading the implantable closure device into a loading cannula of the closure system; connecting the loading cannula to a receiving funnel of the closure system; pushing a handle of the closure system proximally to engage with the loading cannula; rotating a sheath cam on the handle by 360°; pulling the closure system proximally to retract the delivery system until the closure device is at the position of the aperture in the vessel to be closed; depressing a cam lock button on the handle; rotating a fixation cam on the handle by 360°; pulling a guidewire of the closure system proximally to remove it from the delivery system; rotating a release cam on the handle by 180°; and pulling the closure system proximally until the delivery system is completely removed from the surgical opening.

Definitions

In order for the present disclosure to be more readily understood, certain terms are first defined below. Additional definitions for the following terms and other terms are set forth throughout the specification.

In this application, the use of "or" means "and/or" unless stated otherwise. As used in this application, the term "comprise" and variations of the term, such as "comprising" and "comprises," are not intended to exclude other additives, components, integers or steps. As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

The term "biocompatible", as used herein is intended to describe materials that do not elicit a substantial detrimental response in vivo. In certain embodiments, the materials are "biocompatible" if they are not toxic to cells. In certain embodiments, materials are "biocompatible" if their addition to cells in vitro results in less than or equal to 20% cell death, and/or their administration in vivo does not induce inflammation or other such adverse effects. In certain embodiments, materials are biodegradable and/or bioabsorbable.

As used herein, "bioabsorbable" materials are those that, when introduced into cells, are broken down by cellular machinery (e.g., enzymatic degradation) or by hydrolysis into components that cells can either reuse, reabsorb, or dispose of without significant toxic effects on the cells. In certain embodiments, components generated by breakdown of a bioabsorbable material do not induce inflammation and/or other adverse effects in vivo. In some embodiments, bioabsorbable materials are enzymatically broken down. Alternatively or additionally, in some embodiments, bioabsorbable materials are broken down by hydrolysis. In some embodiments, bioabsorbable polymeric materials break down into their component polymers and/or monomers. In some embodiments, breakdown of bioabsorbable materials (including, for example, bioabsorbable polymeric materials) includes hydrolysis of ester bonds. In some embodiments, breakdown of materials (including, for example, bioabsorbable polymeric materials) includes cleavage of urethane linkages.

As used herein, "implant" is an object that is placed within a subject during a medical operation. The object may be biodegradable and/or bioabsorbable.

As used herein, "mesh" materials are those that, when introduced into a blood vessel, promote platelet capture (e.g., whereby the captured platelets encourages localized platelet activation, e.g., due to the contact with the collagen from the exposed wound, at the wound surface).

The phrase "physiological conditions", as used herein, relates to the range of chemical (e.g., pH, ionic strength) and biochemical (e.g., enzyme concentrations) conditions likely to be encountered in the intracellular and extracellular fluids of tissues. For most tissues, the physiological pH ranges from about 7.0 to 7.4.

The term "sample" refers to a volume or mass obtained, provided, and/or subjected to analysis. In some embodiments, a sample is or comprises a tissue sample, cell sample, a fluid sample, and the like. In some embodiments, a sample is taken from a subject (e.g., a human or animal subject). Those of ordinary skill in the art will appreciate that, in some embodiments, a "sample" is a "primary sample" in that it is obtained from a source (e.g., a subject); in some embodiments, a "sample" is the result of processing of a primary sample, for example to remove certain potentially contaminating components and/or to isolate or purify certain components of interest.

As used herein, the term "substantially", and grammatical equivalents, refer to the qualitative condition of exhibiting at least a majority and total or near-total extent or degree of a characteristic or property of interest. One of ordinary skill in the art will understand that material and chemical phenomena rarely, if ever, go to completion and/or proceed to completeness or achieve or avoid an absolute result.

As used herein, the term "subject" includes humans and mammals (e.g., mice, rats, pigs, cats, dogs, and horses). In many embodiments, subjects are mammals, particularly primates, especially humans. In some embodiments, subjects are livestock such as cattle, sheep, goats, cows, swine, and the like; poultry such as chickens, ducks, geese, turkeys, and the like; and domesticated animals particularly pets such as dogs and cats. In some embodiments (e.g., particularly in research contexts) subject mammals will be, for example, rodents (e.g., mice, rats, hamsters), rabbits, primates, or swine such as inbred pigs and the like.

Figures are presented herein for illustration purposes only, not for limitation.

BRIEF DESCRIPTION OF THE DRAWING

The Drawing, which is comprised of at least the following Figures, is for illustration purposes only, not for limitation.

FIG. 14 is a top view photograph of a scaffold base with a patch disposed thereon, according to the present embodiments.

FIG. 15 is a perspective view photograph of an assembled vascular closure device, according to the present embodiments.

FIG. 115 illustrates another cut-away perspective view of the interior of a delivery system handle, according to aspects of the present embodiments.

FIG. 116 illustrates a method of sealing an aperture, according to aspects of the present embodiments.

DETAILED DESCRIPTION

Overview

As described herein, illustrative embodiments provide a vascular closure implantable device for sealing an aperture in a tissue of a body vessel. Examples of a body vessel include a blood vessel, which may be a vein or an artery. Examples of the blood vessel include, but are not limited to, the femoral artery, subclavian artery, ascending and descending aorta, auxiliary and brachial arteries, femoral vein, iliac vein, subclavian vein, and vena cava. In some embodiments, the systems, devices, and methods are used to close a surgical perforation in a body cavity, such as the gastrointestinal tract, heart, peritoneal cavity, esophagus, vagina, rectum, trachea, bronchi, and blood vessel.

First Embodiment of Closure Device

Figures 1, 2:
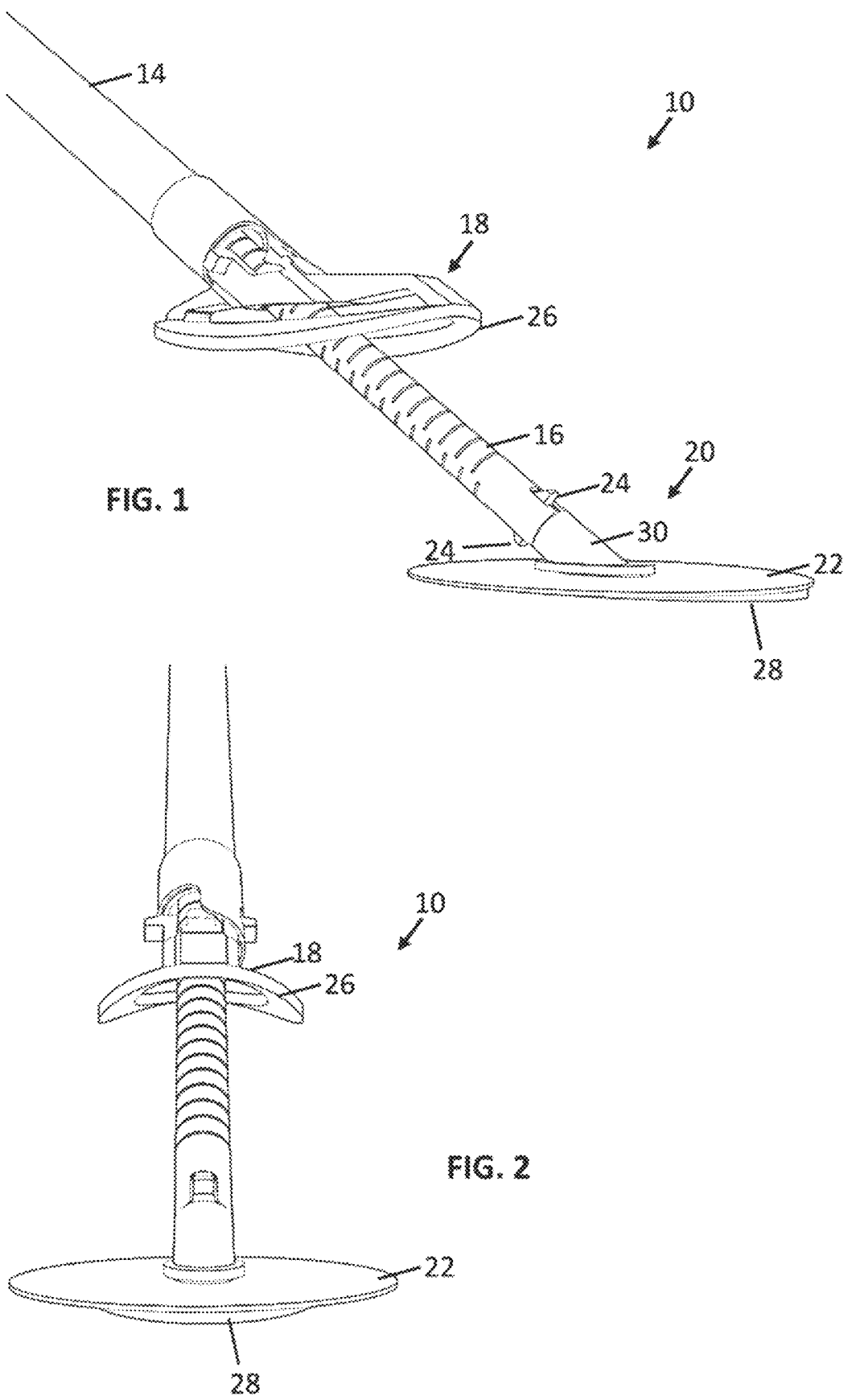
FIG. 1 is a perspective view of a vascular closure device and system, according to the present embodiments.
FIG. 2 is a front view of a vascular closure device and system, according to the present embodiments.

FIG. 1 is a perspective view of a vascular closure device 12 and system 10, according to the present embodiments. The system 10 includes an outer shaft 14, a distal scaffold retention shaft 16, and external fixation 18, a scaffold 20, and a patch 22. The outer shaft 14 and the distal scaffold retention shaft 16 may collectively form and/or be components of a delivery system. The external fixation 18, the scaffold 20, and the patch 22 collectively form the vascular closure device 10. A scaffold base 28 is visible under the patch 22. The scaffold 20 includes a scaffold neck 30 (or protrusion), protruding upwardly and at an angle from the scaffold base 28. In operation, the outer shaft 14 and the distal scaffold retention shaft 16 may be used to deliver the device 12 to an aperture or vascular opening such that the external fixation 18 may be coupled to the scaffold 20 via one or more retaining tabs 24 disposed in the scaffold neck 30 (for example, on either side, spaced out by about 180 degrees). The external fixation 18 includes an upper lip 26 which, in a final deployment position, is position outside a blood vessel, artery, etc. for helping to form a seal externally. The patch 22 and scaffold 20 (including the scaffold base 28) are disposed within the blood vessel, artery, vein, etc. to internally push against the vessel walls, opposite the upper lip 26.

Examples of the patch 22 (also referred to as a "flexible wing" or sealable member or patch) are described in U.S. Patent Application Publication No. 2014/0018847, titled "Percutaneous Perforation Closure Systems, Devices, and Methods," the content of which is incorporated by reference herein in its entirety. Among other things, this disclosure provides details of a variant of the patch 22 design, as well as the vascular closure device 12.

FIG. 2 is a front view of a vascular closure device 12 and system 10, according to the present embodiments. In the view of FIG. 2, the curvature of the upper lip 26 (part of the external fixation) is illustrated. The upper lip 26 is concave from the perspective of the patch 22 such that it is contoured to match the external contouring of the blood vessel, vein, artery, and/or other organ on which the device 12 is being deployed. The scaffold base 28 is also visible in FIG. 2.

Figure 3:
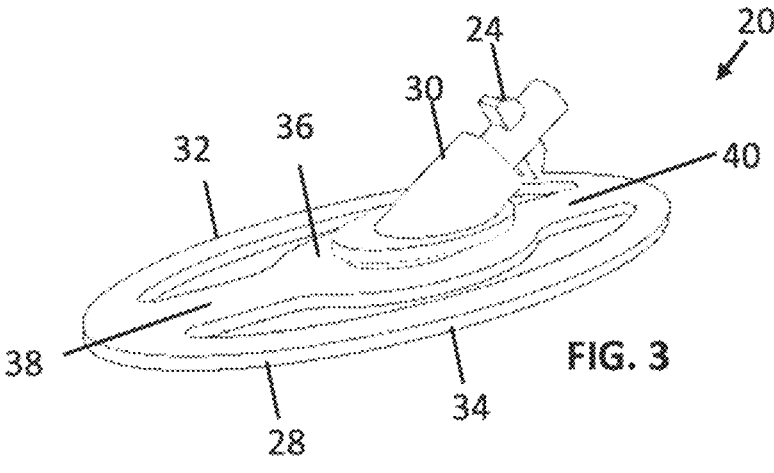
FIG. 3 is a perspective view of a scaffold, according to the present embodiments.
Figure 4:
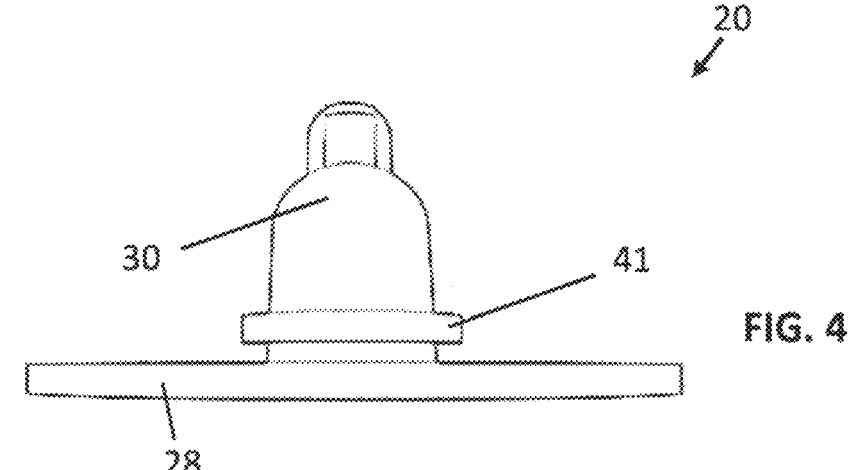
FIG. 4 is a front view of a scaffold, according to the present embodiments.

FIG. 3 is a perspective view of a scaffold 20, according to the present embodiments. The scaffold 20 may include the scaffold neck 30, the scaffold base 28, and one or more retaining tabs 24. The scaffold base 28 may include one or more curved members (for example, a first curved member 32 on a first side of the scaffold base 28 and a second curved member 34 on a second side of the scaffold base 28, opposite of the first curved member 32. Each of the first and second curved members 32, 34 may be separated from a central oval portion 36 via first and second gaps 42, 44 shown in FIG. 5. The scaffold neck 30 may protrude upwardly from the central oval portion 36, which may be oval-shaped and may be coupled to the proximal and distal portions of the scaffold base via proximal and distal straight members 40, 38. As illustrated in FIG. 4, the scaffold 20 may include a scaffold lip 41 disposed on a bottom portion of the scaffold neck 30 such that the patch 22 (shown in FIGS. 9-11) may be disposed onto the scaffold 20, and may stay in place when positioned thereon. Stated otherwise, the scaffold neck 30 is disposed through the patch 22, which rests above the scaffold base 28, but below the scaffold lip 41.

Figure 5:
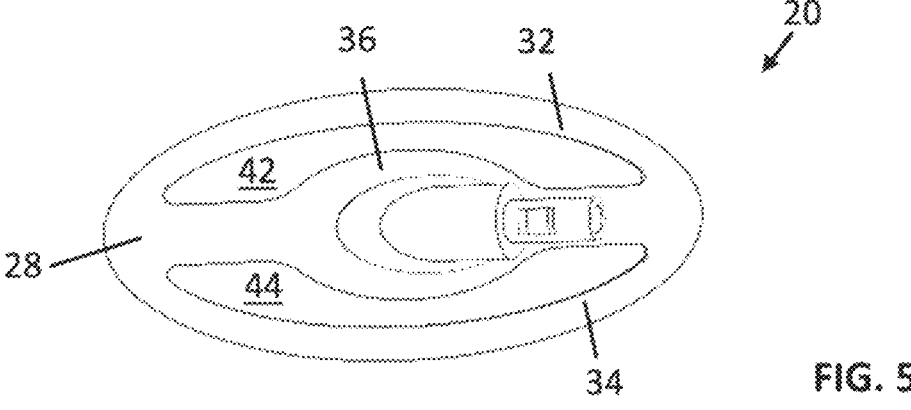
FIG. 5 is a top view of a scaffold, according to the present embodiments.

Referring to FIGS. 3-5, the scaffold may be generally oval-shaped and may include a length that is at least 2 times greater that the width (or in some embodiments, from about 1.75 to 2.25 times width, or from about 1.5 to about 2.5 times the width). The first and second curved members 32, 34, as well as the first and second gaps 42, 44 may be dimensioned such that the flexibility of the scaffold 20 may be "tuned" to allow sufficient flexibility for the scaffold 20 to be bendable (for example to fit within a loading cannula when being deployed within a blood vessel, in some embodiments), while also being rigid enough to provide structure and rigidity to the patch 22 during sealing. The oval shape of the scaffold 20 also helps to minimize the lateral dimension of the scaffold 20 during deployment through a vessel aperture, while simultaneously allowing for a larger interfacing surface area with the patch 22 while sealing.

Figure 6:
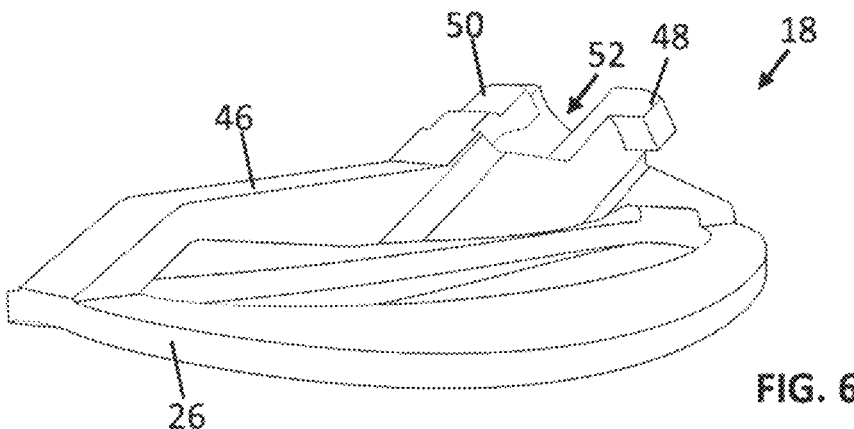
FIG. 6 is a perspective view of an external fixation, according to the present embodiments.
Figure 7:
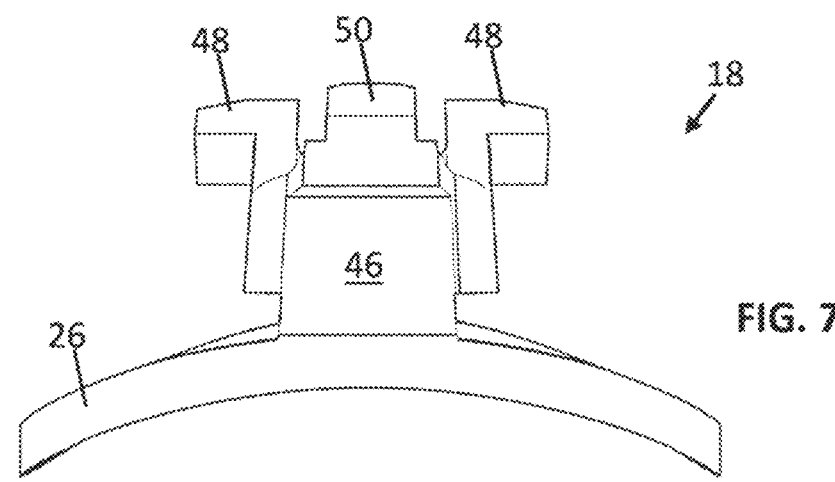
FIG. 7 is a front view of an external fixation, according to the present embodiments.
Figure 8:
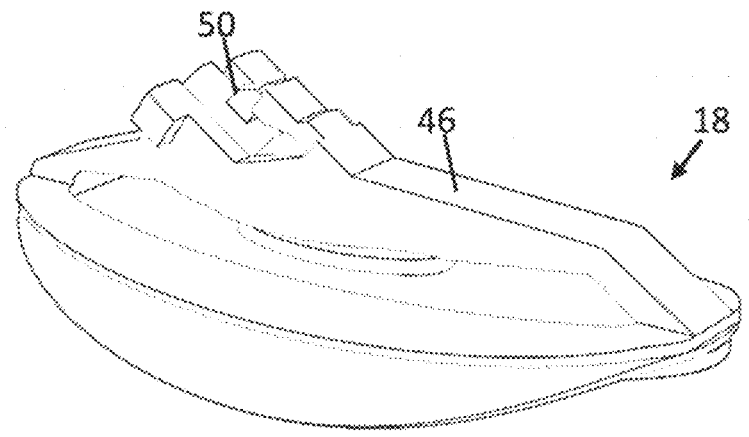
FIG. 8 is a perspective view of vascular closure device, according to the present embodiments.

FIGS. 6-8 show perspective and front views of the external fixation 18, according to the present embodiments. The external fixation 18 includes a rib 46 coupled to one or more lateral tabs 48, as well as at least one catch 50, and the upper lip 26. As the device is being deployed in its final position (i.e., in the sealing position) the scaffold neck 30 may be disposed within a space 52 within the external fixation 52 such that the one or more retaining tabs 24 of the scaffold 20 interface and catch on the one or more catches 50 of the external fixation 18, thereby fastening the two pieces together (with the patch 22, and walls of the blood vessel sandwiched between the upper lip 26 and the scaffold base 28). The one or more lateral tabs 48, when laterally squeezed together, may be used to subsequently release the external locator 18 from the scaffold 20, should the need arise.

Figure 9:
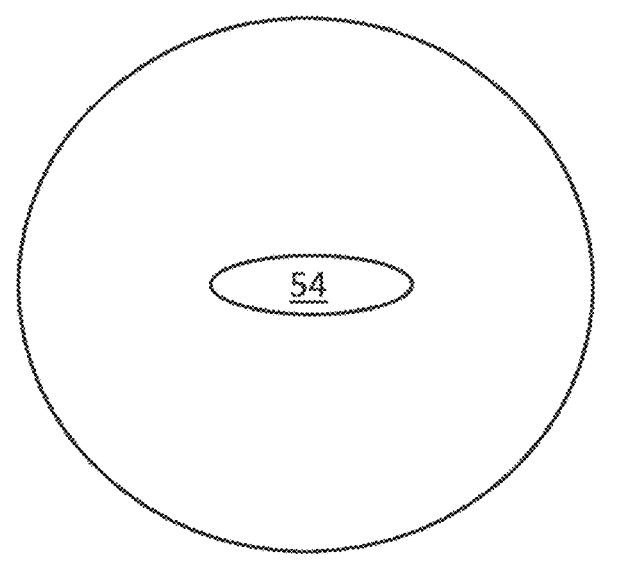
FIG. 9 is a top view of a patch, according to the present embodiments.

FIG. 9 illustrates a top view of the patch 22, according to the present embodiments. The patch 22 may include a hole 54 (for example, an oval-shaped hole 54) through which the scaffold neck 30 may be disposed while in operation.

Figure 10:
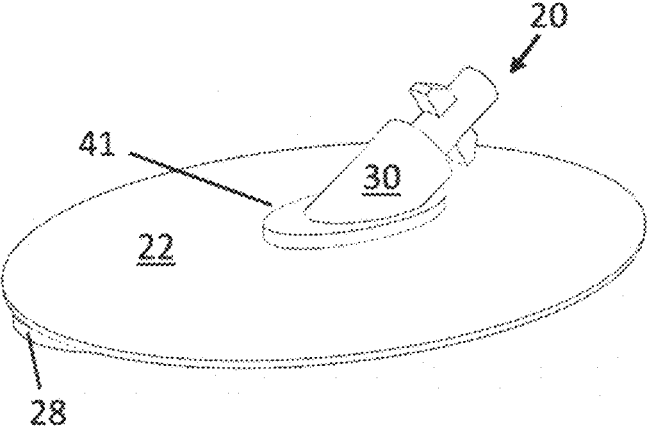
FIG. 10 is a perspective view of a scaffold with a patch disposed thereon, according to the present embodiments.

FIG. 10 is a perspective view of a scaffold 20 with a patch 22 disposed thereon, according to the present embodiments. The scaffold neck 30 may be disposed through the hole 54 in the patch 22 while the patch 22 may be layered between the scaffold base 28 and the scaffold lip 41.

Figure 11:
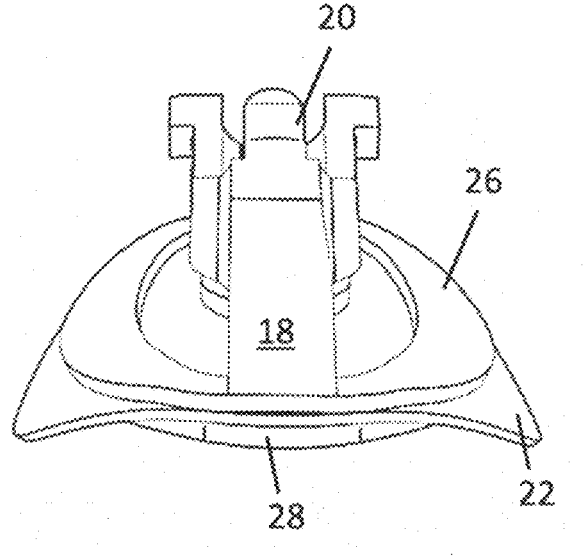
FIG. 11 is a front view of vascular closure device, according to the present embodiments.

FIG. 11 is a front view of vascular closure device 12, according to the present embodiments. The vascular closure device 12 includes the patch 22, scaffold 20, and external fixation 18 all assembled together with the patch 22 being disposed between the upper lip 26 and the scaffold base 28 (each of the patch 22 and the scaffold base 28 bending and/or flexing to match the contouring of the upper lip 26).

Figures 12, 13:
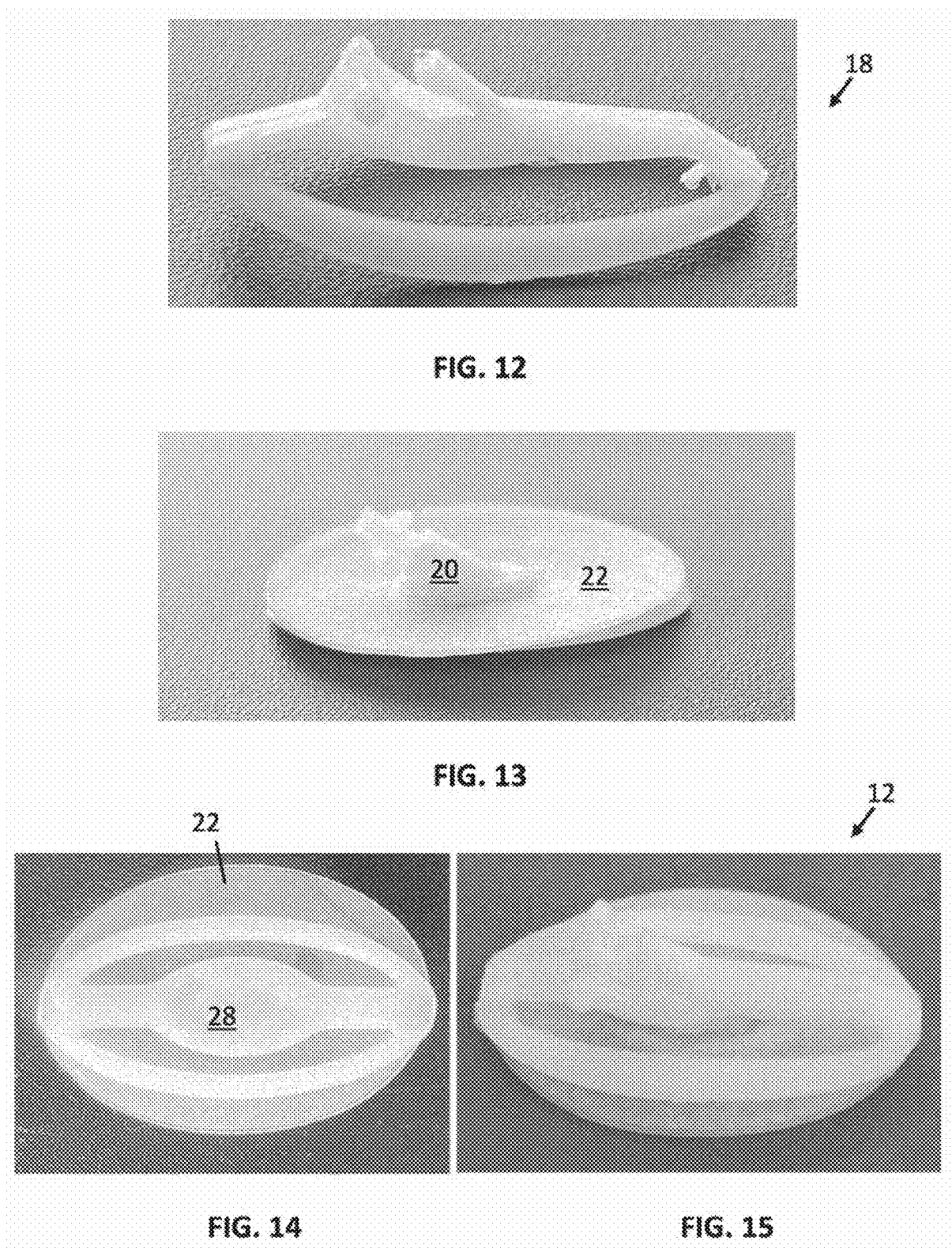
FIG. 12 is a perspective view photograph of an external fixation, according to the present embodiments.
FIG. 13 is a perspective view photograph of a scaffold with a patch disposed thereon, according to the present embodiments.

FIG. 12 is a perspective view photograph of an external fixation 18, according to the present embodiments.

FIG. 13 is a perspective view photograph of a scaffold 20 with a patch 22 disposed thereon, according to the present embodiments.

FIG. 14 is a top view photograph of a scaffold base 28 with a patch 22 disposed thereon, according to the present embodiments.

FIG. 15 is a perspective view photograph of an assembled vascular closure device 12, according to the present embodiments.

Figure 16:
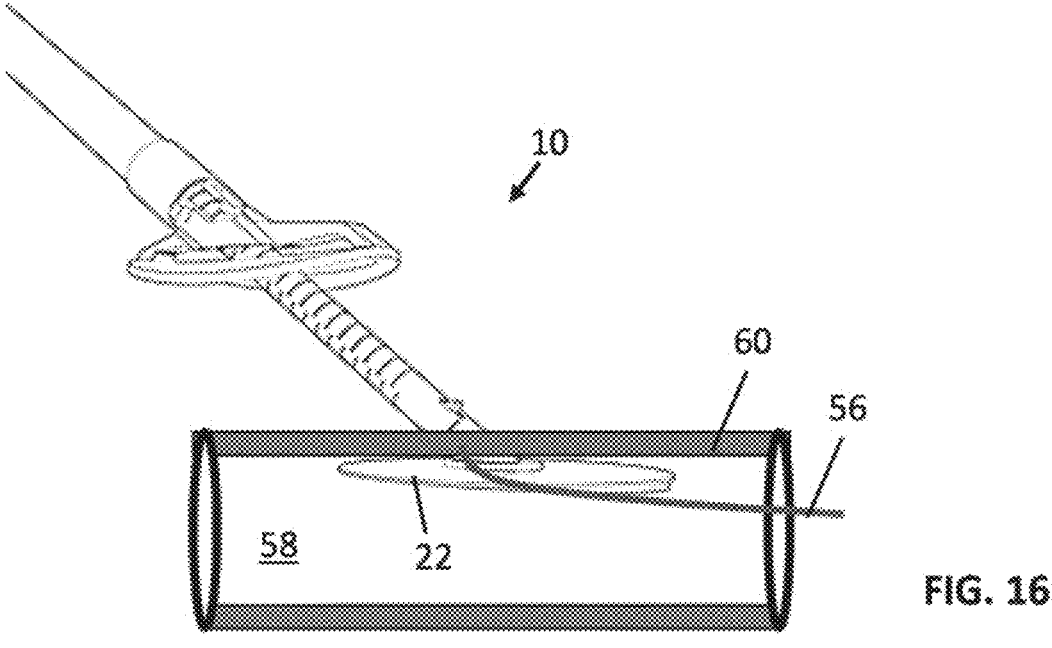
FIG. 16 is a side view of a vascular closure device and system, according to the present embodiments.

FIG. 16 is a side view of a vascular closure device and system 10, according to the present embodiments. The system 10 may include a guidewire 56 for helping to deploy the patch 22 and scaffold 20 within a blood vessel and/or other organ 58. The guidewire 56 may be deployed through each of the patch 22, scaffold (i.e., through the scaffold neck 30) the outer shaft 14, the distal scaffold retention shaft 16, and the external fixation 18). The guidewire 56 may be retracted one the placement of the device 12 has been finalized. As illustrated, each of the patch 22 and scaffold 20 internal to a vessel wall 60, while the external fixation 18 remains external to the vessel wall 60. The scaffold 20 (i.e., the scaffold bas 28) is visible beneath the patch 22 near the guidewire 56 and is unlabeled for clarity purposes.

Figure 17:
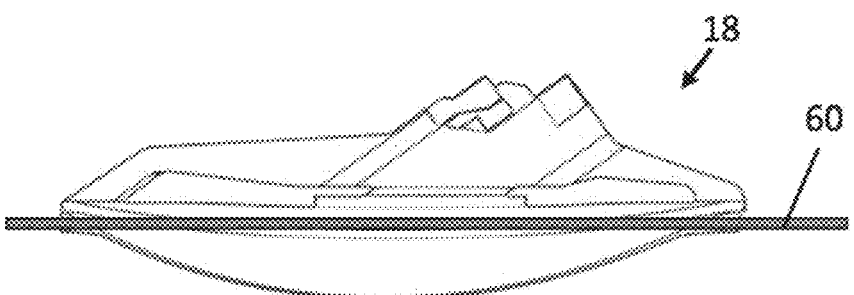
FIG. 17 is a side view of a vascular closure device, according to the present embodiments.

FIG. 17 is a side view of the external fixation 18 when deployed adjacent the vessel wall 60, according to the present embodiments.

Figure 18:
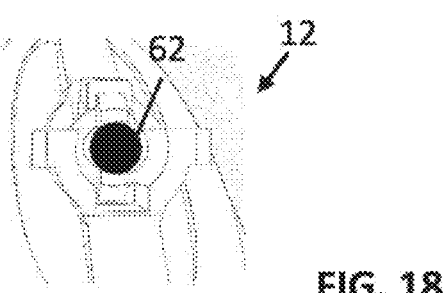
FIG. 18 is a top view of a vascular closure device, according to the present embodiments.

FIG. 18 is a top view of a vascular closure device 12 with a closure pin 62 disposed in the guidewire hole after the guidewire 56 has been retracted, according to the present embodiments. In some embodiments, a guidewire may not be used at all, in which case the closure pin 62 may be disposed within the device 12 throughout deployment.

Figure 19:
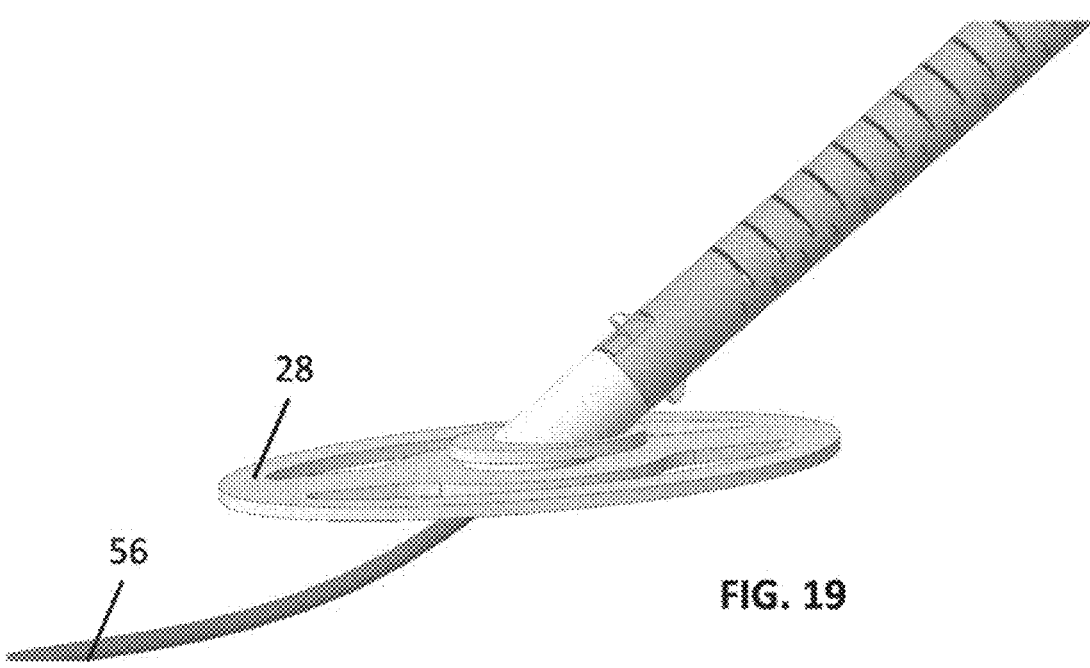
FIG. 19 is a perspective view of a vascular closure device and system, according to the present embodiments.

FIG. 19 is a perspective view of a vascular closure device and system including the scaffold 20 (for example, the scaffold base 28) and guidewire 56, according to the present embodiments. Other components have been omitted for clarity.

Figure 20:
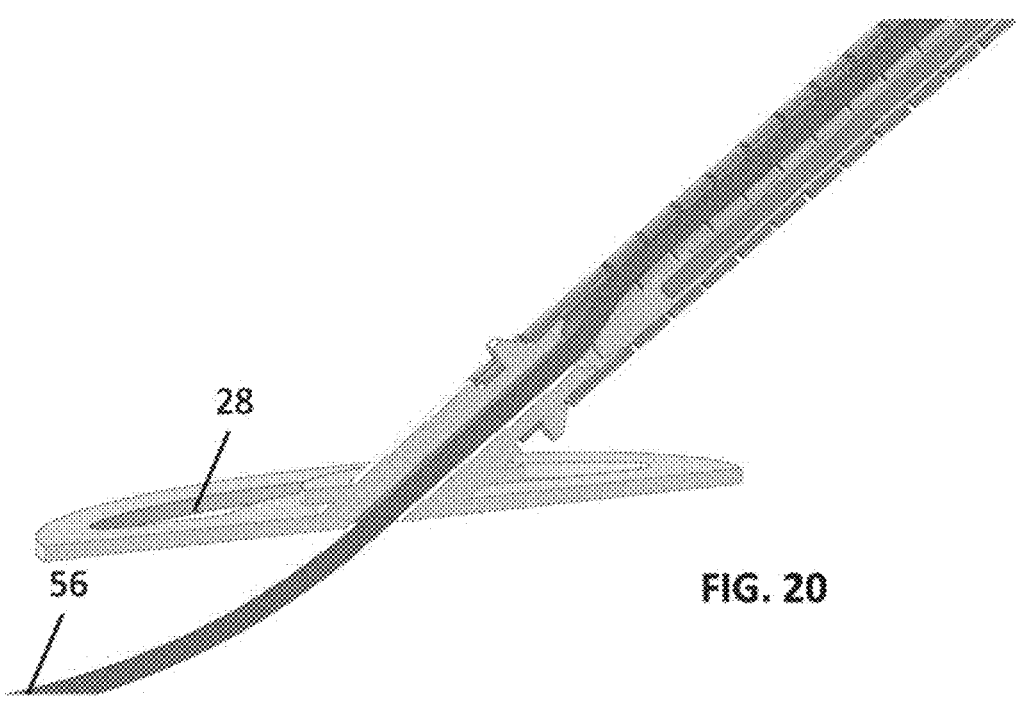
FIG. 20 is a side, cross-sectional view of a vascular closure device and system, according to the present embodiments.

FIG. 20 is a side, cross-sectional view of a vascular closure device and system including the scaffold 20 and guidewire 56, according to the present embodiments. Other components have been omitted for clarity.

Figures 21, 22, 23, 24, 25:
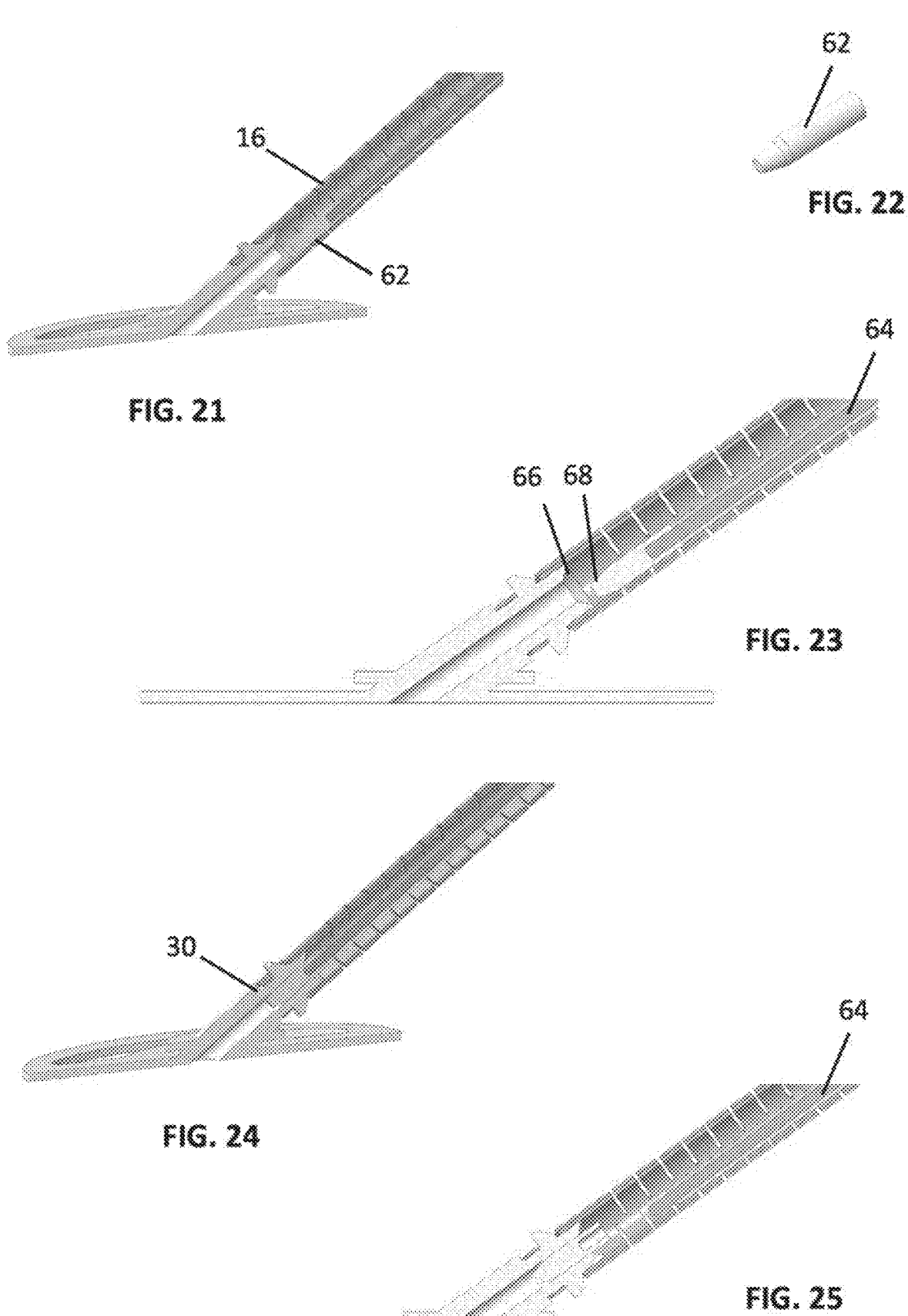
FIG. 21 is a side, cross-sectional view of a vascular closure device and system, according to the present embodiments.
FIG. 22 shows a perspective view of a closure pin, according to the present embodiments.
FIG. 23 is a side, cross-sectional view of a vascular closure device and system, according to the present embodiments.
FIG. 24 is a side, cross-sectional view of a vascular closure device and system, according to the present embodiments.
FIG. 25 is a side, cross-sectional view of a vascular closure device and system, according to the present embodiments.

FIGS. 21 and 23-25 illustrate a side, cross-sectional view of a vascular closure device and system, according to the present embodiments. In FIGS. 21 and 23-25, a closure pin 62 (FIG. 22) is shown being pushed into the center of the scaffold neck 30 by a pusher rod 64, after the guidewire 56 is retracted. The pusher rod 64 may subsequently be retracted, as shown in FIG. 25. While not deployed, each of the pusher rod 64 and closure pin 62 may be stored within the distal scaffold retention shaft 16. The scaffold neck 30 may include an angled inner surface 66 that may interface with an angled closure pin tip 68 to encourage the closure pin to move toward the center of the scaffold neck 30 when being pushed distally by the pusher rod 64 (since, in a stored position, the closure pin 62 and pusher rod 64 are offset from a central axis of the distal scaffold retention shaft 16 to allow space for the guidewire 56). The angle of the angled inner surface 66 may be larger relative to a longitudinal (or central) axis of the distal scaffold retention shaft 16 than the angle of the angled closure pin tip 68 relative to the same.

In operation, each of the patch 22 and scaffold 20 may be folded or wrapped within the outer shaft 14 and the distal scaffold retention shaft 16 such that they may be deployed through the aperture in the vessel wall 60 and within the blood vessel, artery, etc. Once inside the vessel, each of the patch 22 and scaffold 20 may expand. The distal scaffold retention shaft 16 may be pulled proximally to bring the patch 22 and scaffold 20 toward the aperture, thereby sealing the aperture. The outer shaft 14 may be pushed distally such that the external fixation 18 locks with the scaffold 20, thereby forming a solid anchor to which the scaffold and patch may attach on the outside of the vessel wall 60. Each of the outer shaft 14 and the distal scaffold retention shaft 16 may be decoupled from the respective components of the device 12 by a 90-degree clockwise rotation, when looking in the distal direction.

The patch 22 (and optionally the scaffold 20 and/or external fixation) forms, in some embodiments, a flexible bilayer bioabsorbable polymer film which, in some embodiments is electrospun onto a substrate material.

Electrospinning employs, in some embodiments, electrical force to draw very fine fibers (e.g., micro- or nano-scale) of polymers, ceramics, metals, carbon and/or composite materials from a liquid and/or a solution/melt. Electrospinning typically generates a jet in a high-voltage field to produce elongated fibers. A high-voltage electrical field is applied between a capillary where a suitable solution or melt is stored and a collection screen on which an electrically charged jet solidifies. For example, one electrode from a high-voltage source may be contacted with the solution/melt (e.g., needle, capillary) and the other attached to the collection screen. When a voltage is applied to a droplet of the solution/melt, the droplet is stretched into a jet due to electrostatic repulsion and surface tension. The jet is whipped by electrostatic repulsion until it is deposited on the collection screen. Electrospinning can be adjusted to produce continuous liquid jets by controlling parameters (e.g., molecular weight, viscosity, conductivity, surface tension, and electric potential, flow rate, concentration, distance between capillary and collection screen, temperature, needle gauge, etc.). The method beneficially ensures, among other benefits as described herein (e.g., combined with secondary processing (e.g., reduced pressure processing), that no solvent made from the manufacturing process is carried over into the final product. Of course, other methods of generating very fine fibers may be employed.

The mesh layer 102 and/or the substrate 104 comprise, in some embodiments, at least one material selected from the group consisting of Polydioxanone, Poly-L-lactide, Poly-D-lactide, Poly-DL-lactide, Polyglycolide, ε-Caprolactone, Polyethylene glycol, and a copolymer thereof. In some embodiments, the material of the mesh layer 102 and/or substrate layer 104 is a copolymer of, for example, but not limited to, Polydioxanone, Poly-L-lactide, Poly-D-lactide, Poly-DL-lactide, Polyglycolide, ε-Caprolactone, and Polyethylene glycol. In some embodiments, the copolymer includes (a) monomers of Polydioxanone, Poly-L-lactide, Poly-D-lactide, Poly-DL-lactide, Polyglycolide, ε-Caprolactone, or Polyethylene glycol, and (b) one or more additional monomers. In some embodiments, the (a) and (b) monomers form a polymer that is bioabsorbable. One of ordinary skill in the art will appreciate that other bioabsorbable and/or biodegradable material may be employed.

A bioabsorbable polymer can have crystalline and amorphous regions and are therefore, in general, semi-crystalline in nature. Degradation of a bioabsorbable polymer, in certain embodiments, initiates in the amorphous regions, with the crystalline regions degrading at a slower rate relative to the amorphous regions. Without wishing to be tied to a particular theory, and for illustrative purposes only, degradation of a polymer such as Polydioxanone (PDO) occurs along the polymer back bone by hydrolysis of the ester bonds. This non-specific ester bond scission may occur randomly along the polymer chain with water penetration initially breaking the chemical bonds and converting the long polymer chains into natural monomeric acids found in the body, such as lactic acid. Such monomeric acids are then phagocytized by the enzymatic action of special types of mononuclear and multinuclear white blood cells. The polymer is, thus, degraded into non-toxic, low molecular weight residues that are capable of being eliminated from the body by normal metabolic pathways, e.g., via exhalation and/or excretion. Such a pathway thereby enables reference to the breakdown of such polymers in vivo through terminology such as absorbable, bioabsorbable, degradation, biodegradation, resorption, and bioresorption, among others.

In certain embodiments, the patch 22 preferably has a range between about 60 μm and about 120 μm in thickness. The range of thicknesses may be between 50 μm and 500 μm, or between 75 μm and 250 μm, or between 100 μm and 200 μm. In certain embodiments, the electrospun layer 102 substantially consists of fibers in the range from 0.3 μm to 8 μm diameter, with a layer thickness preferably in the range from 10 μm to 60 μm. The fibers may be arranged in a random or patterned orientation.

Figure 26:
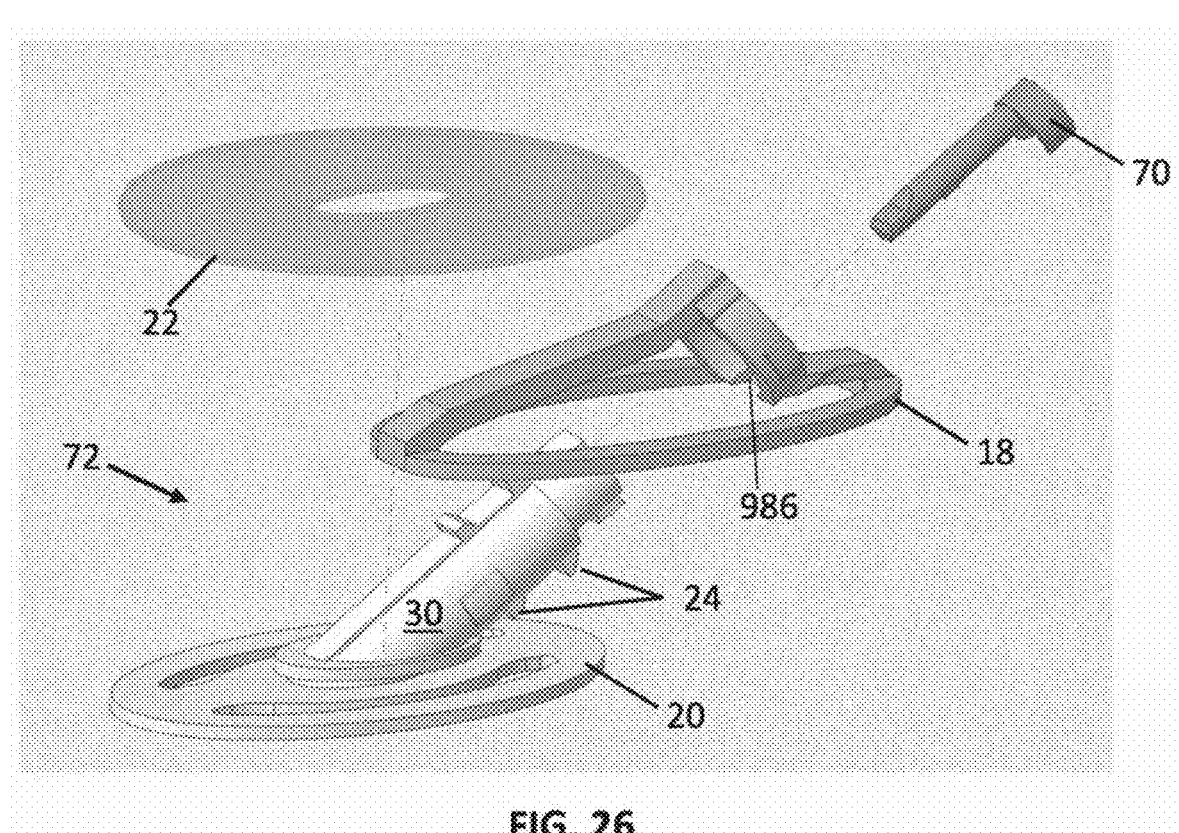
FIG. 26 is a view of a vascular closure device assembly, with the component parts separated, according to the present embodiments.

FIG. 26 is a view of a vascular closure device assembly 72, according to the present embodiments. The vascular closure device assembly 72 includes a closure pin 70, a flexible patch 22, the scaffold (including the scaffold base 20 and scaffold neck 30), and an external fixation 18. In the embodiment of FIG. 26, the device assembly 72 includes two retaining tabs 24 extending out of the scaffold neck 30 on each of the underside and topside of the scaffold neck. The multiple sets of retaining tabs 24 interface with the external fixation 18 such that the external fixation 18 may be fixed around the scaffold neck 30, and on the top of the flexible patch 22, to keep the assembly 72 sandwiched together for sealing a vascular aperture or opening. The multiple sets of retaining tabs 24 allow the assembly 72 to accommodate multiple vessel wall thicknesses and varying anatomies.

Figure 27:
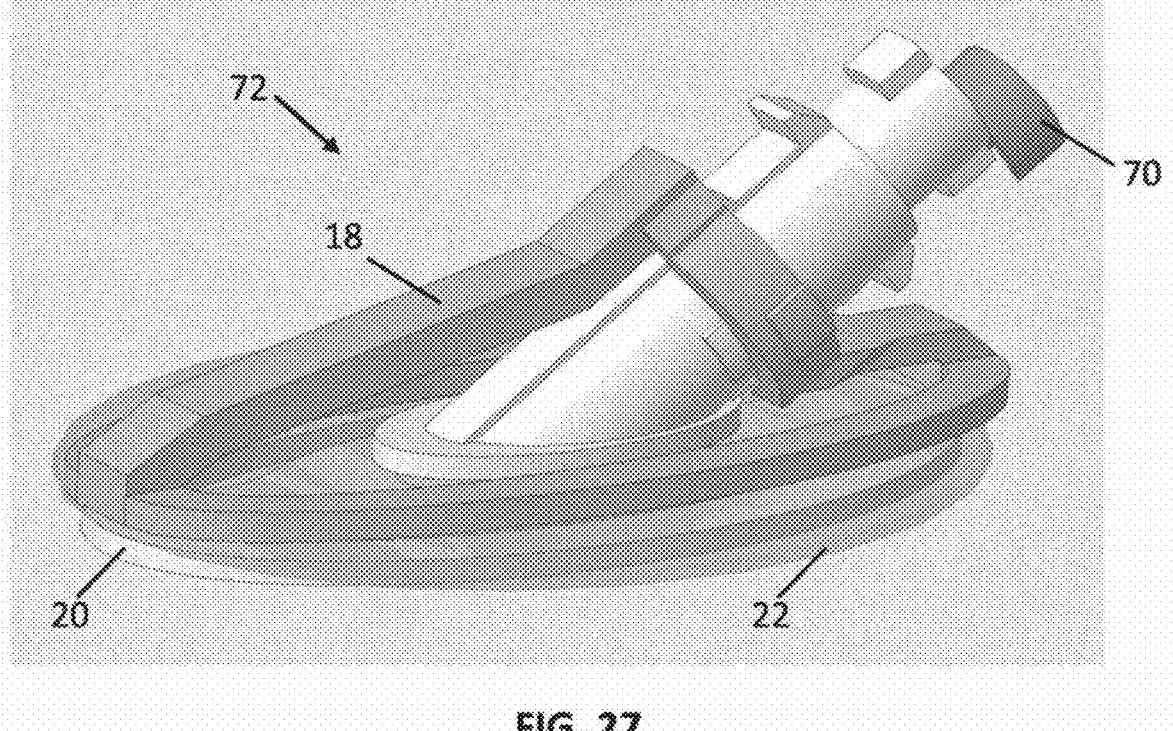
FIG. 27 is a view of a vascular closure device assembly, with the component parts assembled, according to the present embodiments.

FIG. 27 is a view of a vascular closure device assembly 72, according to the present embodiments. The scaffold neck 30 has two retaining tabs 24 for adjusting the distance between the distal edge of the external fixation 18 and the top surface of the scaffold base 20/patch 22. In the embodiment of FIG. 27, the vascular closure device assembly 72 is fully assembled with the external fixation 18 positioned in the tighter configuration, so as to accommodate a thinner tissue thickness. FIGS. 89-92 show additional embodiments and configurations that include a device with four different sets of teeth protruding from the scaffold neck 30, 122, thereby allowing the device to accommodate 4 different vessel wall thicknesses and different tissue tract anatomies. As shown in FIGS. 26 and 27, and as described in greater detail below in connection with FIGS. 46-77, the closure pin 70 may be used to close (that is, seal) a guidewire lumen after the guidewire is withdrawn from the scaffold.

Figures 28, 29, 30:
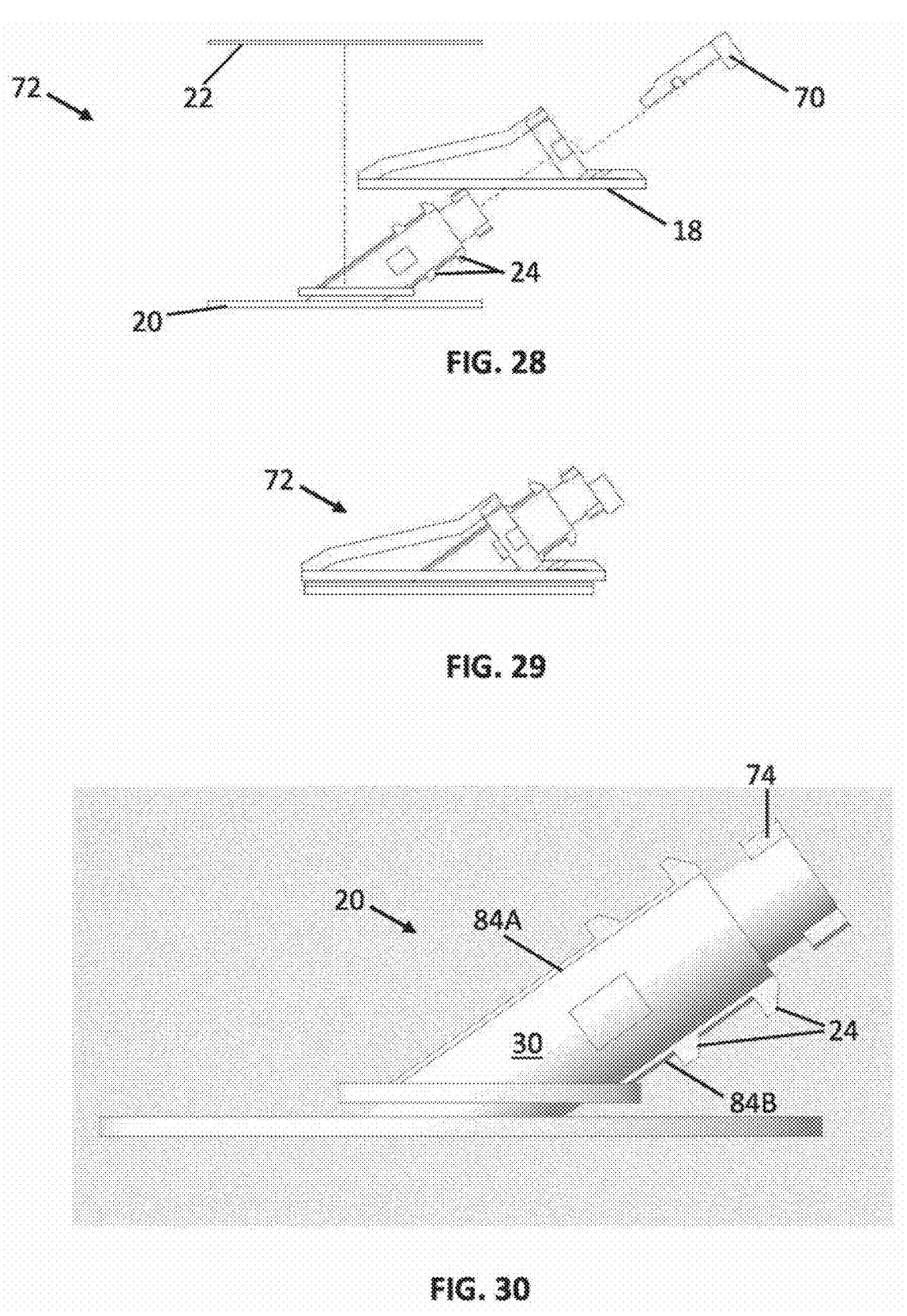
FIG. 28 is a side view of a vascular closure device assembly, with the component parts separated, according to the present embodiments.
FIG. 29 is a side view of a vascular closure device assembly, with the component parts assembled, according to the present embodiments.
FIG. 30 is a side view of a vascular closure device scaffold, according to the present embodiments.

FIGS. 28 and 29 show alternate side views of the unassembled and fully assembled vascular closure device assembly 72, according to the present embodiments. The device assembly configuration of FIGS. 28 and 29 is the same as that of FIGS. 26 and 27.

Figure 31:
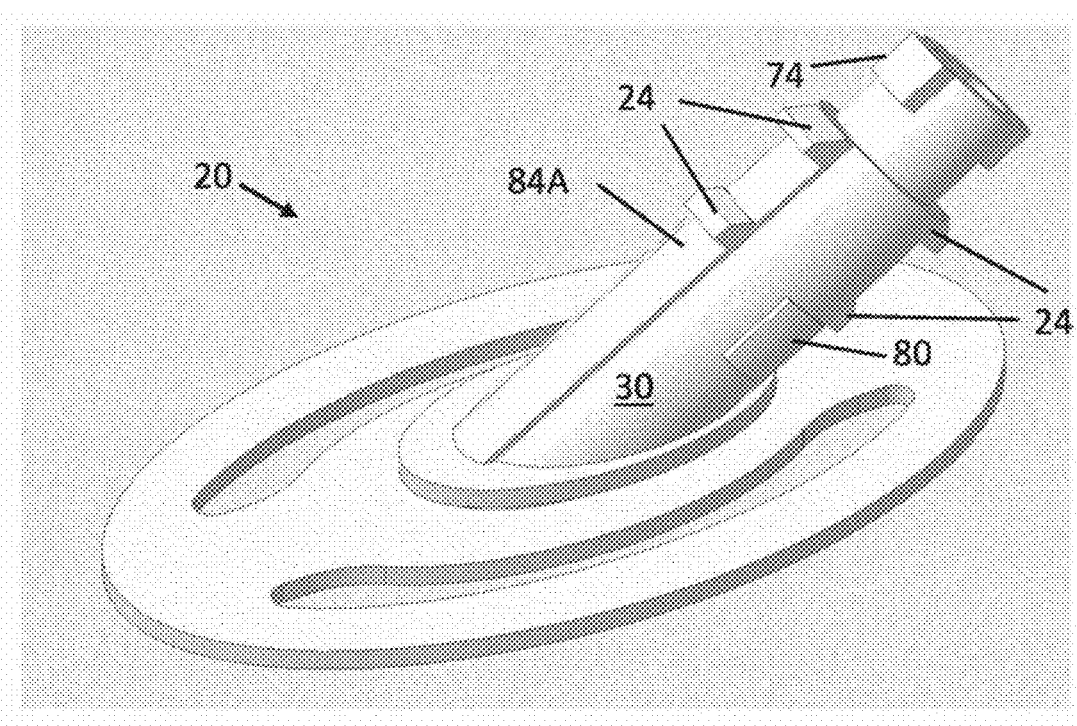
FIG. 31 is a perspective view of a vascular closure device scaffold, according to the present embodiments.
Figure 32:
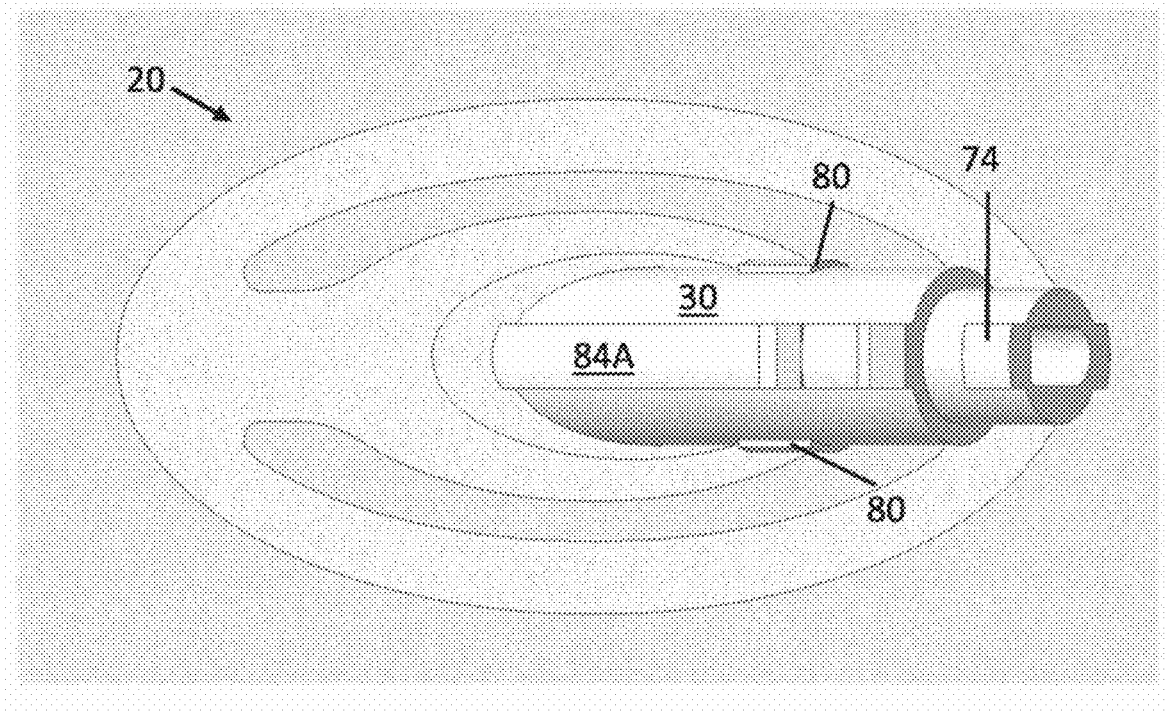
FIG. 32 is a top view of a vascular closure device scaffold, according to the present embodiments.
Figures 33, 34:
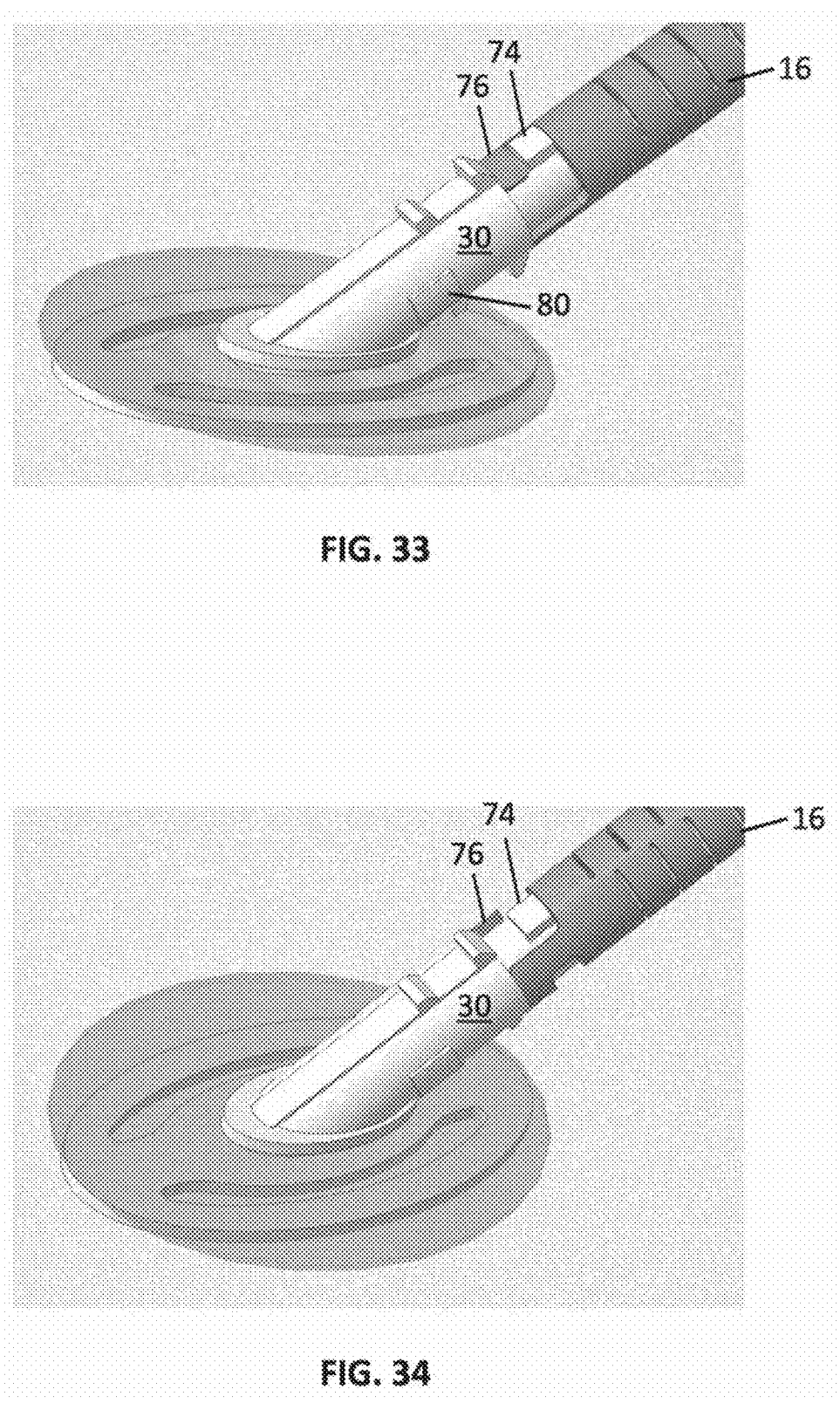
FIG. 33 is a view of a vascular closure device and delivery shaft, according to the present embodiments.
FIG. 34 is a view of a vascular closure device and delivery shaft, according to the present embodiments.

FIGS. 30-32 illustrate side, perspective, and top views of a vascular closure device scaffold 20, according to the present embodiments. The embodiment of FIG. 30 includes two sets of retaining tabs 24. In addition, the scaffold 20 includes a first linear ridge 84A on the top side of the scaffold neck and a second linear ridge 84B on the bottom side of the scaffold neck 30. The first and second linear ridges 84A, 84B interface with corresponding grooves 986 (shown in FIGS. 26, 39, and 87) in the external fixation 18 such that the external fixation 18 remains properly aligned (i.e., with the scaffold base 20 and flexible patch 22) as it slides distally down the scaffold neck 30. The grooves 986 are disposed within an internal surface of the collar 984 on opposing sides. The scaffold 20 may also include a set of raised tabs 74 disposed on opposite sides of the proximal end of the scaffold neck 30. In some embodiments, the raised tabs 74 may be substantially square-shaped. The raised tabs 74 interface with L-shaped slots 76 in the scaffold retention shaft 16, thereby forming a bayonet mount, as shown in FIGS. 33 and 34, which illustrate views of a vascular closure device and delivery shaft (scaffold retention shaft 16). In the configuration of FIG. 33, the L-shaped slot 76 is positioned distally from the raised tab 74 when the scaffold 20 is in delivery position, thereby preventing distal or proximal movement of the scaffold 20 relative to the scaffold retention shaft 16. In the configuration of FIG. 34, the L-shaped slot 76 has been rotated (that is, the entire scaffold retention shaft 16 has been rotated) relative to the scaffold 20, such that the L-shaped slot 76 is no longer positioned distal of the raised tab 74. In the position shown in FIG. 34, the scaffold retention shaft 16 may disengage with the scaffold 20 and may be withdrawn in a proximal direction, once the scaffold has been positioned about the wound, aperture, and/or vessel opening.

Figures 35, 36, 37:
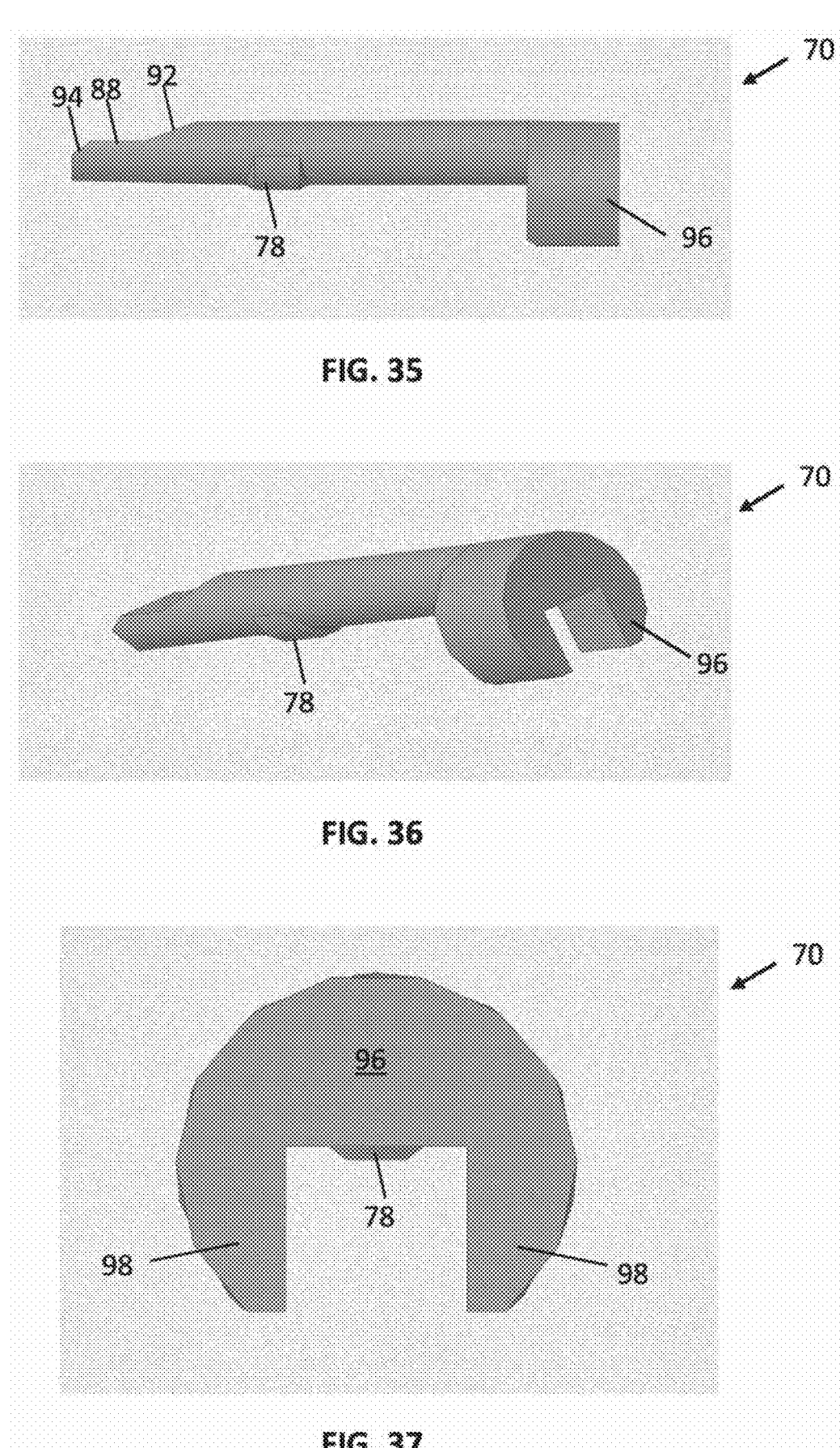
FIG. 35 is a side view of a vascular closure device pin, according to the present embodiments.
FIG. 36 is a perspective view of a vascular closure device pin, according to the present embodiments.
FIG. 37 is a back view of a vascular closure device pin, according to the present embodiments.

FIGS. 35-37 illustrate side, perspective, and front views of a vascular closure device closure pin 70, according to the present embodiments. The closure pin 70 may include an outer diameter of from about 0.03 inches to about 0.035 inches (for example, in a range from 0.031 inches to 0.034 inches, or 0.032 inches to 0.033 inches) such that it may be used to seal or close a guidewire lumen with an inner diameter of about 0.035 inches. The closure pin 70 may include a stepped tapered shape at the distal end with a stepped portion 88 located distally of a tapered portion 92. The closure pin 70 may also include a chamfer 94 located distally of the stepped portion 88. The stepped tapered shape allows the closure pin 70 to interface with internal tapers and/or features of the scaffold neck 30 to encourage the closure pin 70 to slide into the guidewire lumen when pushed distally, as illustrated in further detail in FIGS. 52 and 53.

Referring still to FIGS. 35-37, the closure pin 70 may also include at least one bump feature 78 which provides a wedging effect when the closure pin 70 is driven distally into the guidewire lumen (or hole) in the scaffold neck 30. The bump feature 78 provides additional friction and interference between the closure pin 70 and the internal surface of the guidewire lumen, thereby creating a compression fit therebetween when the closure pin 70 is pushed distally. The closure pin 70 also includes a head section 96 with a larger cross-sectional area than the rest of the closure pin 70, thereby helping to facilitate the closure pin 70 to be driven into the guidewire lumen via a push tube (not shown). The closure pin may also include two curved arms 98 that are part of the pin head section 96 and wrap around the guidewire 56 (and allow the guidewire 56 (shown in FIG. 16) to be withdrawn therethrough).

Figures 38, 39, 40:
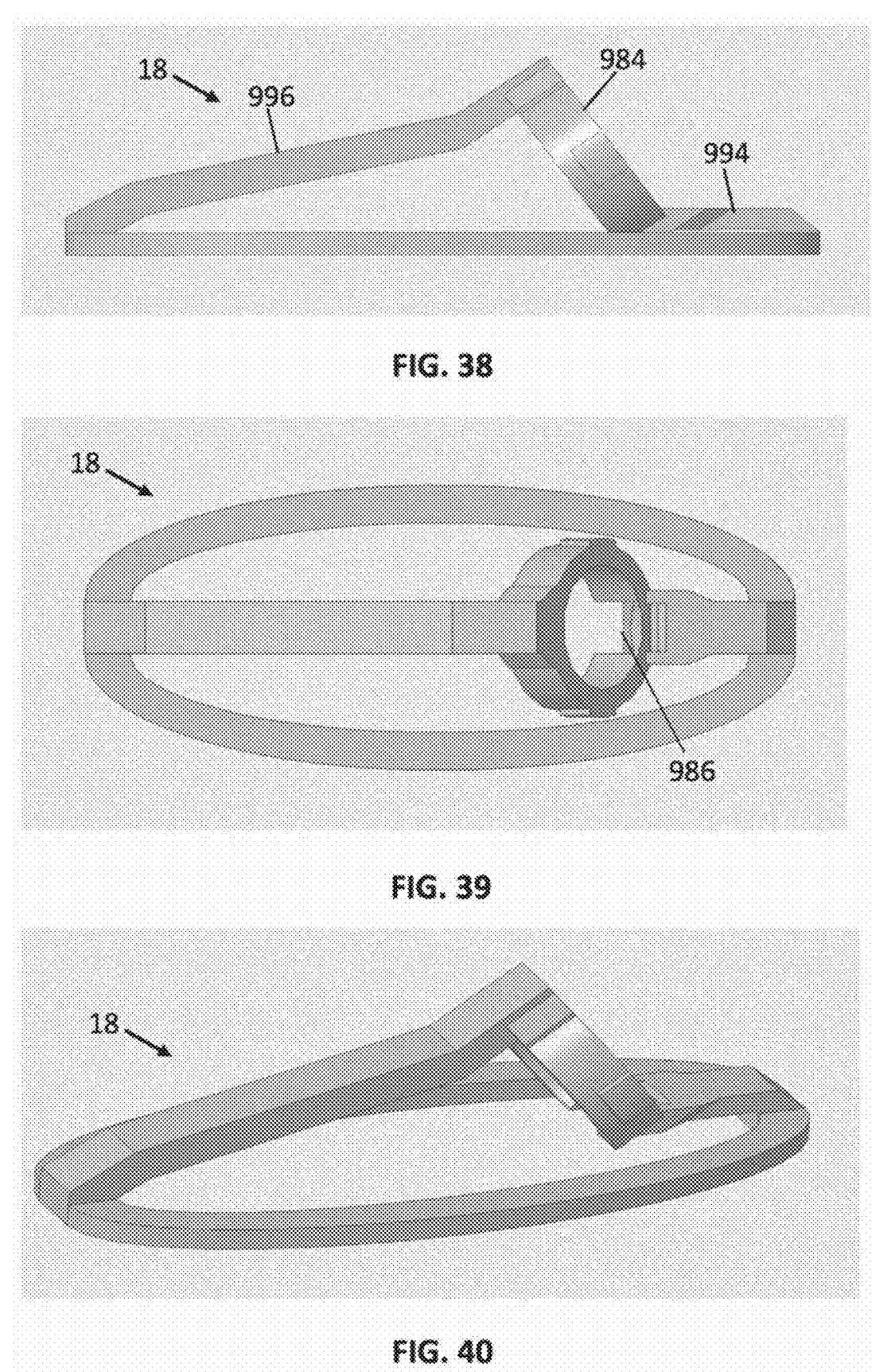
FIG. 38 is a side view of a vascular closure device external fixation, according to the present embodiments.
FIG. 39 is a top view of a vascular closure device external fixation, according to the present embodiments.
FIG. 40 is a perspective view of a vascular closure device external fixation, according to the present embodiments.
Figures 86, 87:
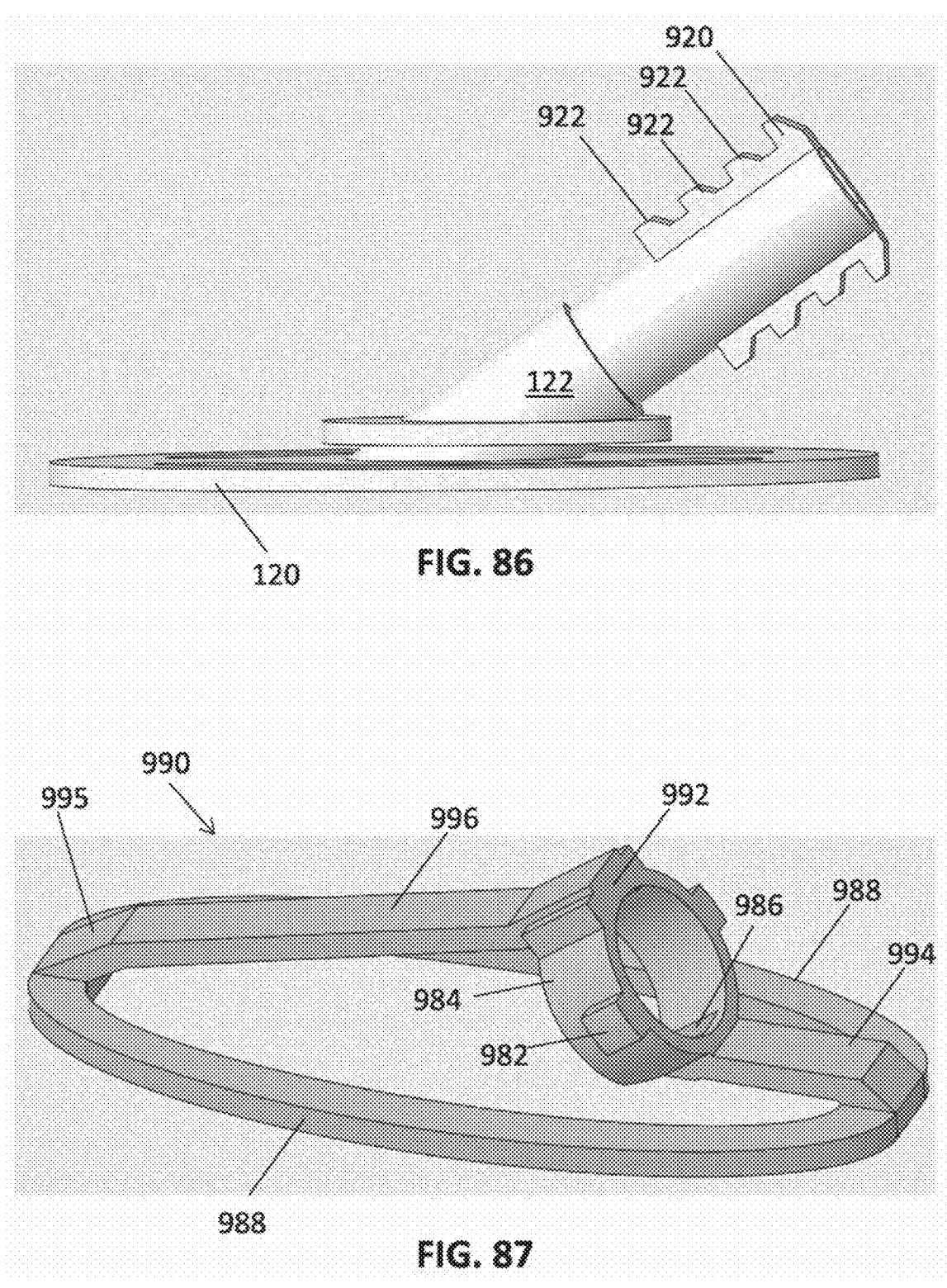
FIG. 86 illustrates an image of a scaffold used for a closure device, according to aspects of the present embodiments.
FIG. 87 illustrates an image of an external fixation used for a closure device, according to aspects of the present embodiments.

FIGS. 38-40 illustrate side, top, and perspective views of a vascular closure device external lock 18 (or external fixation 18), according to the present embodiments. The external fixation 18 may include anterior and posterior members 996, 994 or ribs connecting to the collar 984 to provide both support and flexibility such that the ribs 996, 994 may adapt and conform to the various vessel wall morphologies and tissue tract anatomies that are experienced in clinical use. The external fixation 18 is also shown in FIG. 87 and described in further detail below.

Figure 41:
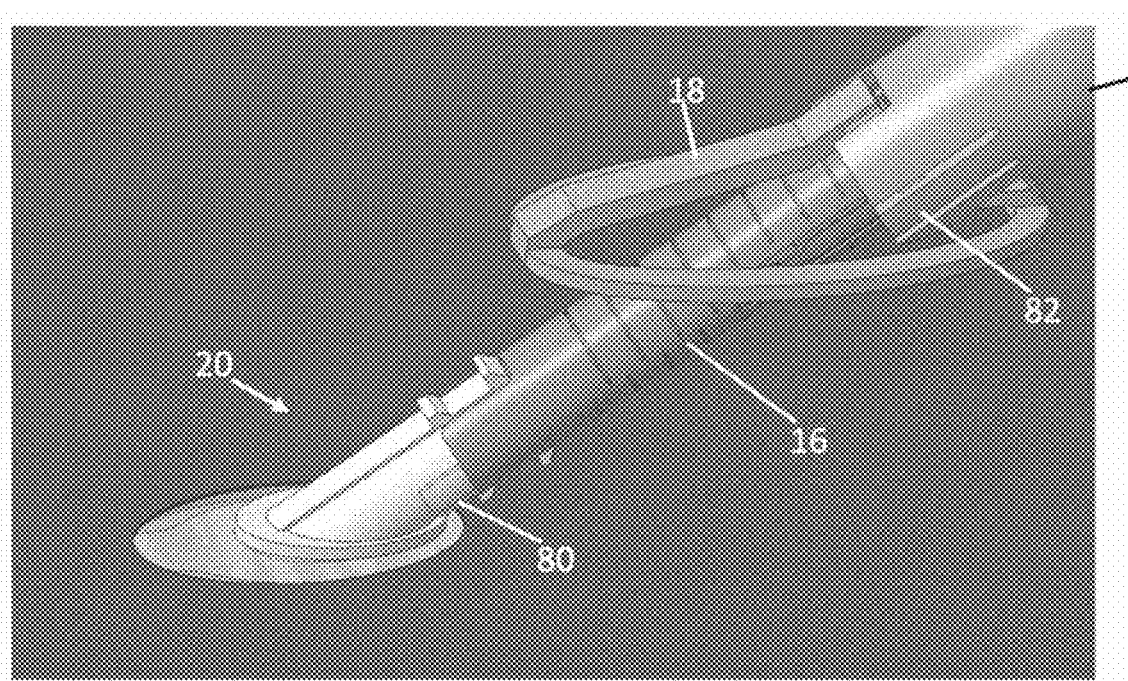
FIG. 41 is a view of a vascular closure device and delivery system, according to the present embodiments.
Figure 42:
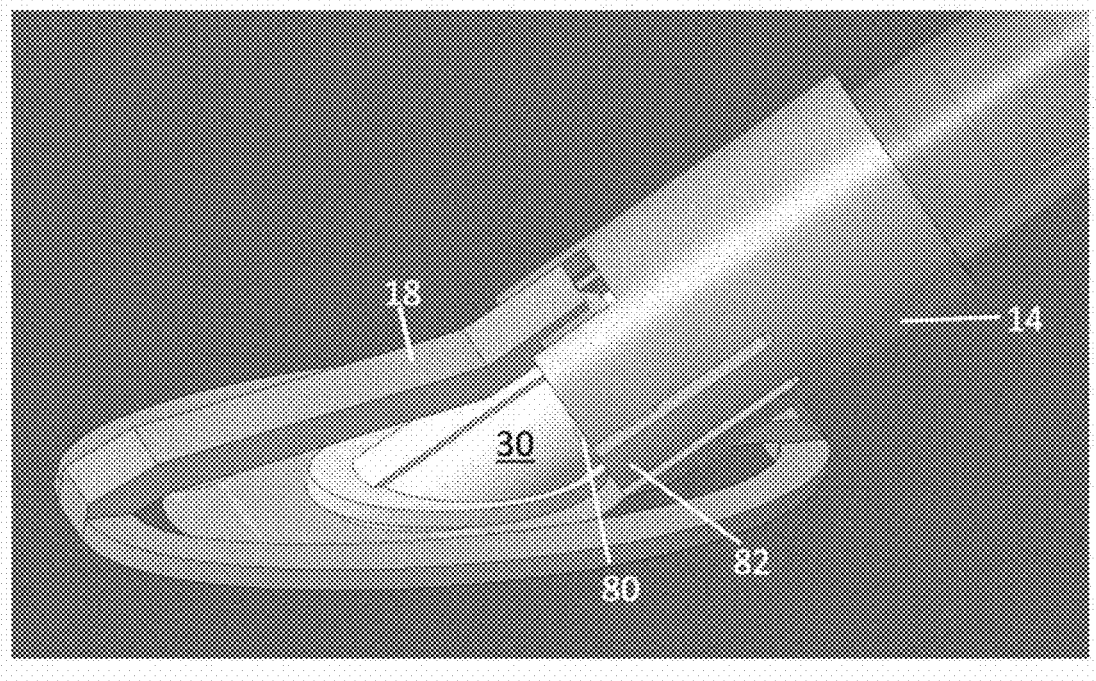
FIG. 42 is a view of a vascular closure device and delivery system, according to the present embodiments.
Figures 43, 44, 45:
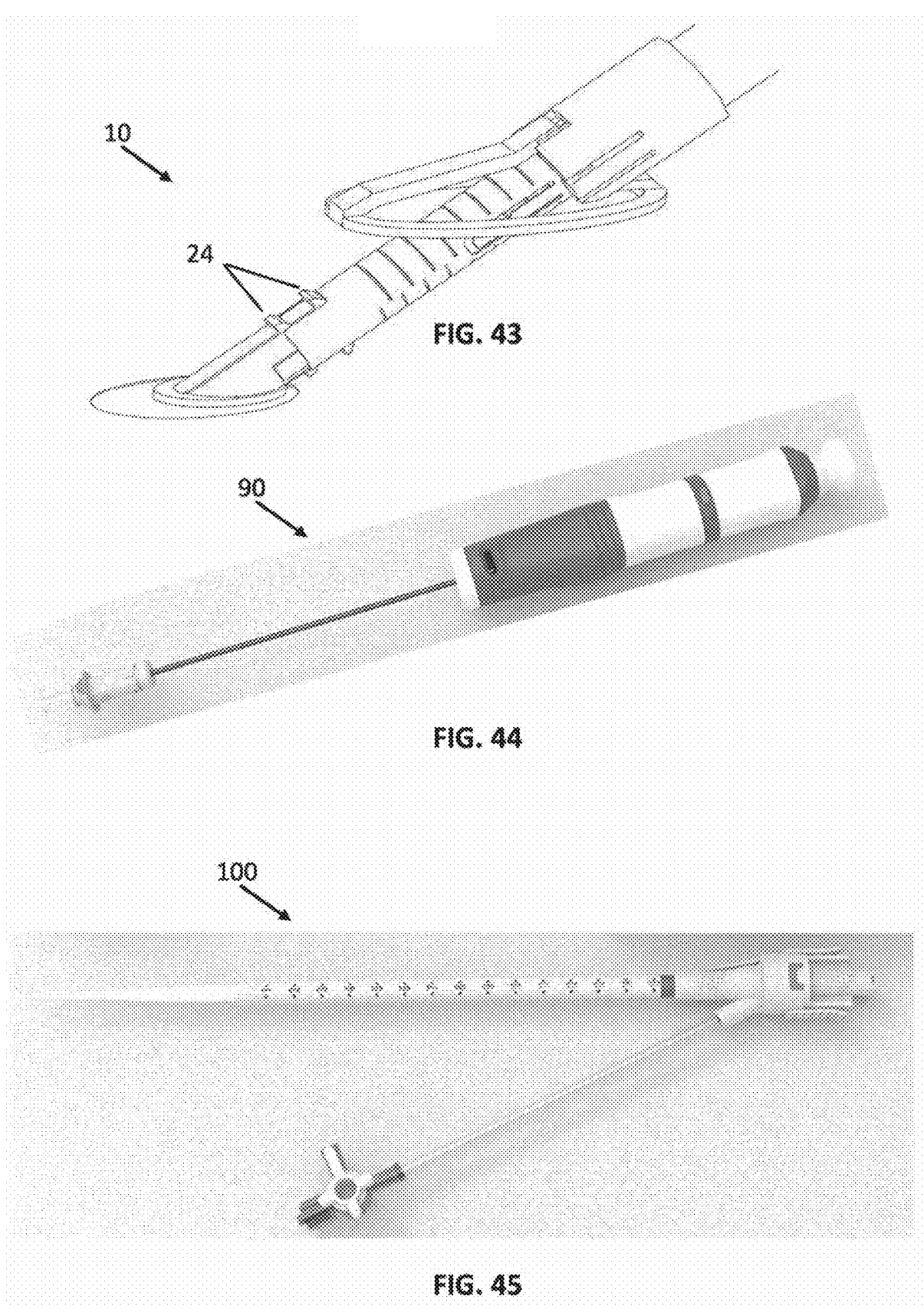
FIG. 43 is a view of a vascular closure device delivery system and device, according to the present embodiments.
FIG. 44 is a view of a vascular closure device delivery system and handle, according to the present embodiments.
FIG. 45 is a view of a vascular closure device introducer, according to the present embodiments.

FIGS. 41-43 illustrate views of a vascular closure device and delivery system, according to the present embodiments. In the embodiments of FIGS. 41 and 42, the external fixation 18 is being delivered to the scaffold 20 via an outer shaft that is concentrically disposed around the scaffold retention shaft 16, and coupled to the external fixation 18. In FIG. 41, the external fixation 18 is coupled to the outer shaft 14 via a pair of retention clips 82 on opposing lateral sides of the outer shaft 14 such that the external fixation 18 may be pushed distally toward the scaffold 20. The retention clips 82 are monolithic with the outer shaft 14 and extend axially toward the distal end of the outer shaft 14 such that the distal ends of the retention clips 82 are free to bend and flex, with inherent stiffness and elasticity. Internal, radially-inwardly-extending lips (not shown) at the distal ends of the retention clips 82 interface with the underside (or distal surface of) the collar 984, thereby holding the external fixation 18 in place. As illustrated in FIG. 42, once the external fixation 18 is brought around the scaffold neck 30, the retention clips 82 of the outer shaft 14 interface with a corresponding pair of raised tabs 80 on the scaffold neck 30 that push the retention clips 82 radially outward, thereby causing them to release the external fixation 18 (and allowing the outer shaft 14 to decouple from the external fixation 18 and be proximally withdrawn). By this point, the collar 984 has been pushed around and past at least one set retaining tabs 24 (depending on the vessel wall thickness), such that the external fixation 18 will remain sandwiched against the patch 22 and scaffold base 20. In FIG. 42, a portion of the outer shaft 14 appears as translucent such that the scaffold retention shaft 16 therewithin is visible.

FIG. 44 is a view of a vascular closure device introducer 90, according to the present embodiments. FIG. 45 is a view of a vascular closure device and system 100, according to the present embodiments.

Guidewire Lumen Closure

First Embodiment of Closure Pin

Figures 46, 47:
FIG. 46 illustrates an image of a closure device with a guidewire lumen closure pin, according to aspects of the present embodiments.
FIG. 47 illustrates an image of a closure device with a guidewire lumen closure pin, according to aspects of the present embodiments.
Figures 48, 49:
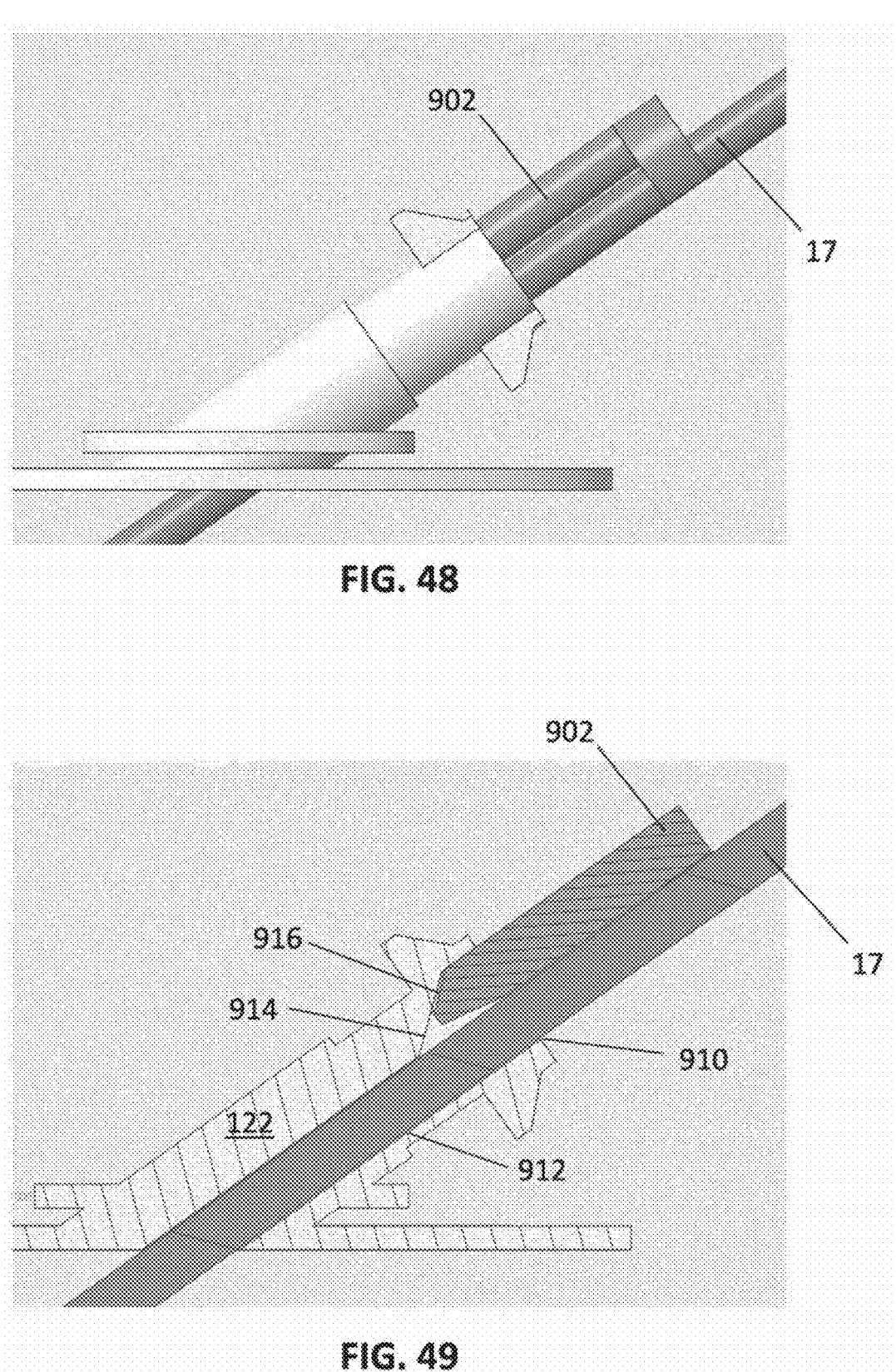
FIG. 48 illustrates an image of a closure device with a guidewire lumen closure pin, according to aspects of the present embodiments.
FIG. 49 illustrates an image of a closure device with a guidewire lumen closure pin, according to aspects of the present embodiments.
Figures 50, 51:
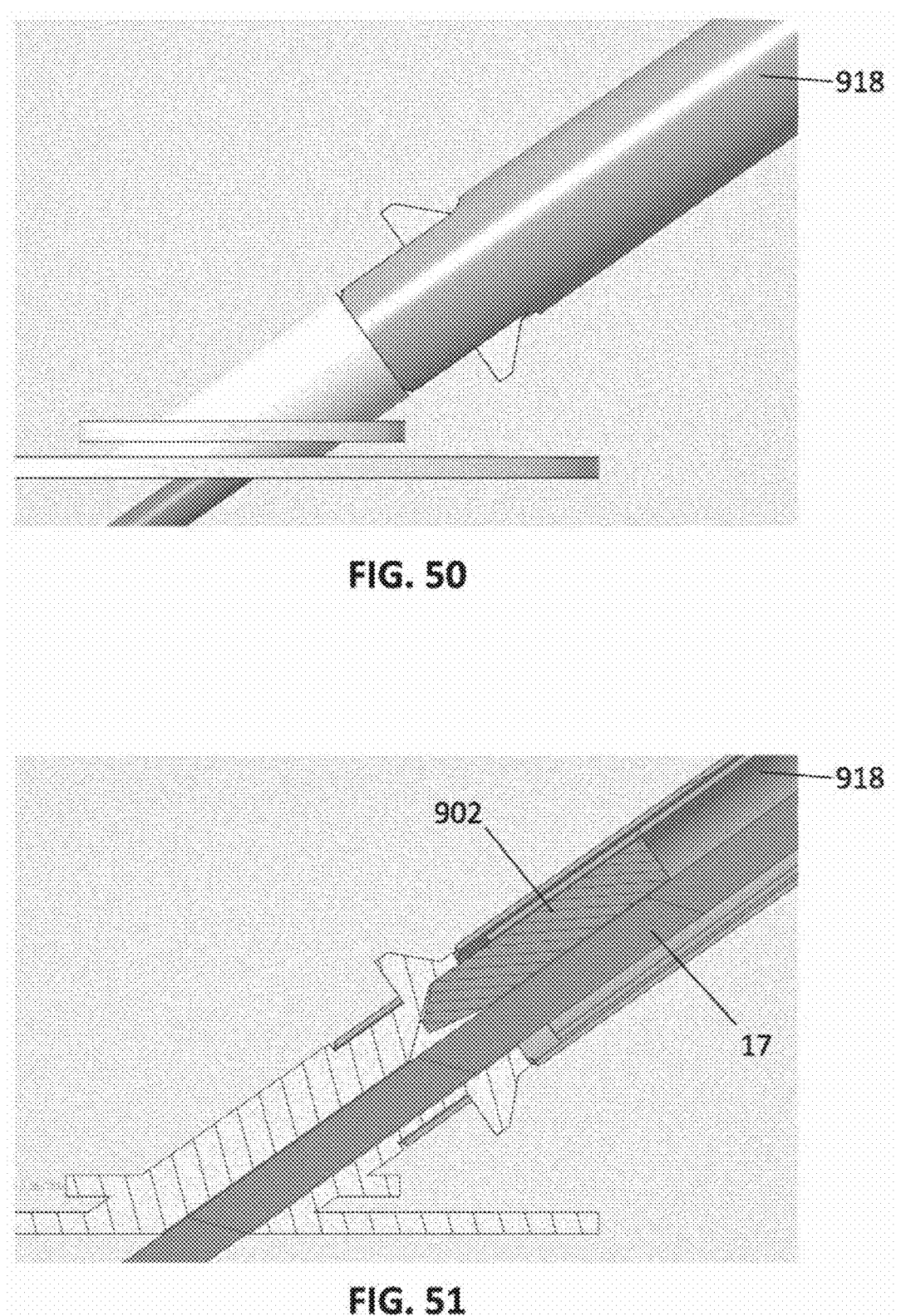
FIG. 50 illustrates an image of a closure device with a guidewire lumen closure pin, according to aspects of the present embodiments.
FIG. 51 illustrates an image of a closure device with a guidewire lumen closure pin, according to aspects of the present embodiments.

FIGS. 46-57 illustrate images of a first embodiment of a closure device 100 with a first embodiment of a guidewire lumen closure pin 902, according to aspects of the present embodiments. As shown in FIG. 46, the device 100 includes a closure pin 902 disposed adjacent to, and in contact with, the guidewire 17. The closure pin 902 may include a generally circular or cylindrical pin head 904, as well as two curved arms 906 that are part of the pin head 904 and wrap around the guidewire 17. In use, the closure pin 902 and/or the guidewire 17 may be slidably disposed within a mouth 910 disposed within the scaffold neck 122, which extends at an angle from the base 120 (i.e., the scaffold base). The scaffold neck 122 may include two retaining tabs 908 disposed on opposite sides of the scaffold neck 122, approximately 180 degrees apart. FIGS. 47 and 48 illustrate other views of the device 100 including the closure pin 902 and guidewire 17. FIG. 49 illustrates a cross section of the guidewire 17 and closure pin 902 inserted into the mouth 910, with the guidewire 17 also disposed within a guidewire lumen 912, the guidewire lumen 912 being disposed all the way through the scaffold neck 122. At a transition between the guidewire lumen 912 and the mouth 910, the scaffold neck 122 may include an internal taper 914 that angles radially inward and interfaces with a corresponding angled tip 916 of the closure pin 902, such that the internal taper 914 pushes the closure pin 902 toward (and into) the guidewire lumen 912 when the closure pin 902 is pushed distally into the mouth 910 (i.e., after the guidewire 17 is removed from the guidewire lumen 912). In some embodiments, the angle of the internal taper 914 and the angled tip 916 may be complementary (for example 30 degrees and 60 degrees, 45 degrees and 45 degrees, or 60 degrees and 30 degrees, respectively, relative to a longitudinal axis of the scaffold neck 122 and/or guidewire lumen 912).

Figures 52, 53:
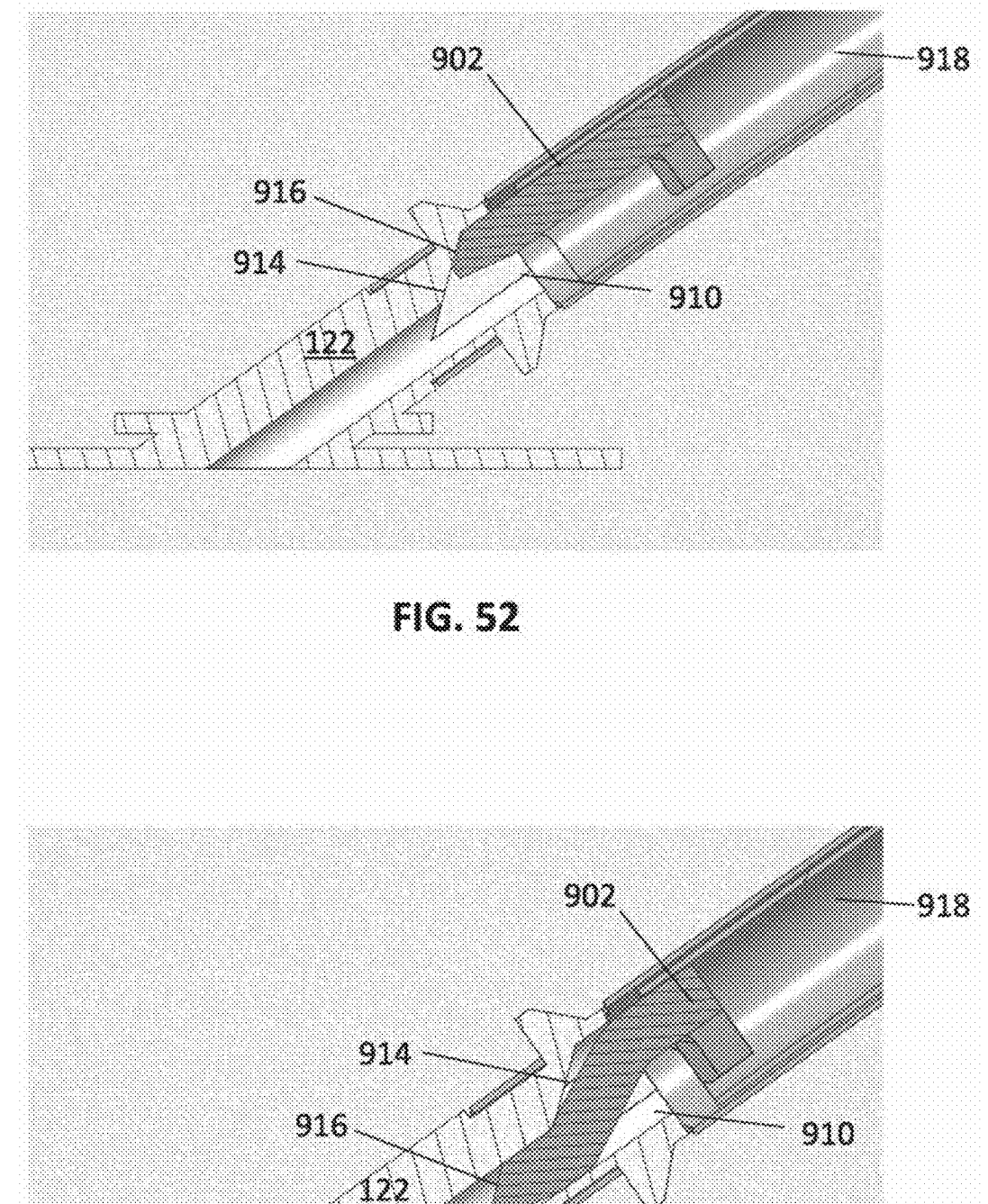
FIG. 52 illustrates an image of a closure device with a guidewire lumen closure pin, according to aspects of the present embodiments.
FIG. 53 illustrates an image of a closure device with a guidewire lumen closure pin, according to aspects of the present embodiments.

FIGS. 50-54 illustrate images of the first embodiment of a closure device 100 with a guidewire lumen closure pin 902 including external and/or cross-sectional views of the delivery shaft 918, according to aspects of the present embodiments. FIG. 52 illustrates the closure pin 902 with the angled tip 918 disposed within the mouth 910 after the guidewire 17 has been removed from the scaffold neck 122. As the closure pin 902 is pushed farther into the scaffold neck 122, the internal taper 914 pushes the angled tip 916 of the closure pin 902 into the guidewire lumen 912, as shown in FIG. 53, thereby closing the guidewire lumen 912 and sealing the closure site. The closure pin 902 and guidewire 17 may be approximately the same diameter (for example 0.035 inches (35 mils) (or from about 0.025 inches to about 0.04 inches, or from about 0.015 inches to about 0.05 inches) such that each may move within the guidewire lumen 912 with a slight clearance that does not allow blood to flow past (i.e., in the very small annulus between the outer surface of the closure pin 902 and/or guidewire 17 and the inner surface of the guidewire lumen 912).

Figures 54, 55:
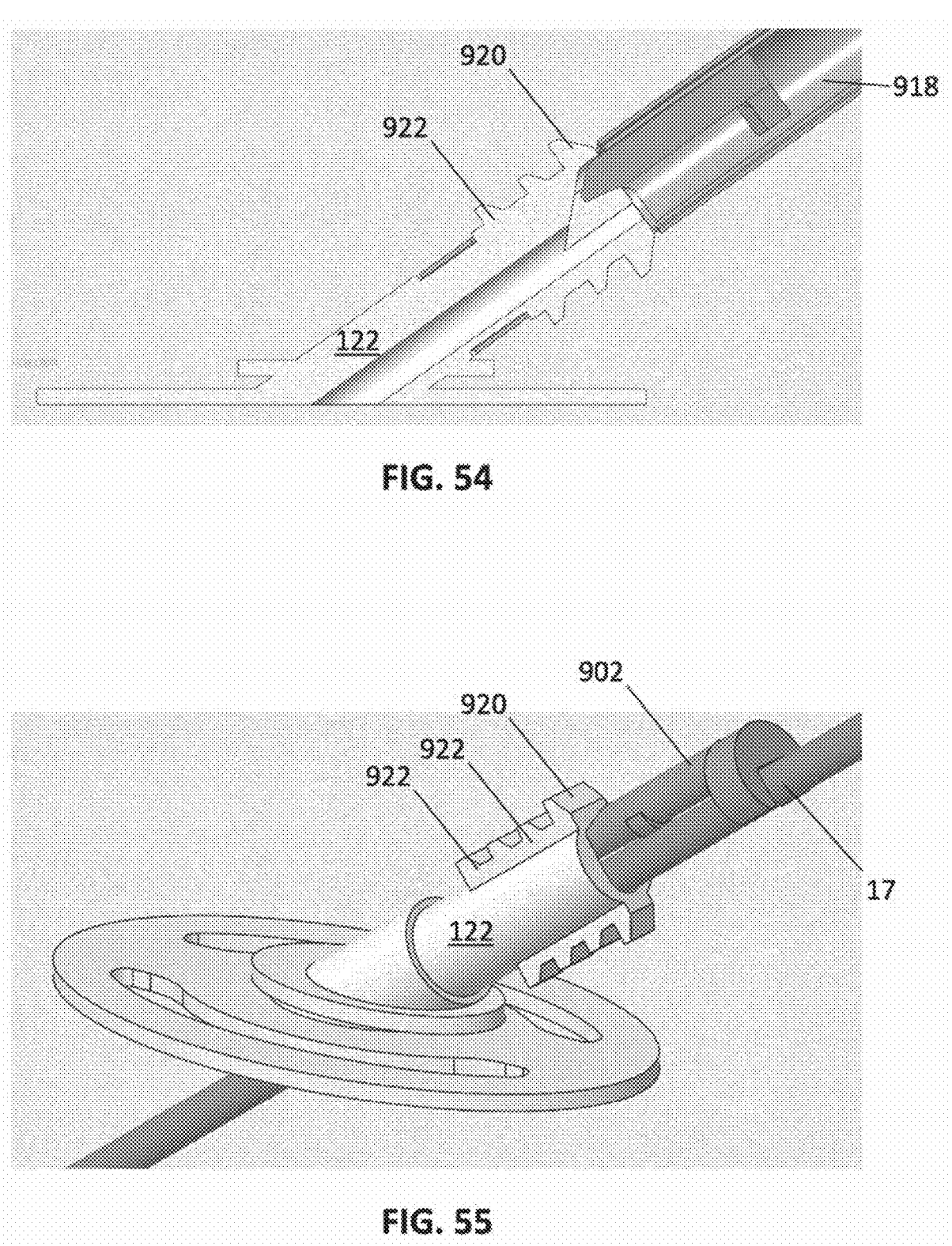
FIG. 54 illustrates an image of a closure device with a guidewire lumen closure pin, according to aspects of the present embodiments.
FIG. 55 illustrates an image of a closure device with a guidewire lumen closure pin, according to aspects of the present embodiments.
Figures 56, 57:
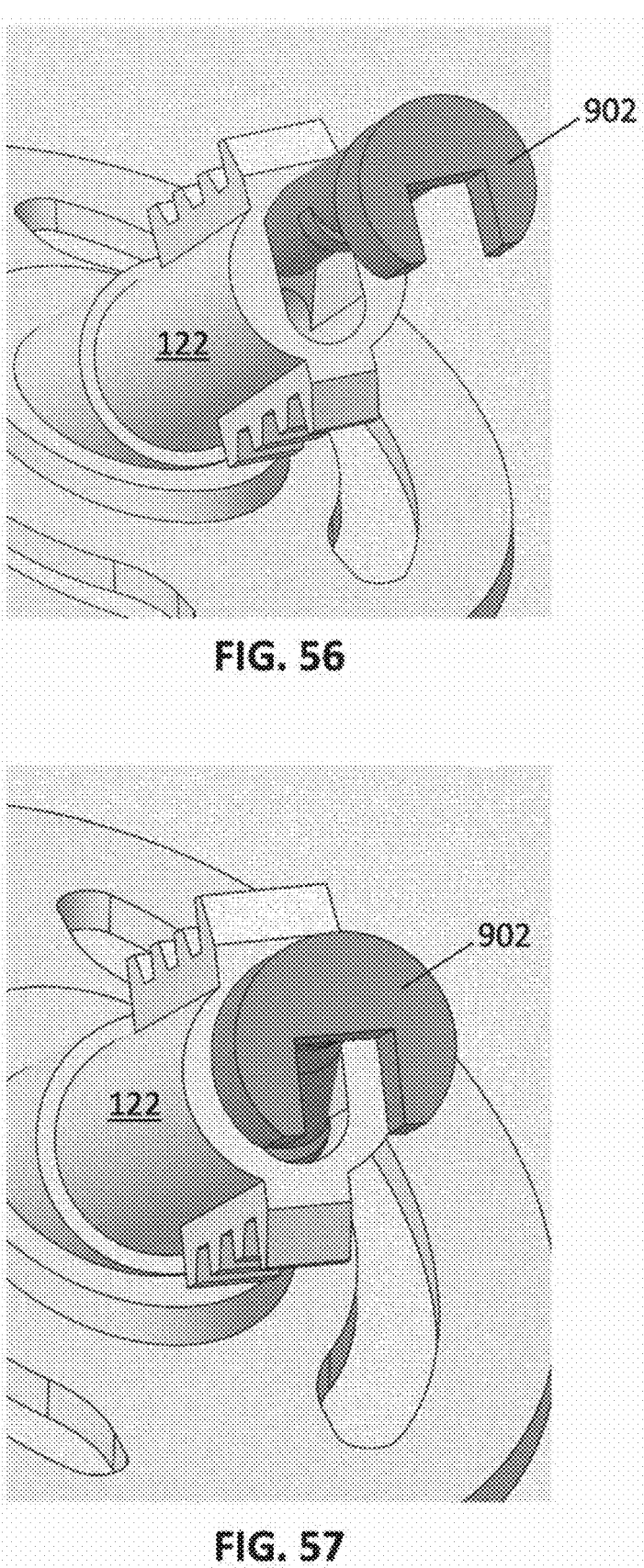
FIG. 56 illustrates an image of a closure device with a guidewire lumen closure pin, according to aspects of the present embodiments.
FIG. 57 illustrates an image of a closure device with a guidewire lumen closure pin, according to aspects of the present embodiments.

FIGS. 54 and 55 illustrate images of the closure device 100 with the first embodiment of the guidewire lumen closure pin 902, according to aspects of the present embodiments. In the embodiments illustrated in FIGS. 54 and 55, the device 100 includes 3 sets and 4 sets of retaining tabs 920, 922, respectively. In FIG. 54, the device includes a first set of retaining tabs 920 located at a proximal-most end of the scaffold neck 122, as well as two additional sets (i.e., pairs) of retaining tabs 922 located distally from the first pair of retaining tabs 920. In some embodiments, the first pair of retaining tabs 920 may be larger than each of the second, third, and fourth pairs (in the embodiment of FIG. 55) of retaining tabs 922. Each pair or set of retaining tabs 920, 922 may include two retaining tabs protruding from opposite sides of the scaffold neck 122, spaced approximately 180 degrees apart. The additional locking tabs allow for more closure positions to help accommodate various tissue thicknesses (for example, as illustrated in connection with the different closure positions shown in FIGS. 89-92). FIGS. 56 and 57 illustrate the closure pin 902 in open and closed positions, respectively, within the scaffold neck 122.

Second Embodiment of Closure Pin

Figures 58, 59:
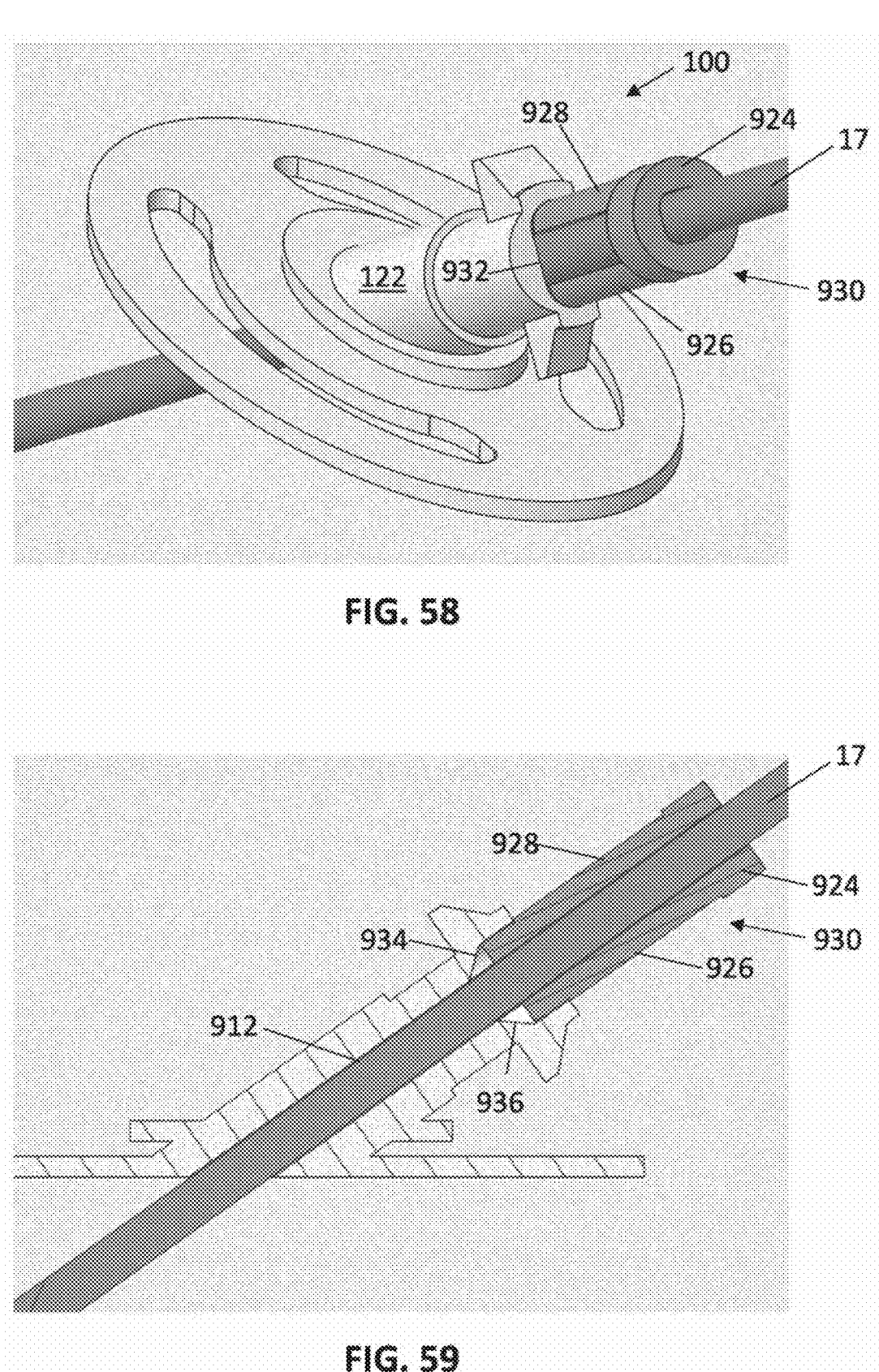
FIG. 58 illustrates an image of a closure device with a guidewire lumen closure pin, according to aspects of the present embodiments.
FIG. 59 illustrates an image of a closure device with a guidewire lumen closure pin, according to aspects of the present embodiments.
Figures 60, 61:
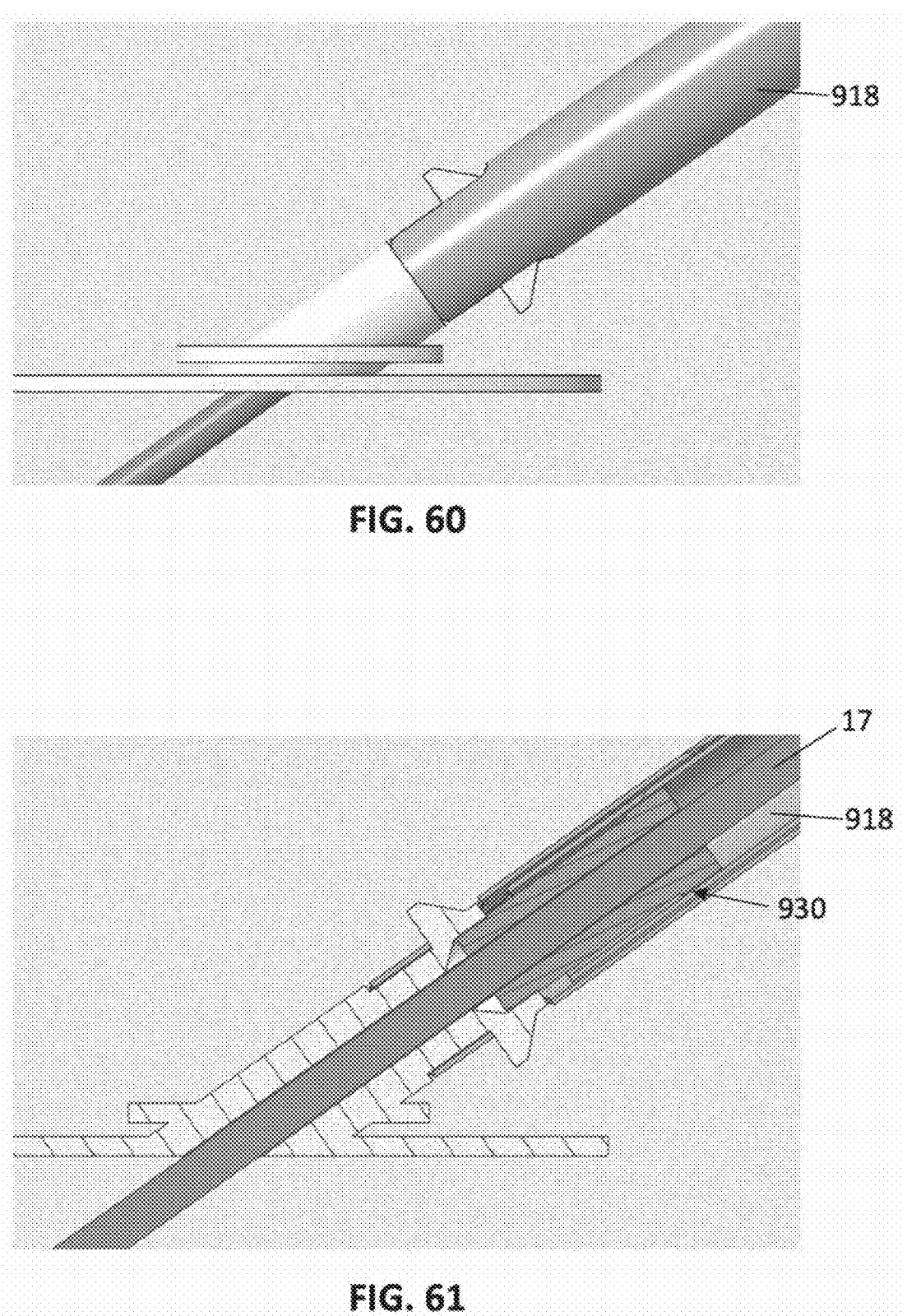
FIG. 60 illustrates an image of a closure device with a guidewire lumen closure pin, according to aspects of the present embodiments.
FIG. 61 illustrates an image of a closure device with a guidewire lumen closure pin, according to aspects of the present embodiments.
Figures 62, 63:
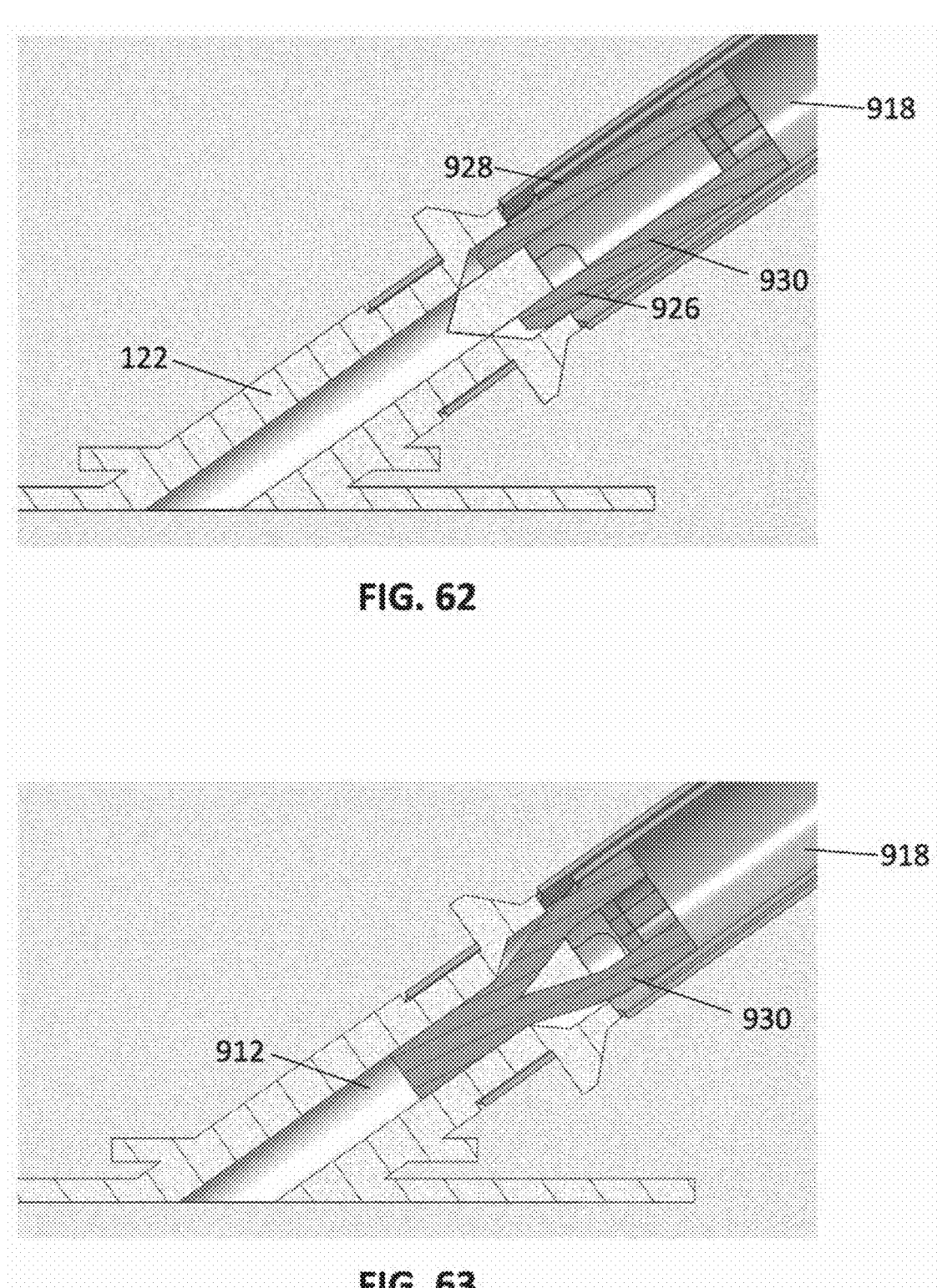
FIG. 62 illustrates an image of a closure device with a guidewire lumen closure pin, according to aspects of the present embodiments.
FIG. 63 illustrates an image of a closure device with a guidewire lumen closure pin, according to aspects of the present embodiments.

FIGS. 58-63 illustrate images of the closure device 100 with a second embodiment of the guidewire lumen closure pin 930, according to aspects of the present embodiments. The second embodiment of the closure pin 930 may include a circular or cylindrical pin head 924 configured to be concentrically disposed about the guidewire 17 when the guidewire is within the column 122 (or scaffold neck). The closure pin 930 may include first and second arms 926 and 928 configured to be disposed on opposite sides of the guidewire 17, and slidable within an elongated mouth 932 disposed within the column 122. The column 122 may include first and second internal tapers 934, 936, as shown in FIG. 59, to push the first and second arms 926, 928 into the guidewire lumen 912 as the closure pin 930 is pushed into the column 122 after the guidewire 17 is removed. FIGS. 60-63 illustrate the delivery shaft 918 (in addition to the closure device 100) with the second embodiment of the closure pin 930. FIGS. 62 and 63 illustrate the closure pin 930 after the guidewire 17 has been removed. FIG. 62 illustrates the position and shape of the closure pin 930 prior to being pushed further into the column 122, while FIG. 63 shows the closure pin 930 after being pushed into the guidewire lumen 912, thereby sealing the guidewire lumen 912. Because the first and second arms 926, 928 together fill the guidewire lumen 912 when in the sealed position of FIG. 63, each of the first and second arms 926, 928 may include a cross-sectional area that is roughly half of the cross-sectional area of the guidewire lumen 912.

Third Embodiment of Closure Pin

Figure 64:
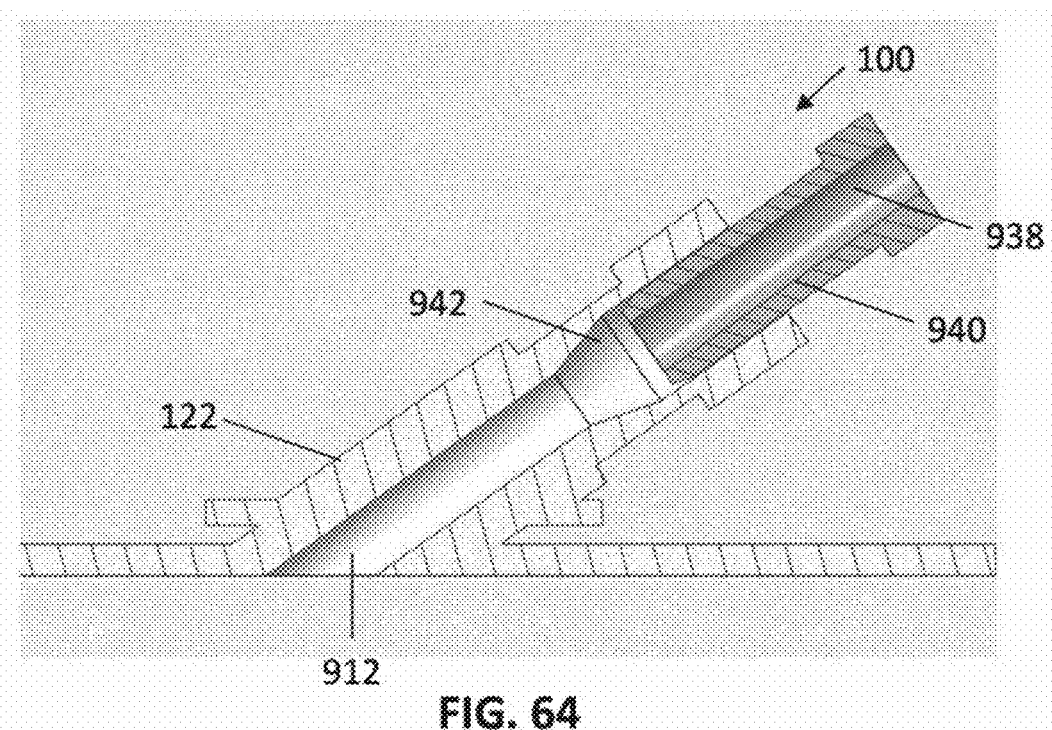
FIG. 64 illustrates an image of a closure device with a guidewire lumen closure pin, according to aspects of the present embodiments.
Figure 65:
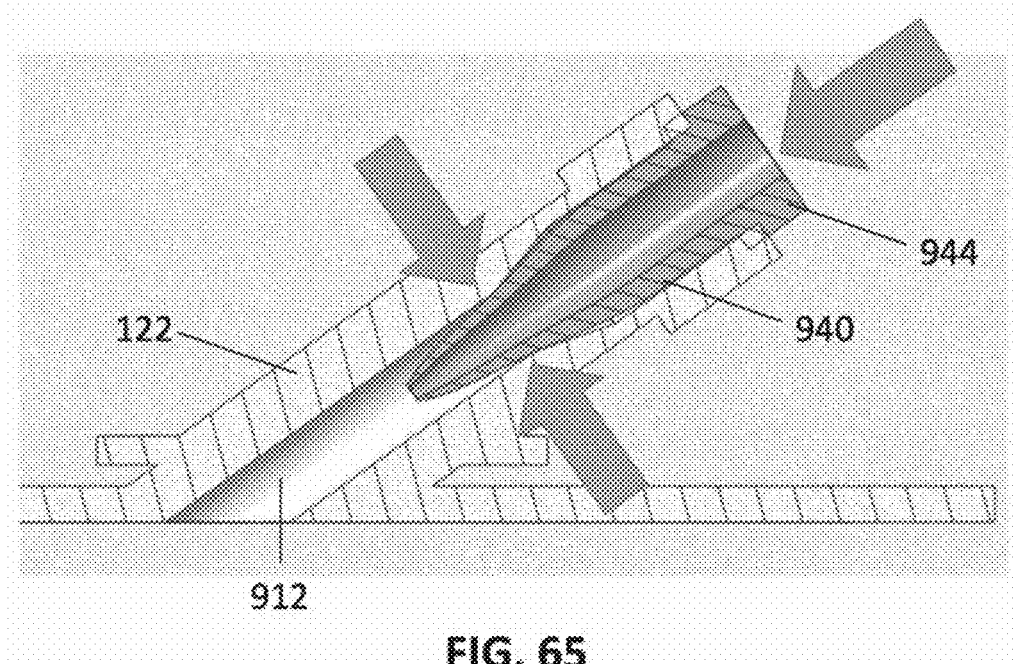
FIG. 65 illustrates an image of a closure device with a guidewire lumen closure pin, according to aspects of the present embodiments.

FIGS. 64 and 65 illustrate images of the closure device 100 with a third embodiment of the guidewire lumen closure pin 940, according to aspects of the present embodiments. The third embodiment of the closure pin 940 may include a circular or cylindrical pin head 944 configured to be concentrically disposed about the guidewire 17 when the guidewire is within the column 122 (and closure pin 940). The closure pin 940 may also include a through bore 938 running through the entire length of the closure pin 940, within which the guidewire 17 is disposed when it is within the column 122 (or scaffold neck). The device 100 shown in FIGS. 64 and 65 (specifically the column 122) includes a gradual tapered portion 942 with a cone-shaped interior for making the transition from a larger diameter of the closure pin 940 in the open position of FIG. 64 to the smaller diameter of the guidewire lumen 912. As a distal force is applied to the pin head 944 (see arrow pointing at the back of the pin in FIG. 65), the inner walls of the column 122 (or scaffold neck) at the gradual tapered portion 942 exert radially inward pressure on the closure pin 940 causing the closure pin 940 to be pinched or crimped inwardly (see arrows pointing inward at the tip of the pin in FIG. 65), thereby filling the entire space of the smaller diameter guidewire lumen 912 and sealing the guidewire lumen 912 in the process.

Fourth Embodiment of Closure Pin

Figure 66:
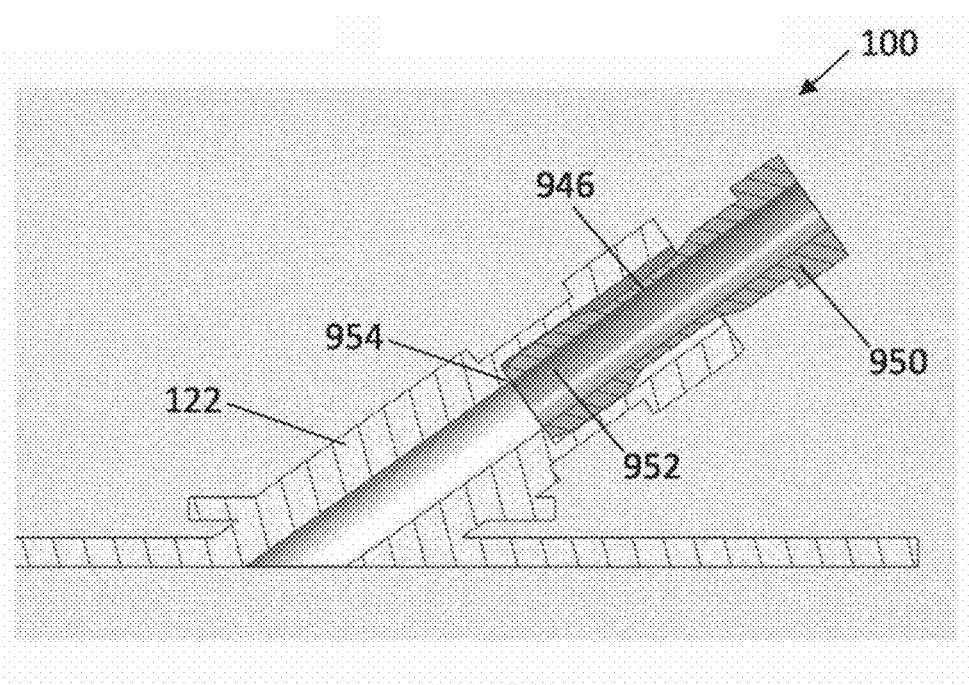
FIG. 66 illustrates an image of a closure device with a guidewire lumen closure pin, according to aspects of the present embodiments.
Figure 67:
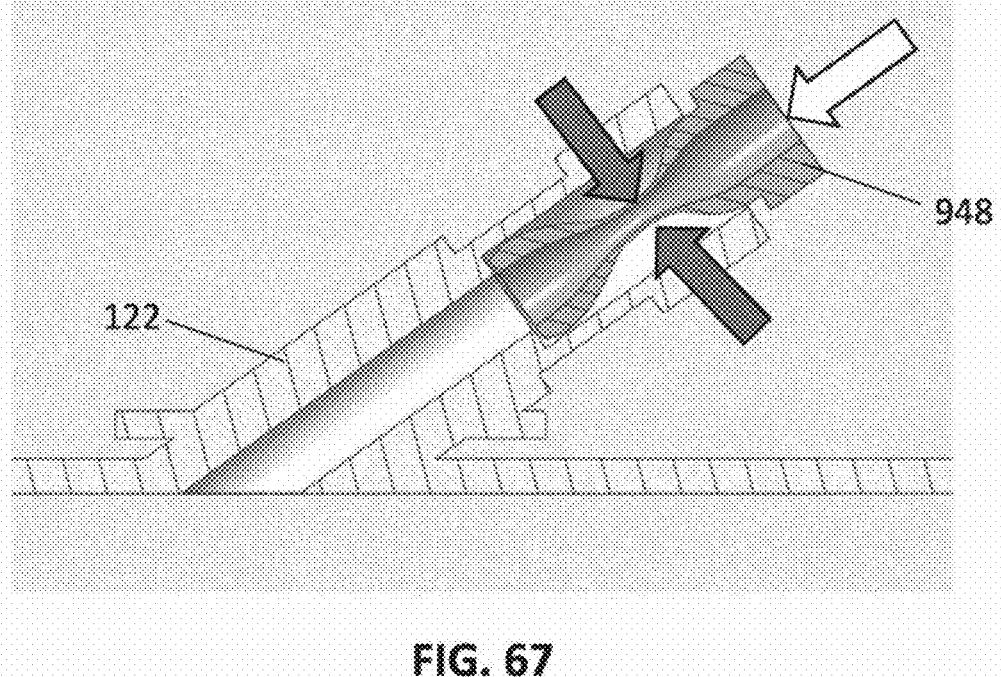
FIG. 67 illustrates an image of a closure device with a guidewire lumen closure pin, according to aspects of the present embodiments.
Figures 68, 69:
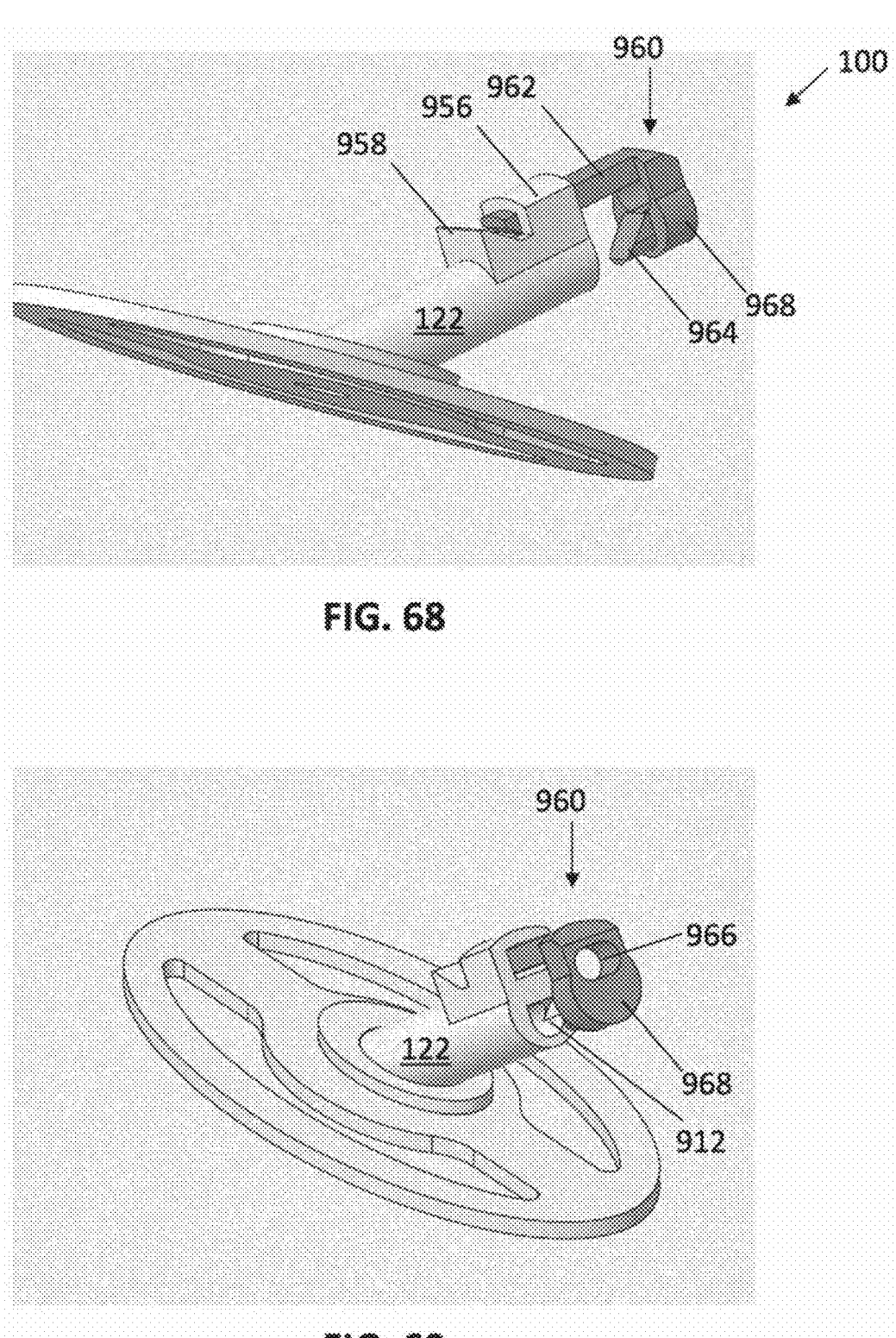
FIG. 68 illustrates an image of a closure device with a guidewire lumen closure pin, according to aspects of the present embodiments.
FIG. 69 illustrates an image of a closure device with a guidewire lumen closure pin, according to aspects of the present embodiments.

FIGS. 66 and 67 illustrate images of the closure device 100 with a fourth embodiment of the guidewire lumen closure pin 950, according to aspects of the present embodiments. The fourth embodiment of the closure pin 950 may include a circular or cylindrical pin head 948 configured to be concentrically disposed around the guidewire 17 when the guidewire is within the column 122 (and closure pin 950). The closure pin 950 may also include a throughbore 952 running through the entire length of the closure pin 950, within which the guidewire 17 is disposed when it is within the scaffold neck 122. The closure pin 950 shown in FIGS. 66 and 67 includes a rupture portion 952 with thin walls disposed within a longitudinal mid-section of the closure pin 950. The scaffold neck 122 of FIGS. 66 and 67 may include an internal orthogonal stop 954. In FIG. 67, as a distal force is applied to the pin head 948 (along white arrow), the distal end of the closure pin 950 contacts the internal orthogonal stop 954 causing the rupture portion 952 to rupture or crimp inwardly (due to the thinner walls of the rupture portion 946 (along the dark grey arrows), thereby filling the entire space of the guidewire lumen 912 and sealing the guidewire lumen 912 in the process.

Fifth Embodiment of Closure Pin

Figures 70, 71:
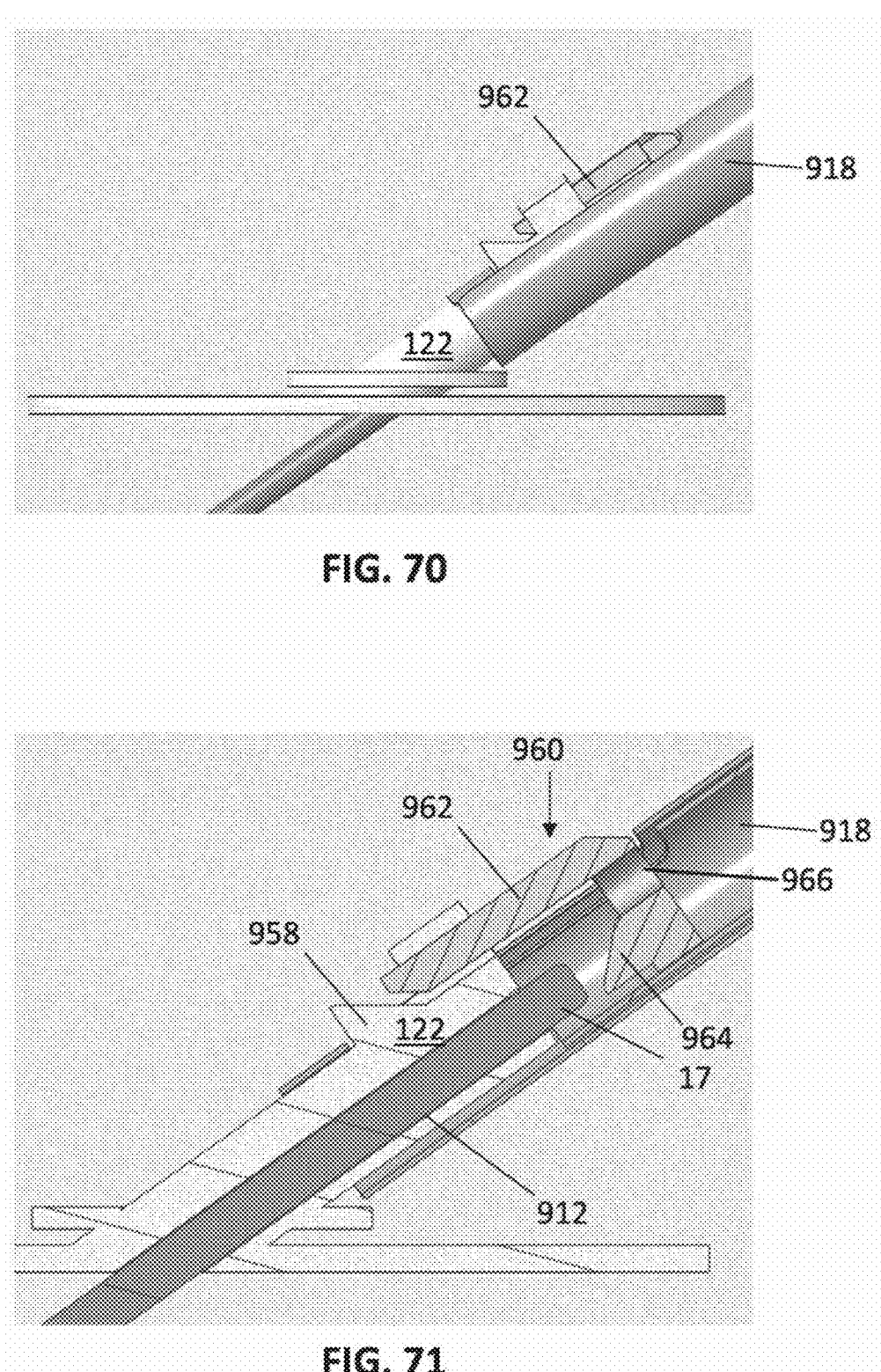
FIG. 70 illustrates an image of a closure device with a guidewire lumen closure pin, according to aspects of the present embodiments.
FIG. 71 illustrates an image of a closure device with a guidewire lumen closure pin, according to aspects of the present embodiments.
Figures 72, 73:
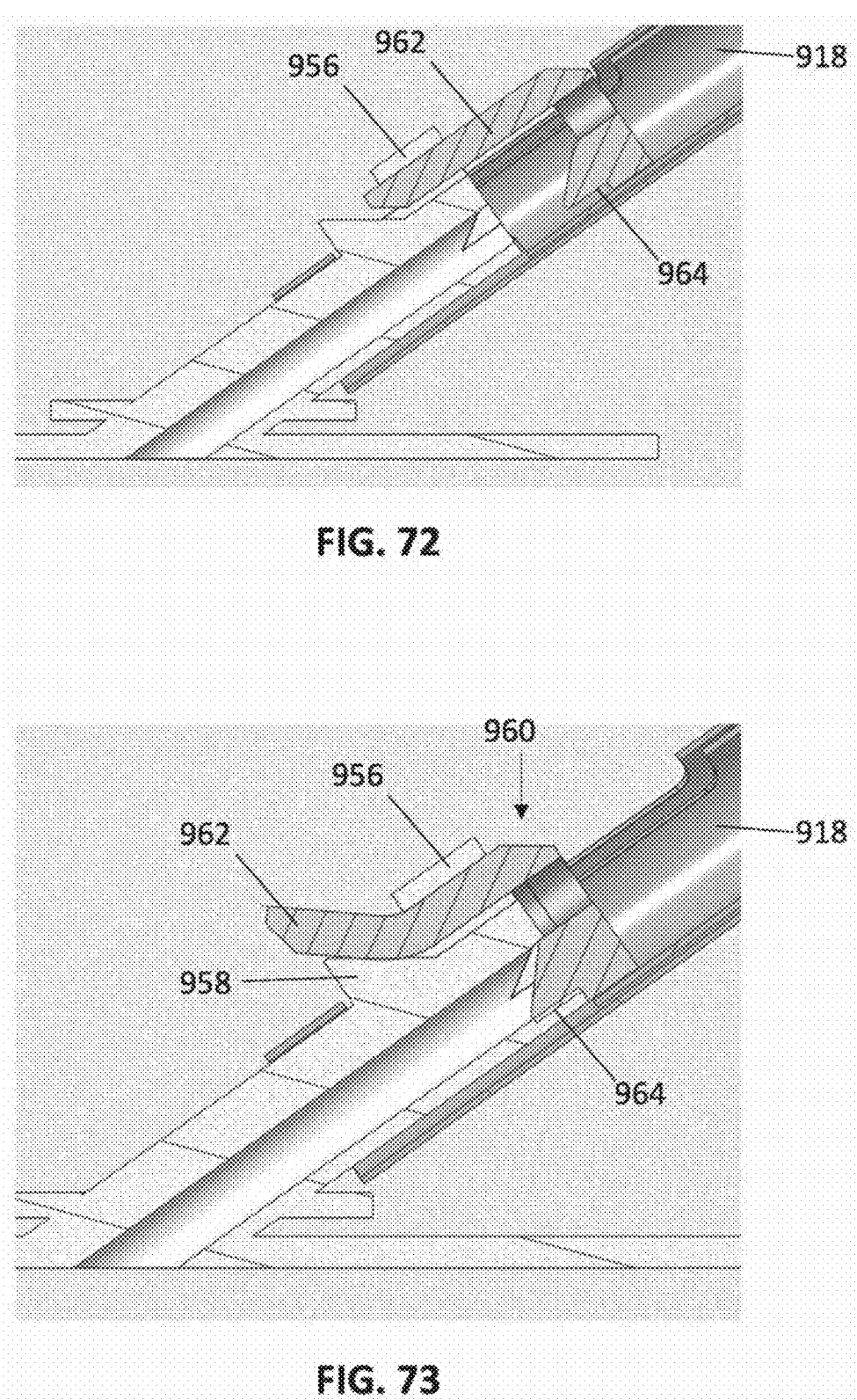
FIG. 72 illustrates an image of a closure device with a guidewire lumen closure pin, according to aspects of the present embodiments.
FIG. 73 illustrates an image of a closure device with a guidewire lumen closure pin, according to aspects of the present embodiments.
Figures 74, 75:
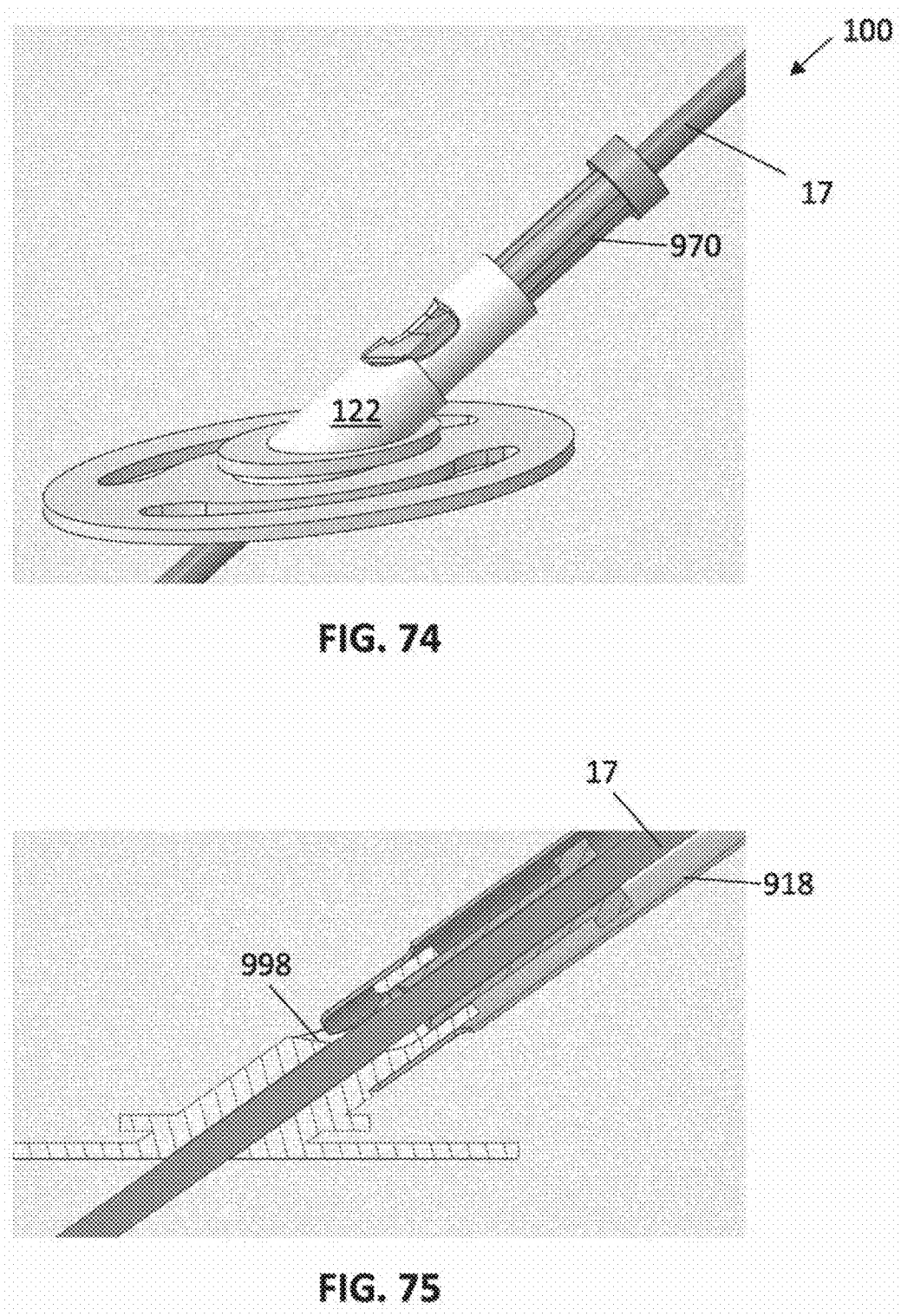
FIG. 74 illustrates an image of a closure device with a guidewire lumen closure pin, according to aspects of the present embodiments.
FIG. 75 illustrates an image of a closure device with a guidewire lumen closure pin, according to aspects of the present embodiments.
Figures 76, 77:
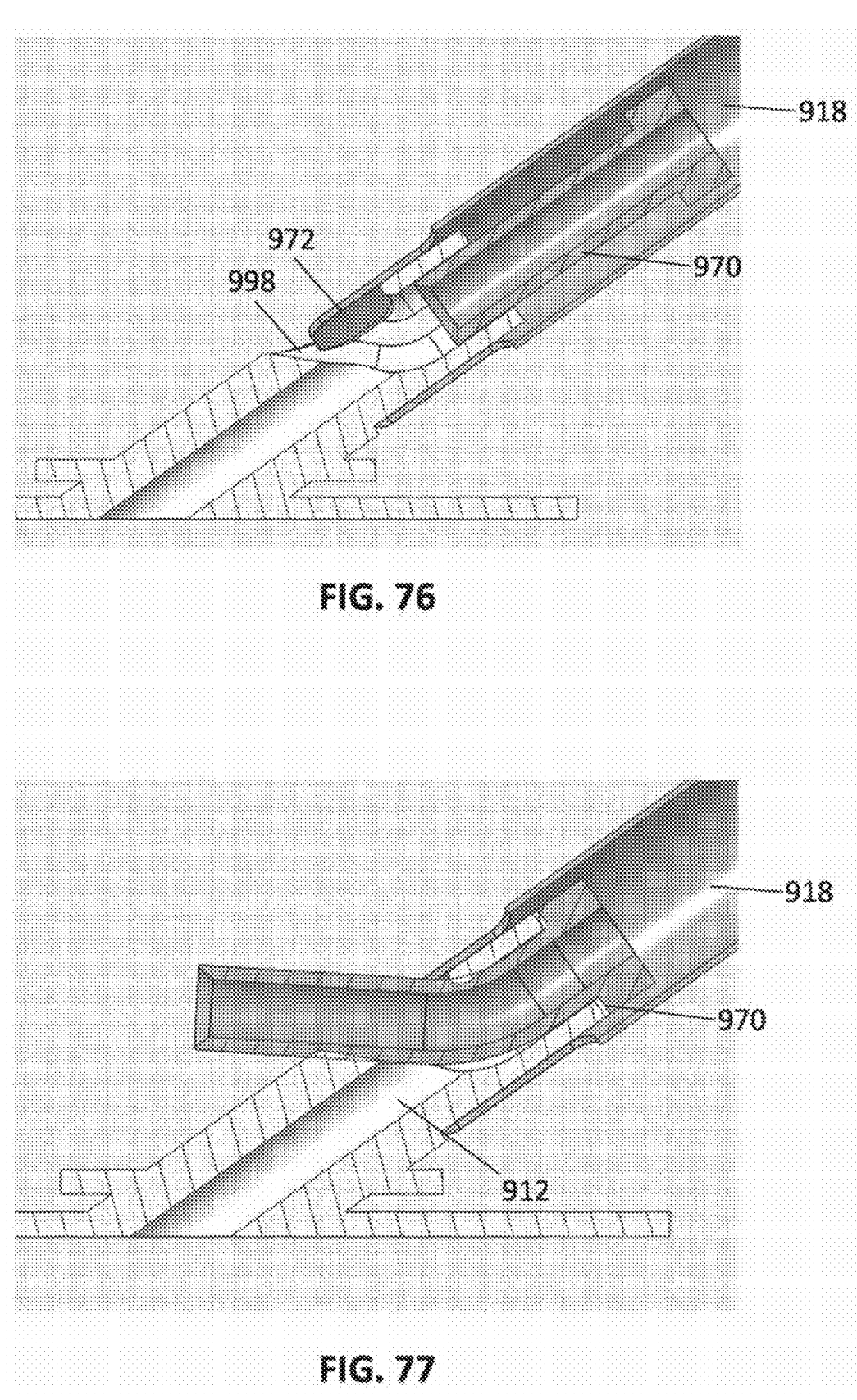
FIG. 76 illustrates an image of a closure device with a guidewire lumen closure pin, according to aspects of the present embodiments.
FIG. 77 illustrates an image of a closure device with a guidewire lumen closure pin, according to aspects of the present embodiments.
Figures 78, 79:
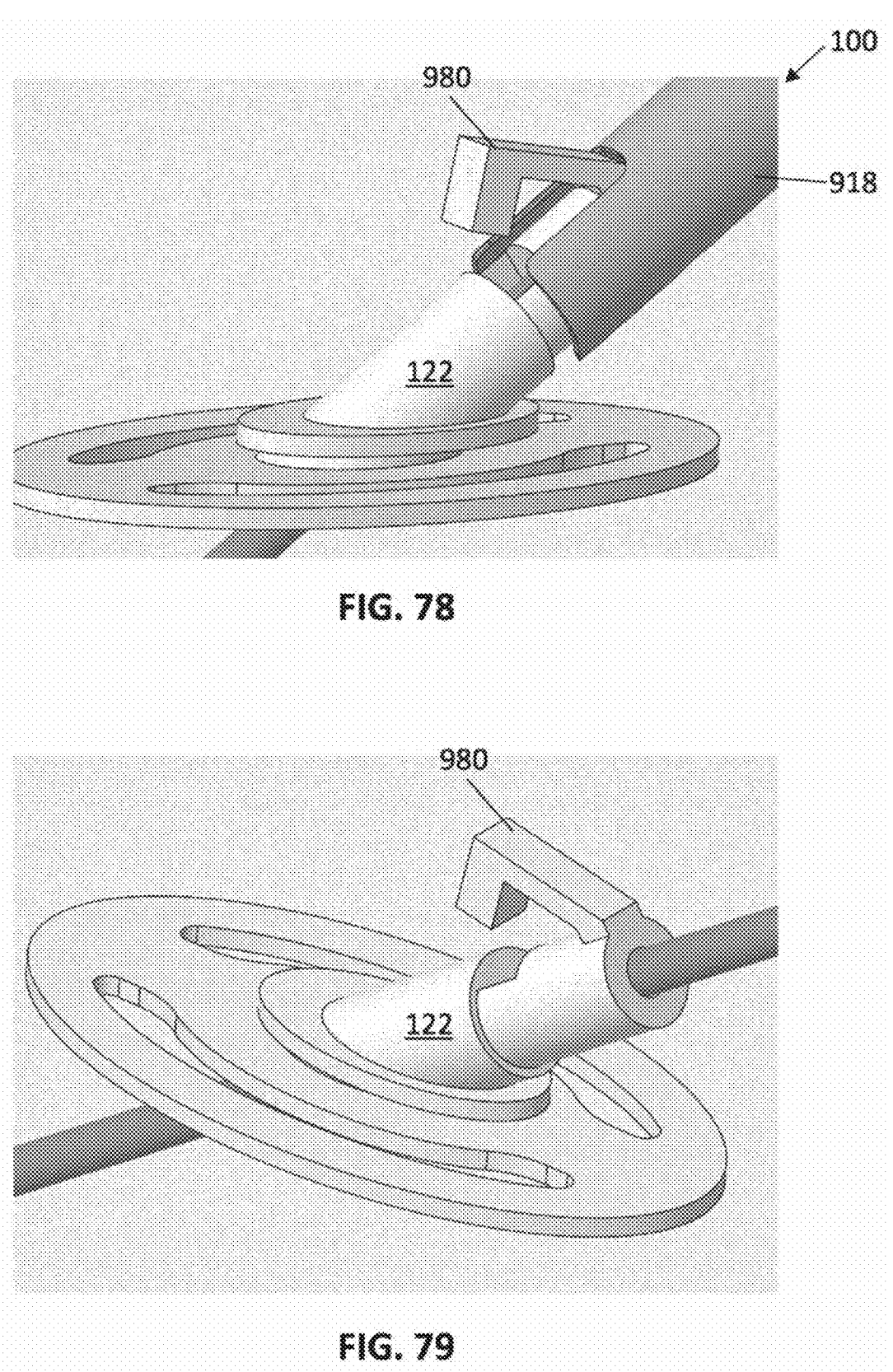
FIG. 78 illustrates an image of a closure device with a guidewire lumen closure pin, according to aspects of the present embodiments.
FIG. 79 illustrates an image of a closure device with a guidewire lumen closure pin, according to aspects of the present embodiments.
Figures 80, 81:
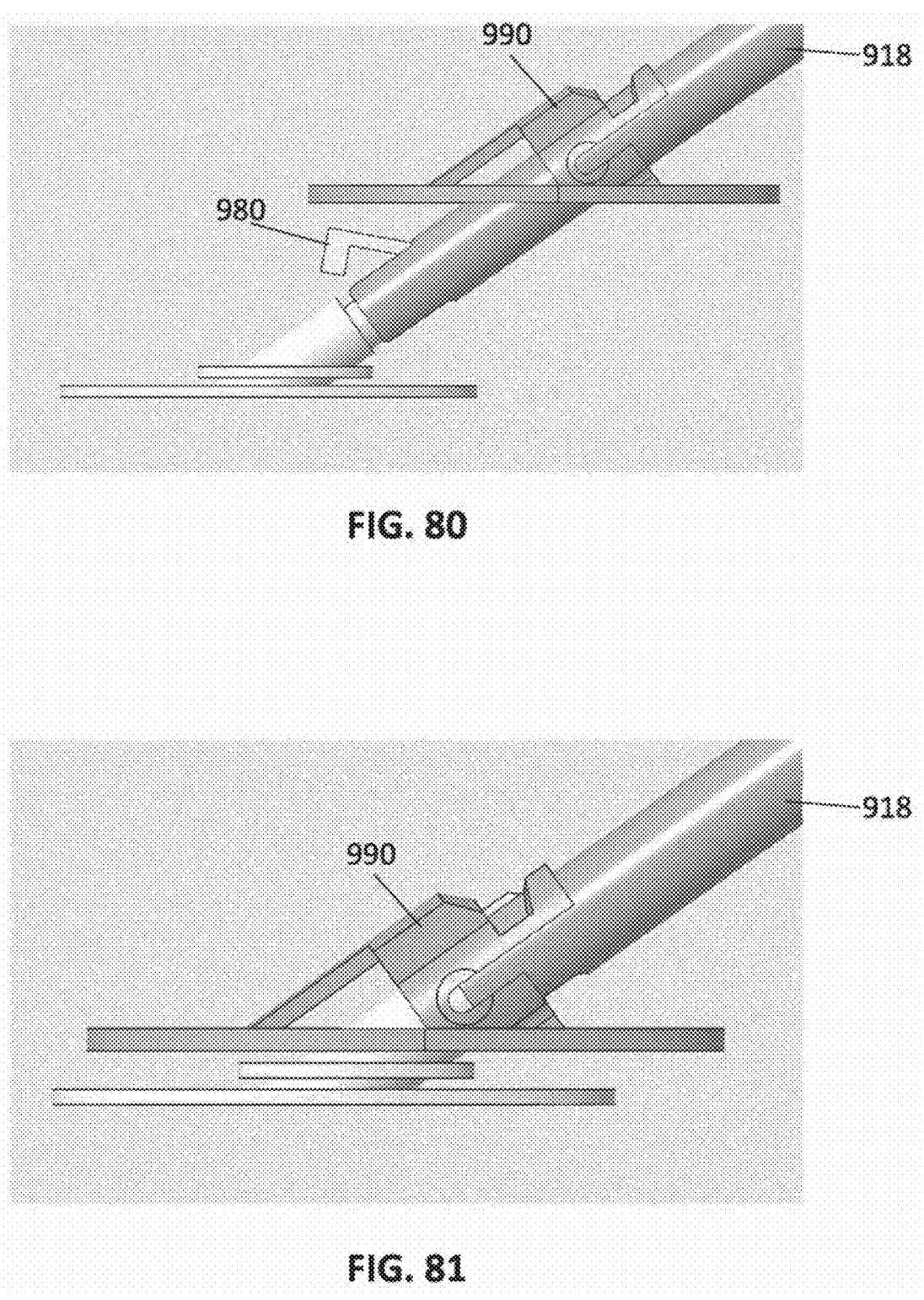
FIG. 80 illustrates an image of a closure device with a guidewire lumen closure pin, according to aspects of the present embodiments.
FIG. 81 illustrates an image of a closure device with a guidewire lumen closure pin, according to aspects of the present embodiments.

FIGS. 68-73 illustrate images of the closure device 100 with a fifth embodiment of the guidewire lumen closure pin 960, according to aspects of the present embodiments. The fifth embodiment of the closure pin 960 may include a slidable rod 962, an offset bore 966, an angled pin portion 964, and pin head 968. In some embodiments, both the angled pin portion 964 and the slidable rod 962 protrude distally form the pin head 968 while the offset bore 966 includes a hole disposed through the pin head 968 that is offset from the guidewire lumen 912. Stated otherwise, a centerline of the offset bore 966 is not collinear with a centerline of the guidewire lumen 912. The slidable rod 962 is configured to slide within a sleeve 956 disposed in column 122. At a distal end of the sleeve 956, the scaffold neck 122 may include a ramp portion 958 for deflecting the slidable rod at an angle as it protrudes through the sleeve 956, as show in FIGS. 71-73. FIGS. 70-73 illustrate the delivery shaft 918. As illustrated in FIG. 71, the guidewire 17 and guidewire lumen 912 are linearly offset form the offset bore 966, through which the guidewire is installed when it is in the scaffold neck 122. Accordingly, the guidewire 17 must bend in order to go through both the offset bore 966 and the guidewire lumen 912, which are not collinear with each other. Once the guidewire 17 is removed and the closure pin 960 is pushed distally toward the scaffold neck 122, the angled pin portion 964 (which is collinear with the guidewire lumen 912) is pushed into the guidewire lumen 912, thereby closing the guidewire lumen 912, as shown in FIG. 73. The slidable rod 962 bends at it deflects off the ramp portion 958. The inherent stiffness and partial elasticity of the slidable rod 963, in connection with the sheath 956, helps to hold the closure pin 960 into place once it is in the closed position.

Sixth Embodiment of Closure Pin

FIGS. 74-77 illustrate images of the closure device 100 with a sixth embodiment of the guidewire lumen closure pin 970, according to aspects of the present embodiments. The sixth embodiment of the closure pin 970 is concentrically disposed 360 degrees around the guidewire 17 and deflects off an angled surface 998 and through an aperture 972 in the scaffold neck 122 (or scaffold neck) and/or delivery shaft 918 such that a distal end of the closure pin 970 protrudes across the guidewire lumen 912 and out of the aperture 972, thereby sealing the guidewire lumen 912, as show in FIG. 77.

Seventh Embodiment of Closure Pin

Figures 82, 83:
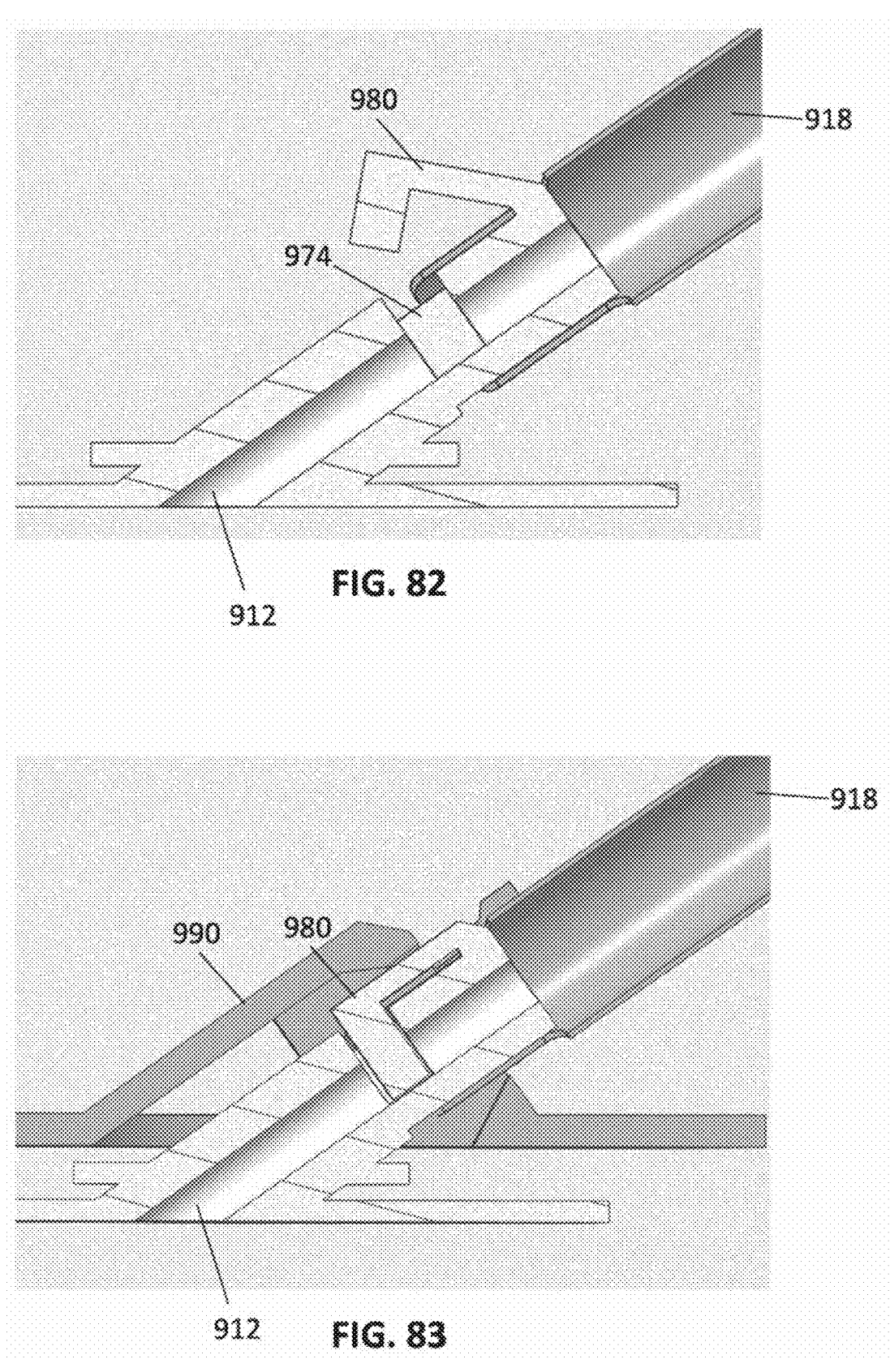
FIG. 82 illustrates an image of a closure device with a guidewire lumen closure pin, according to aspects of the present embodiments.
FIG. 83 illustrates an image of a closure device with a guidewire lumen closure pin, according to aspects of the present embodiments.

FIGS. 78-83 illustrate images of the closure device 100 with a seventh embodiment of the guidewire lumen closure pin 980, according to aspects of the present embodiments. The seventh embodiment of the closure pin 980 includes an L-shaped closure pin 980 that is integrated into (and monolithic with) the scaffold neck 122. As an external fixation 990 slides down the delivery shaft and over the L-shaped closure pin 980 (FIGS. 80 and 81), the external fixation 990 forces the orthogonal tip of the L-shaped closure pin 980 into a partial bore 974 in only one sidewall of the column 122 (i.e., rather than all the way through both side walls; shown in FIG. 82). The orthogonal tip of the L-shaped closure pin 980 traverses the guidewire lumen 912, thereby sealing the guidewire lumen 912, as shown in FIG. 83. In the embodiments of each of FIGS. 46-77, the closure device may include a push tube disposed concentrically within the delivery shaft 918, the push tube being used for distally pushing the closure pins 902, 930, 940, 950, 960, and 970 into the column 122 and/or guidewire lumen 912 after the guidewire 17 has been withdrawn from the guidewire lumen 912. In each of the second, third, fourth, sixth, and seventh embodiments of the closure pin 930, 940, 950, 970, 980, the scaffold neck 122 is configured such that the guidewire 17 and guidewire lumen 912 are centered (i.e., concentric) within the scaffold neck 122. In each of the first and fifth embodiments of the closure pin 902, 960, the scaffold neck 122 is configured such that the guidewire 17 and guidewire lumen 912 are offset (i.e., eccentric) within the scaffold neck 122.

External Fixation Design

Figures 84, 85:
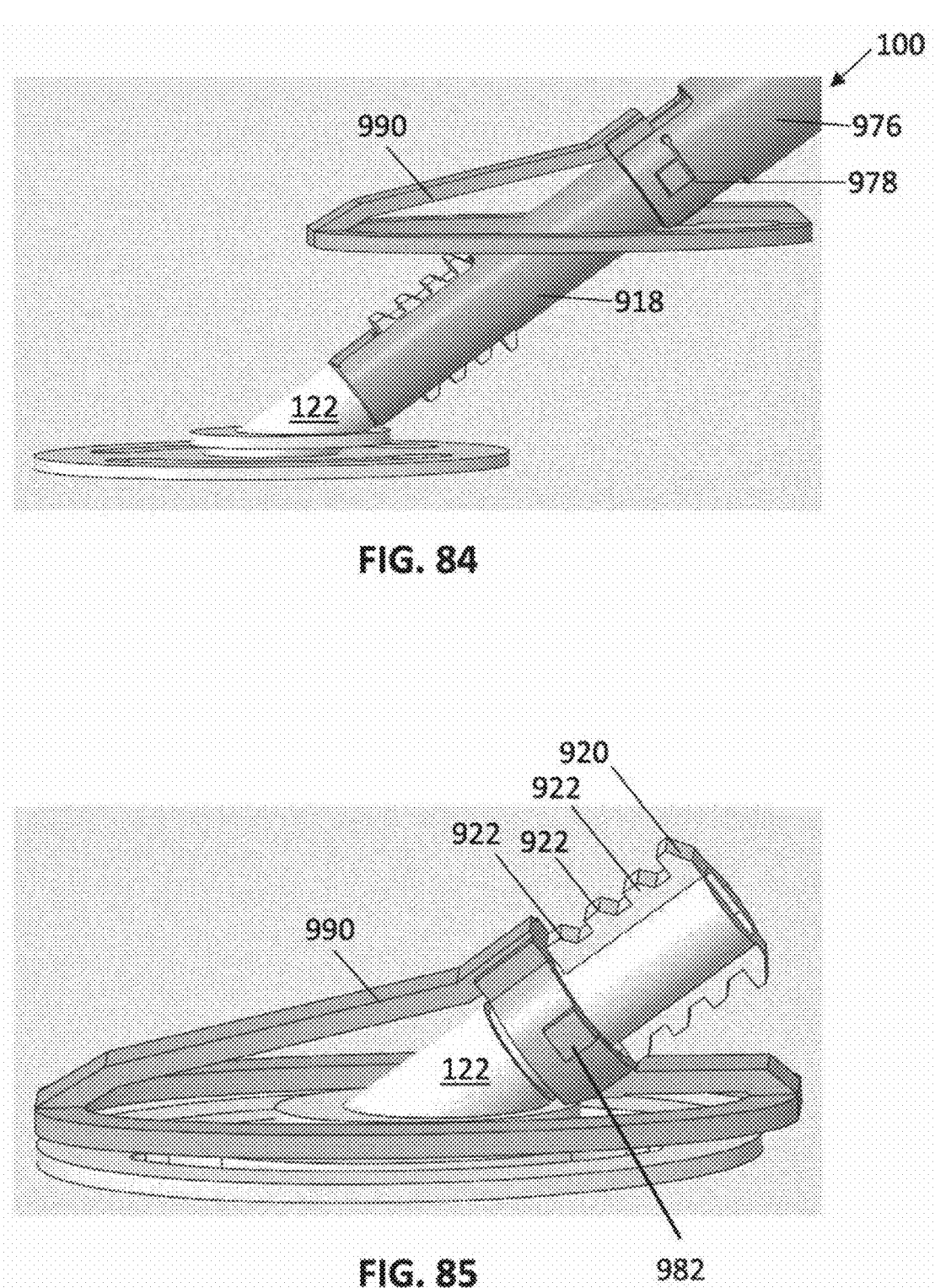
FIG. 84 illustrates an image of a closure device, according to aspects of the present embodiments.
FIG. 85 illustrates an image of a closure device, according to aspects of the present embodiments.
Figures 88, 89:
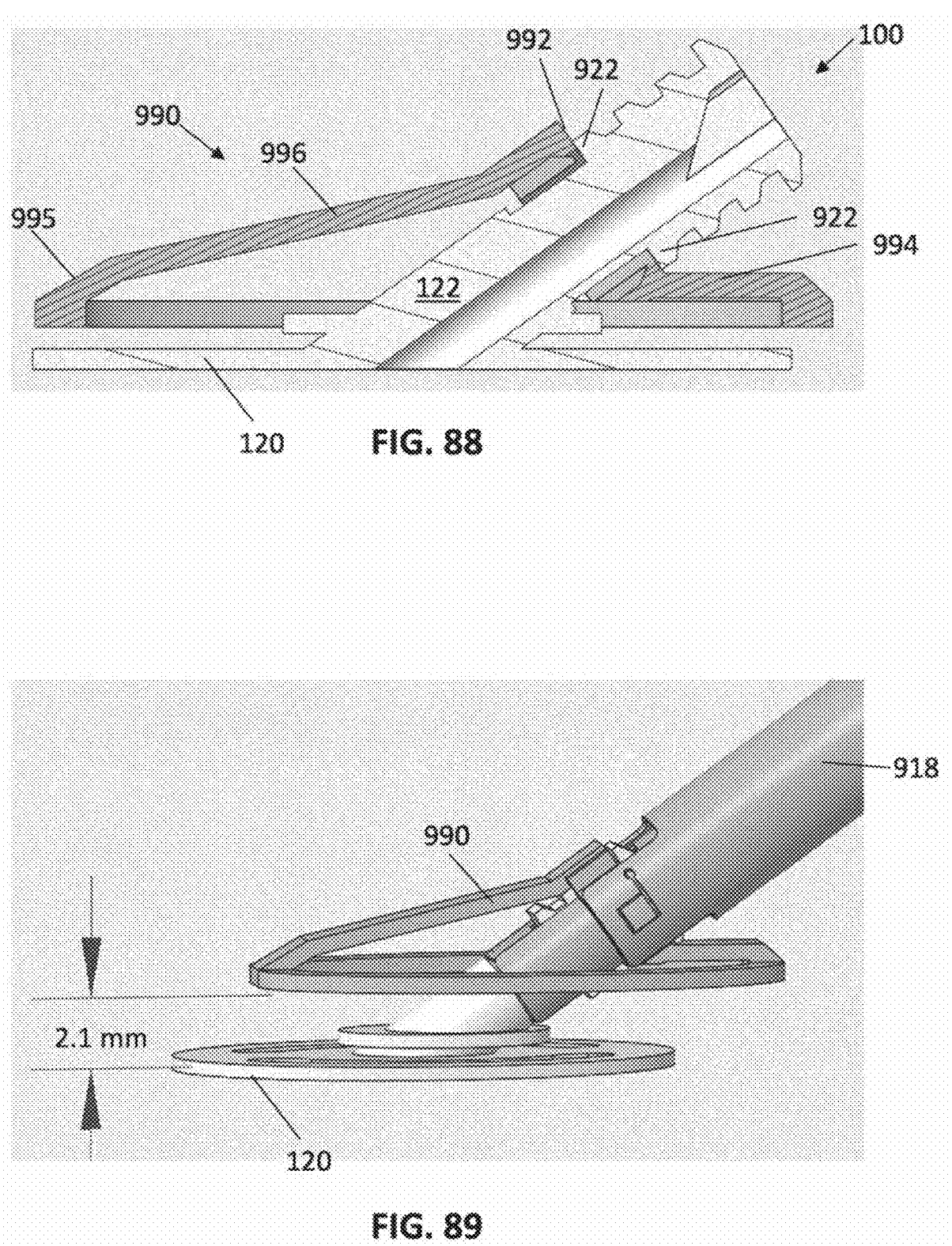
FIG. 88 illustrates an image of a closure device, according to aspects of the present embodiments.
FIG. 89 illustrates an image of a closure device, according to aspects of the present embodiments.

FIGS. 84-88 illustrate images of the closure device 100 including the external fixation 990 and base 120 with scaffold neck 122 protruding therefrom, according to aspects of the present embodiments. As shown in FIG. 84, the delivery tube 976 concentrically slides around the delivery shaft 918 to deliver the external fixation 990 to the closure site. The delivery tube 976 may include square-shaped recesses 978 on opposing sides for interfacing with square-shaped lateral protrusions 982 on the external fixation 990 during delivery of the external fixation 990 to the closure site. The scaffold neck 122 may include four pairs of locking tabs, with a proximal pair of retaining tabs 920 being larger than each of the second, third, and fourth pairs of retaining tabs 922, similar to the embodiments of FIGS. 55-57. The locking tabs interface with a top surface 992 of a collar 984 of the external fixation 990, as shown in FIGS. 85, 87, and 88. The collar 984 becomes disposed around the scaffold neck 122 as the external fixation 990 moves distally toward the closure site. Referring to FIG. 87, the external fixation 990 may include an anterior member 996 and a posterior member 994, both coupled to opposing sides of the collar 984. In some embodiments, the anterior and posterior members 996, 994 are each coupled to lateral members 988 on opposing lateral sides of the external fixation 990, a configuration which provides enhanced flexibility of the external fixation. The collar 984 may also include an internal recess 986 that interfaces with the retaining tabs 920, 922 allowing and/or encouraging movement of the external fixation 990 in a distal direction around the scaffold neck 122. The collar 984 may include a larger diameter compared to previous designs to accommodate a larger-diameter scaffold neck 122, which in turn may be larger to accommodate a thicker (for example, 0.035 inch) guidewire 17. The 0.035 inch guidewire 17 (or, for example 0.02 to 0.05 inch guidewire 17) allows procedures to be performed without the need to do a wire exchange during the closure process, thereby saving time and eliminating steps. The top surface 992 of the collar 984 prevents movement in the proximal direction of the external locator along the delivery shaft 918 after the collar 984 has engaged the retaining tabs 920, 922.

FIG. 88 shows the external locator 990 engaged with the base 120 and scaffold neck 122, according to aspects of the present embodiments. In the configuration of FIG. 88, the fourth pair of retaining tabs 922 (that is, on opposing sides of the scaffold neck 122) interface with corresponding portions of the top surface 992 of the collar 984 to prevent proximal movement of the external locator 990 relative to the base 120. For clarity purposes, the flexible patch is omitted from FIGS. 83, 84, and 88-92, but would be present in operation. Referring to FIGS. 87 and 88, the external locator 990 may include an anterior member that includes two segments: a short steep first segment 995, and a longer less steep second segment 996, with the short steep first segment 995 being located distal of, and connecting to, the longer less steep second segment 996. The short steep first segment 995 may be oriented at an angle of about 30 degrees (or from about 28 degrees to about 32 degrees, or from about 25 degrees to about 35 degrees) from the horizontal plane (i.e., the plane of base 120). The longer less steep second segment 996 may be oriented at an angle of about 13 degrees (or from about 11 degrees to about 15 degrees, or from about 8 degrees to about 18 degrees) from the horizontal plane (i.e., the plane of base 120). The posterior member 994 may be oriented such that it is substantially parallel to (for example, angled within about 1 degree and/or within about 2 degrees of) the horizontal plane (i.e., the plane of base 120). In some embodiments, the posterior member 994 may be less than half the length of the longer less steep second segment of the anterior member 996. The centerline of scaffold neck 122 (for example, the centerline of guidewire lumen 912) may be oriented at an angle of about 35 degrees (or from about 33 degrees to about 37 degrees, or from about 30 degrees to about 40 degrees) from the horizontal plane (i.e., the plane of base 120). In some embodiments, each of the anterior member 996, the posterior member 994, and the lateral members 998 may include a cross section with a width that is greater than the height while the collar 984 may include a cross section in which the height is greater than the width. The configuration and design of external locator 990 (for example, the orientations and relative dimension of each of the anterior member 996, the posterior member 994, the lateral members 998, the collar 984, and other features of the external locator 990) allow the external locator 990 to accommodate the various loads (distal, proximal, lateral loads, etc.) experienced when in use, while simultaneously allowing the necessary flexibility required for closure of the target site. As a result, the present embodiments allow closure device 100 to accommodate the variety of tissue types and anatomy/disease states of patient's tissue tracts.

Figures 90, 91, 92:
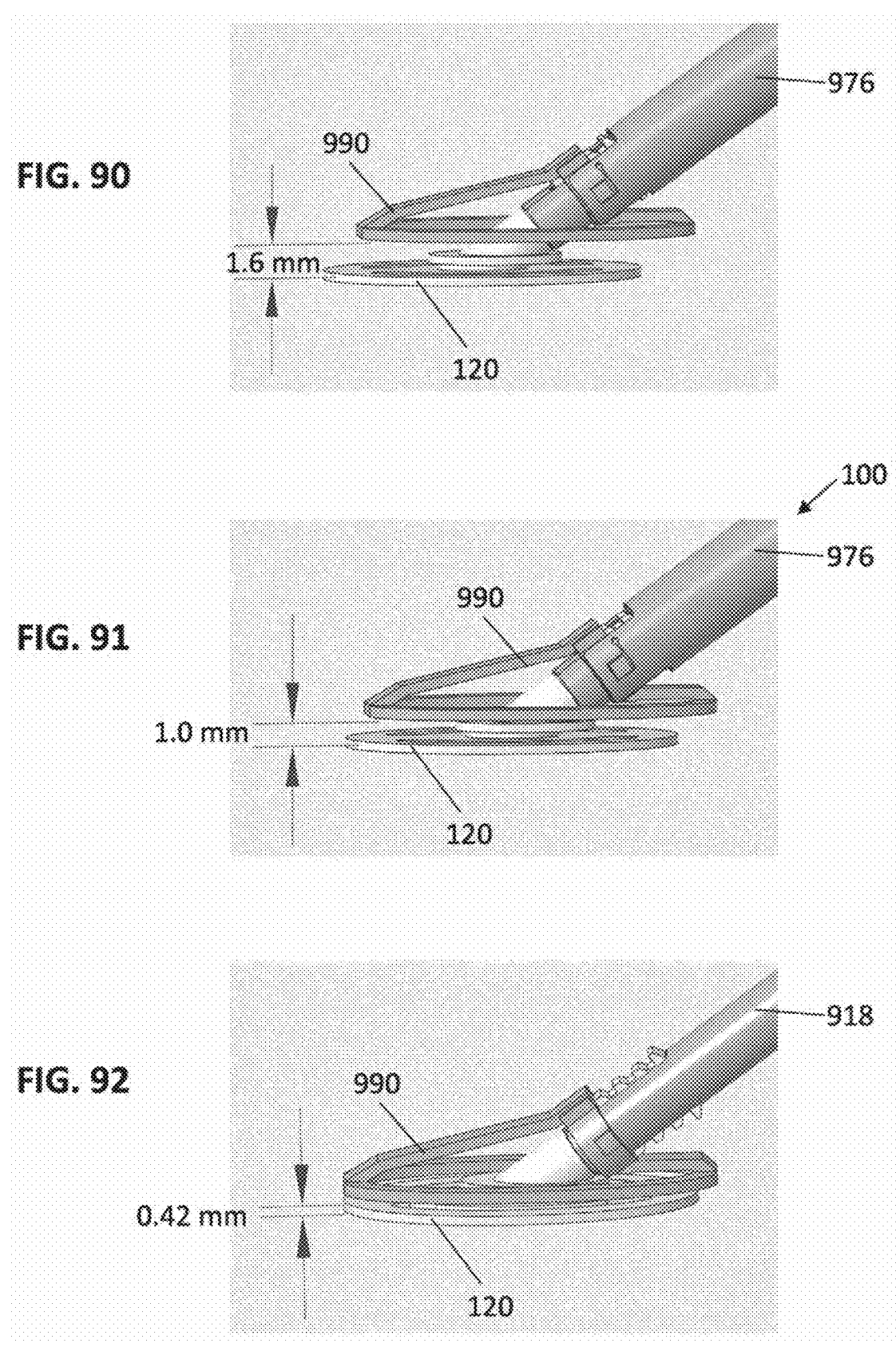
FIG. 90 illustrates an image of a closure device, according to aspects of the present embodiments.
FIG. 91 illustrates an image of a closure device, according to aspects of the present embodiments.
FIG. 92 illustrates an image of a closure device, according to aspects of the present embodiments.

FIGS. 89-92 illustrate four different closure positions of the closure device 100 corresponding to each of the four sets of retaining tabs 920, 922. The various closure positions allow the closure device 100 to accommodate a range of anatomies of patients who require endovascular treatments which may require closures of arteriotomies and/or venotomies. In FIG. 89, which corresponds to the external locator being engaged with the first set of retaining tabs 920, the device is configured such that there is a 2.1 mm gap between the external locator 990 and the base 120. In FIG. 90, which corresponds to the external locator being engaged with the second set of retaining tabs 922, the device is configured such that there is a 1.6 mm gap between the external locator 990 and the base 120. In FIG. 91, which corresponds to the external locator being engaged with the third set of retaining tabs 922, the device is configured such that there is a 1.0 mm gap between the external locator 990 and the base 120. In FIG. 92, which corresponds to the external locator being engaged with the fourth set of retaining tabs 922, the device is configured such that there is a 0.42 mm gap between the external locator 990 and the base 120.

Other examples and methods of the delivery device are described in U.S. Patent Application Publication Nos. 2013/0274795, 2017-0333014, and 2019/0021710, the contents of which are incorporated by reference herein in their entirety.

Second Embodiment of Closure Device

FIGS. 93-101 illustrate a second embodiment of the vascular closure device 1000 and system that feature various modifications to their designs that may improve performance and/or ease of use. In some embodiments, these modifications may include: increased thickness of some portions of some components to increase stiffness; decreased thickness of some portions of some components to decrease stiffness and use less material during manufacture; and curved and/or smoothed edges rather than sharp edges on various components to improve movement of components through a delivery device and through a the lumen of a body vessel and/or openings or wounds. The vascular closure device 1000 may be used to close openings in either veins or arteries.

Figure 93:
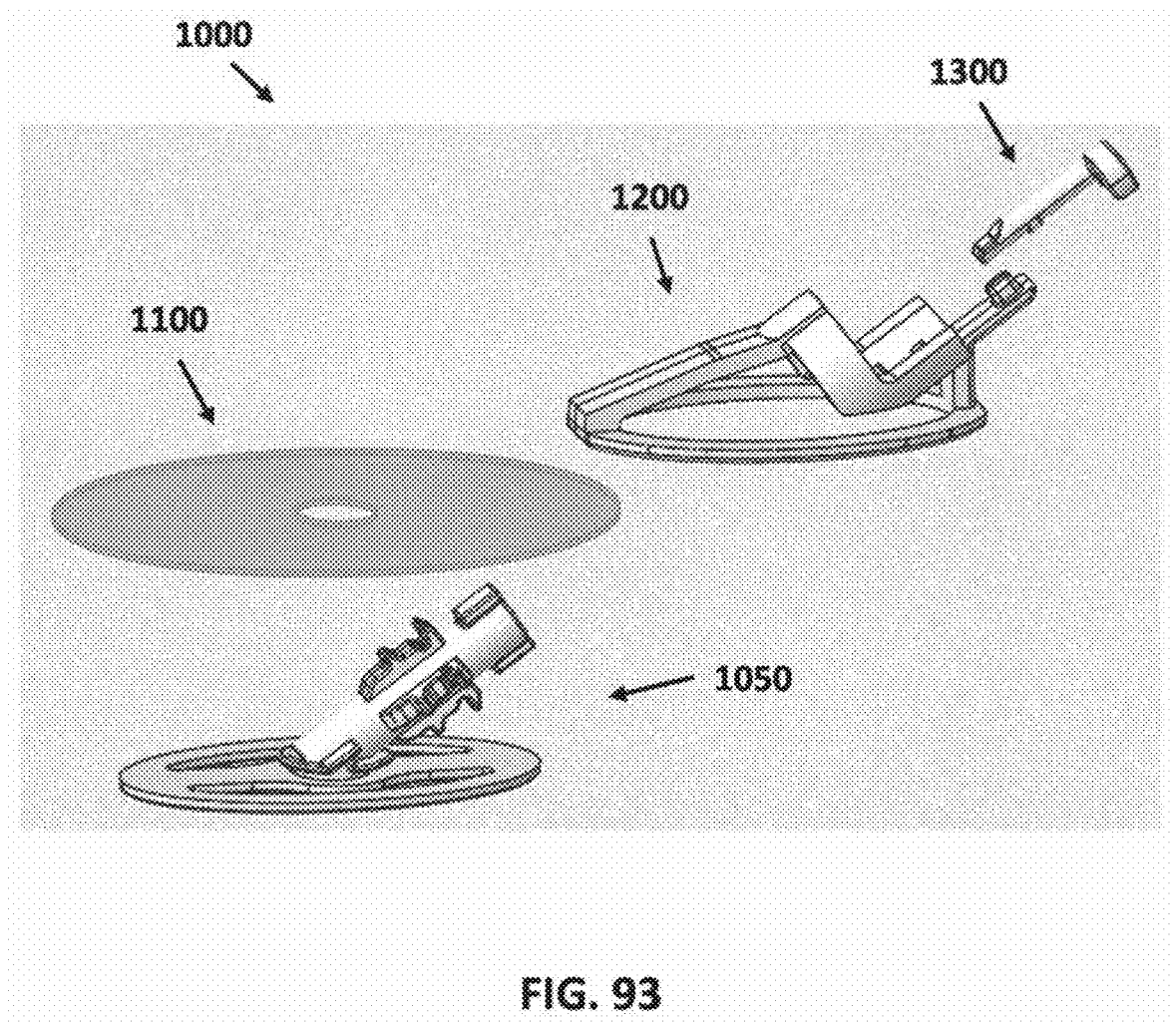
FIG. 93 illustrates a perspective view of further embodiments of components of a closure device assembly, including a scaffold, a patch, an external fixation, and a closure pin, according to aspects of the present embodiments.

FIG. 93 illustrates a perspective view of further embodiments of components of a closure device assembly 1000, including a scaffold 1050, a patch 1100, an external fixation 1200, and a closure pin 1300, according to aspects of the present embodiments. As with the previous embodiments, the closure device assembly 1000 is used to close an aperture or vascular opening, which may be openings in arteries and/or veins in a subject.

Figures 94A, 94B:
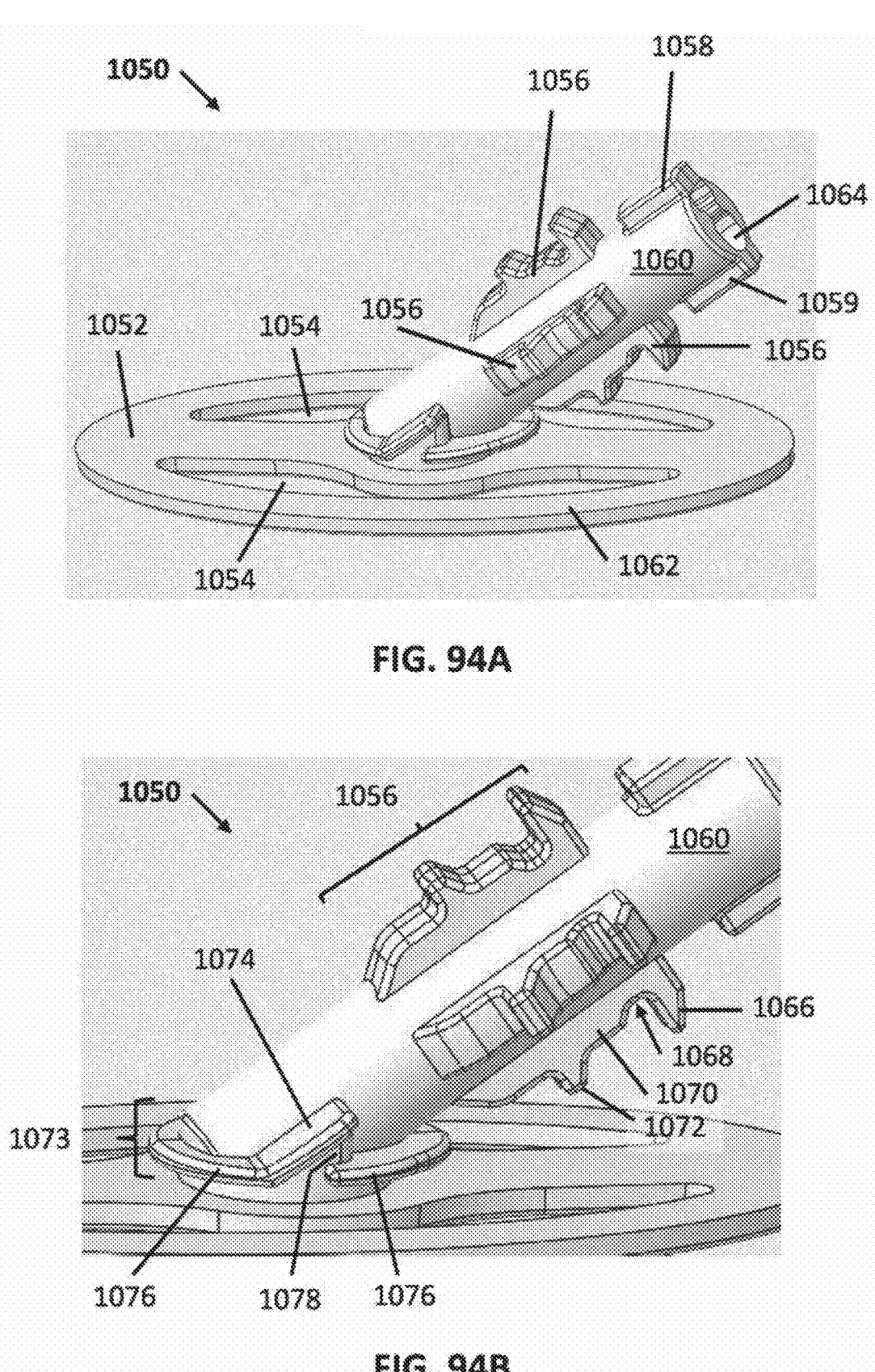
FIG. 94A illustrates a perspective view of a scaffold, according to aspects of the present embodiments.
FIG. 94B illustrates an enlarged view of a scaffold neck and base plate, according to aspects of the present embodiments.

FIG. 94A illustrates a perspective view of a scaffold 1050, according to aspects of the present embodiments. The scaffold 1050 may include a base plate 1052 and a neck 1060. In some embodiments, the shape of the base plate 1052 may be a disc with a circular, oval, or rectangular shape, and the base plate 1052 may include one or more openings 1054.

The overall shapes of the base plate 1052 and openings 1054 may allow the base plate 1052 to bend to better fit within the lumen of an artery or vein or other space. The neck 1060 may have a generally cylindrical shape.

Referring still to FIG. 94A, the scaffold neck 1060 further includes four retaining tabs 1056 that are disposed circumferentially around the outer surface of the neck 1060. The retaining tabs 1056 may include at least two curved protrusions that extend radially and may interface with an external fixation 1200. The neck 1060 may include at least two pads (i.e., retaining pads) 1058 and 1059 that may interact with the external fixation 1200 (for example, with the collar 1206 of the external fixation 1200). The scaffold neck 1060 may include an interior lumen 1064 for the passage of a guidewire 1001. The interior lumen 1064 may also be termed a guidewire lumen 1064, similar to the guidewire lumen 912 of earlier embodiments.

FIG. 94B illustrates an enlarged view of a neck 1060 and base plate 1052 of a scaffold 1050, according to aspects of the present embodiments. Each retaining tab 1056 may include a first protrusion 1066, a notch 1068, a flat portion 1070, and a second protrusion 1072, which may all be aligned longitudinally along the axis of the scaffold neck 1060.

Referring still to FIG. 94B, some embodiments may include a threaded portion 1073 located at the base of the scaffold neck 1060. The threaded portion 1073 may comprise a thread 1076 disposed circumferentially around the base of the neck 1060, and terminate in a lifted portion 1074 that leaves a gap 1078 so that an interior opening 1102 in a patch 1100 may be inserted and secured by the thread 1076 to hold the patch 1100 against the upper surface of the base plate 1052 of the scaffold 1050.

Figure 95:
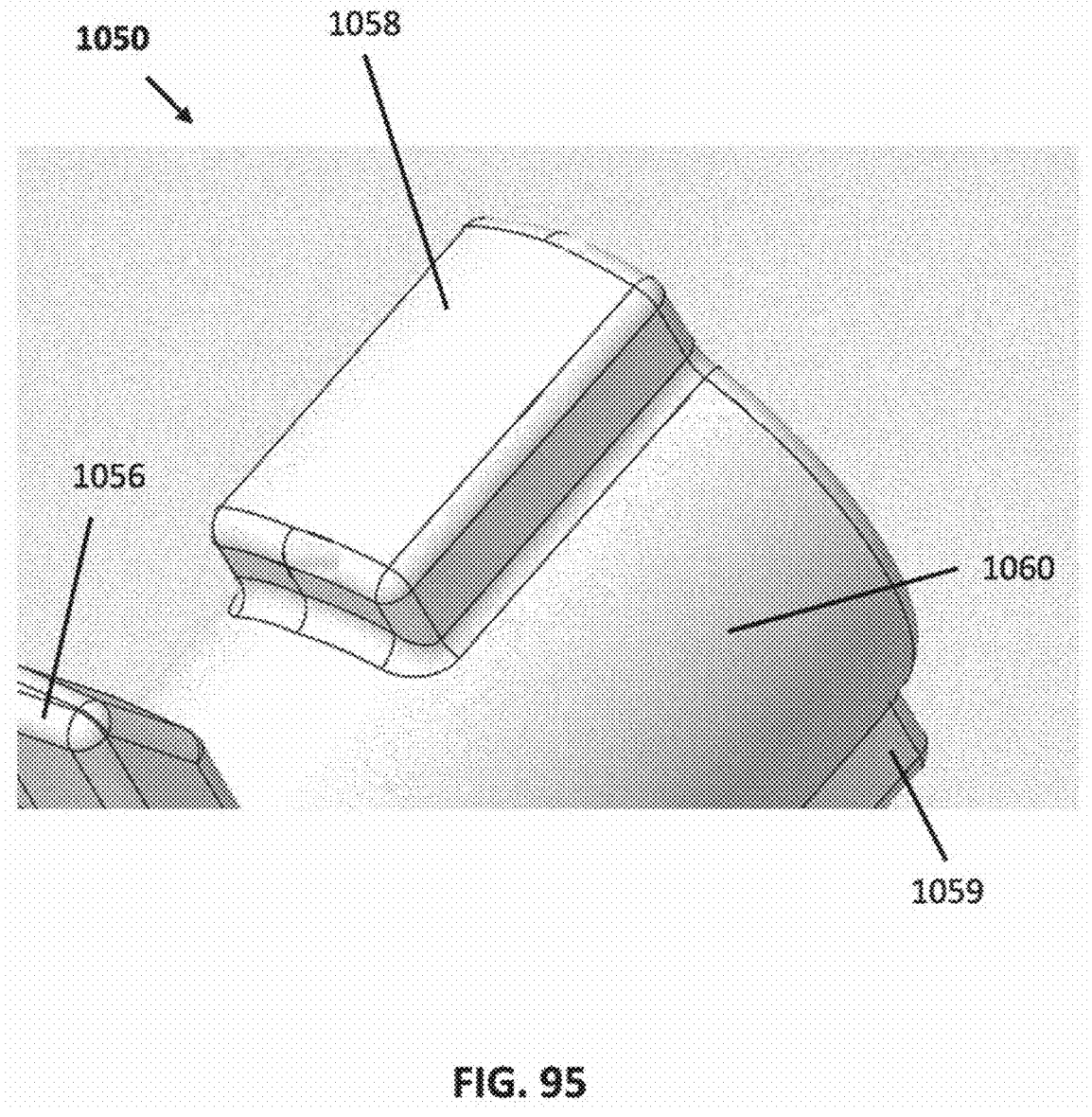
FIG. 95 illustrates an enlarged view of the upper portion of the scaffold neck, according to aspects of the present embodiments.

FIG. 95 illustrates an enlarged view of the neck 1060 on a scaffold 1050, according to aspects of the present embodiments. One retaining pad 1058 is visible in FIG. 95. The retaining pad 1058 has a rectangular prism shape with curved edges, and is disposed on the upper portion of the neck 1060, while another retaining pad 1059 that is partially visible is disposed on the lower portion of the neck 1060. A portion of a retaining tab 1056 is also visible.

Figure 96:
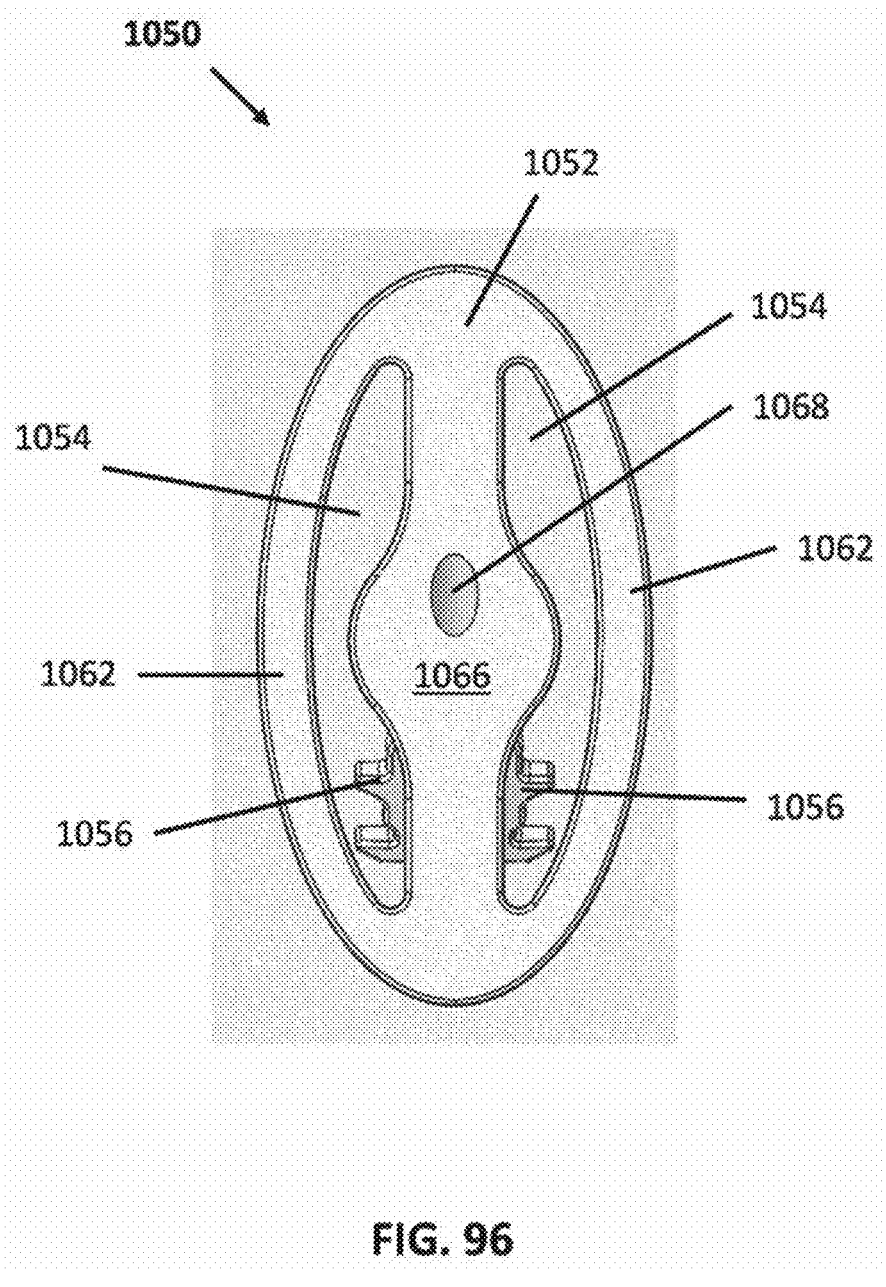
FIG. 96 illustrates a bottom view of a scaffold, according to aspects of the present embodiments.

FIG. 96 illustrates a bottom view of a scaffold 1050, according to aspects of the present embodiments. The base plate 1052 may have curved side portions 1062 and openings 1054, and a central portion 1066. A central opening 1068 into the lumen of the neck 1060 is visible. Two of the retaining tabs 1056 are visible through the openings 1054. In this design, the figuration of the base plate 1052 uses less material than earlier embodiments such as the ones featured in FIGS. 3-5 and 31-32, and may provide certain benefits for manufacturing and/or mechanical flexibility.

Figures 97A, 97B:
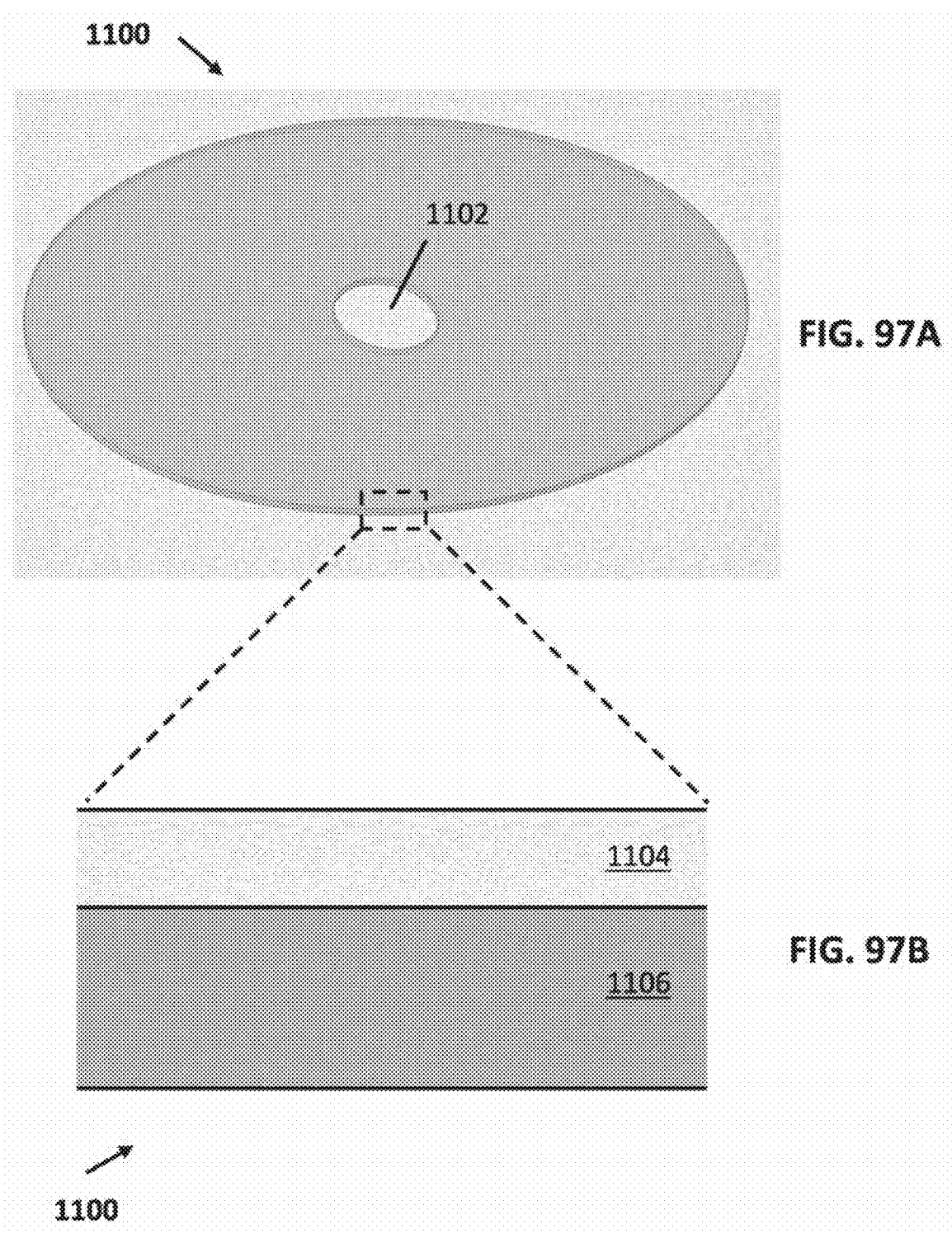
FIG. 97A illustrates a perspective view of a patch, according to aspects of the present embodiments.
FIG. 97B illustrates a cross-sectional view of a patch, according to aspects of the present embodiments.

FIG. 97A illustrates a perspective view of a patch 1100 according to aspects of the present embodiments. The patch 1100 includes an opening 1102 disposed in the center of the patch 1100. The shape of the patch 1100 may be an oval or an ellipse. In some embodiments, the shape of the patch 1100 may preferentially be an oval. The opening 1102 may be an oval, an ellipse, or a circle. The patch 1100 includes at least a flexible, bioabsorbable polymer material.

FIG. 97B illustrates a cross-sectional view of a patch 1100, according to aspects of the present embodiments. In some embodiments, the patch 1100 may include a base layer 1106 that may have a thickness within a range of 190-220 μm, and an electrospun layer 1104 that may have a thickness within a range of 20-80 μm. The total thickness of the patch may be within a range of 210-300 μm.

Figures 98, 99:
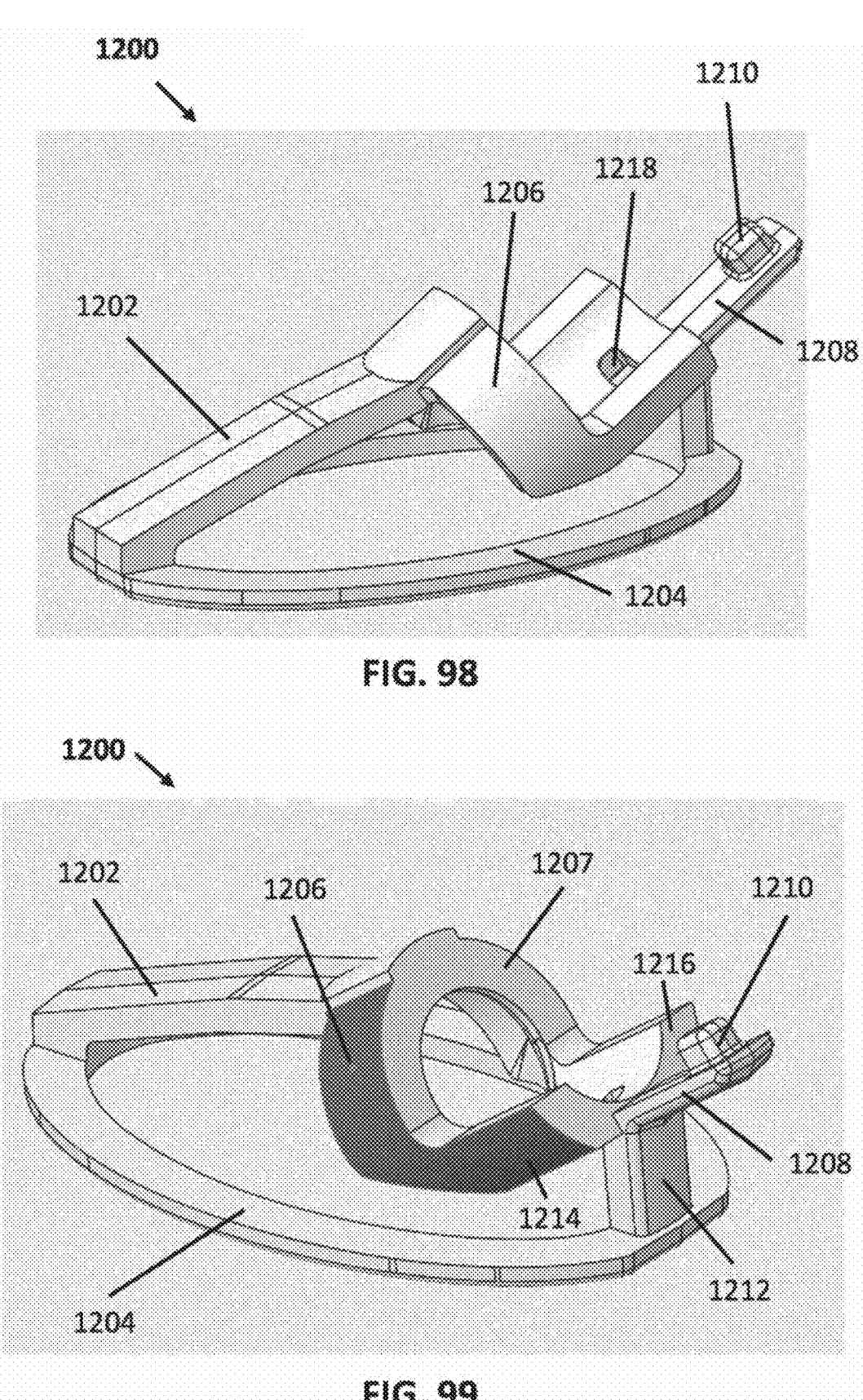
FIG. 98 illustrates a perspective view of an external fixation, according to aspects of the present embodiments.
FIG. 99 illustrates a perspective view of an external fixation, emphasizing the collar portion of the external fixation, according to aspects of the present embodiments.

FIG. 98 illustrates a perspective view of an external fixation 1200, according to aspects of the present embodiments. The external fixation 1200 may include an anterior member or rib 1202 that connects to a base ring portion 1204 and a collar 1206 to provide both support and flexibility such that the overall external fixation 1200 may adapt and conform to various vessel wall morphologies and tissue tract anatomies that are experienced in clinical use. The collar 1206 is shown in more detail in FIG. 99 below.

FIG. 99 illustrates a perspective view of an external fixation 1200, emphasizing the collar 1206 portion of the external fixation 1200, according to aspects of the present embodiments. The collar 1206 has a semicircular portion 1206 with a flat side 1207 that extends into a diagonal portion 1214. From the side view, the collar 1206 connects to the diagonal portion 1214 in an L-like shape. The diagonal portions 1214 on either side of the scaffold 1200 connect together at another flat portion 1216 with has an opening 1218 (see FIG. 98). Overall, the general shape of the collar 1206 resembles a sectioned cylinder. The base ring portion 1204 may form a shape that is an oval, an ellipse, a square, a rectangle, or a diamond, in certain embodiments.

Referring still to FIG. 99 and FIG. 98, a posterior post 1212 rises vertically from the base ring portion 1204, connects to the second flat portion 1216 of the collar 1206, and then turns into a tab 1208 that extends diagonally away from the posterior post 1212. The tab has a protrusion 1210 in the shape of a rectangular prism with rounded edges and corners at the end of the tab 1208. The tab 1208 and protrusion 1210 interact with a delivery shaft 1408 during the delivery of the closure device.

Figure 100:
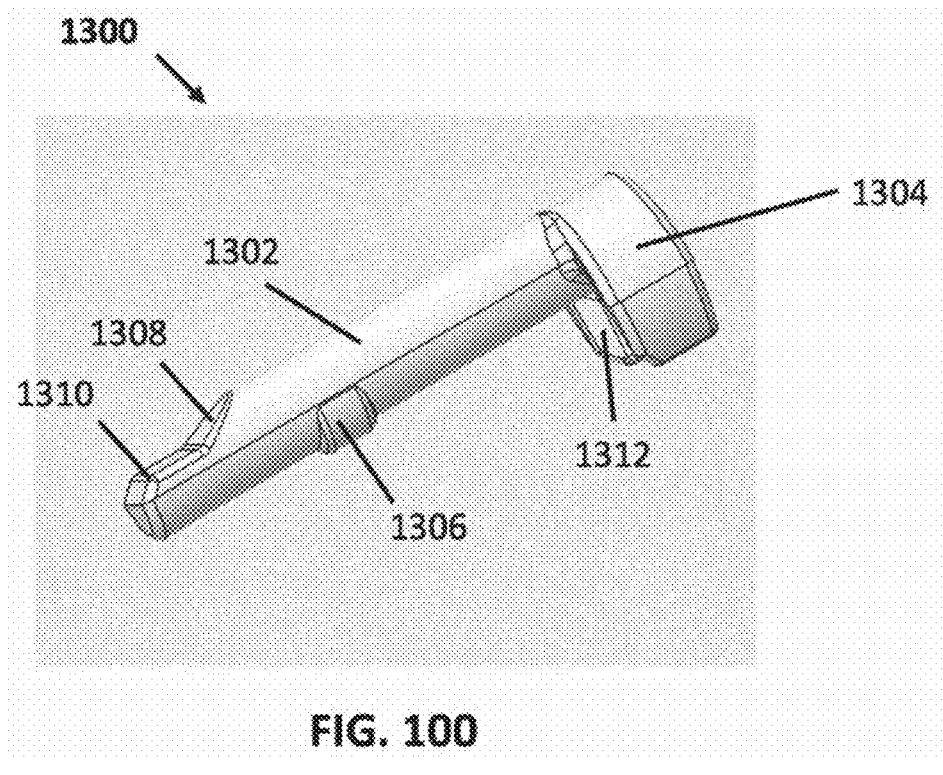
FIG. 100 illustrates a perspective view of a closure pin, according to aspects of the present embodiments.

FIG. 100 illustrates a perspective view of a closure pin 1300, according to aspects of the present embodiments. The closure pin, when used within the closure device, is disposed within the scaffold neck for sealing the lumen of the scaffold. This closure step may occur after a guidewire is removed from the scaffold. The closure pin may include a cylindrical pin body 1302 and a cylindrical or circular pin head 1304 that has a diameter that is larger than the diameter of the cylindrical body 1302 and is connected to the proximal end of the pin body 1302 in an eccentric position. The pin head 1304 includes a rectangular cutout 1312 for interfacing with the protrusion 1210 on the external fixation 1200. The pin 1300 also includes a protrusion 1306 on the pin body 1302 for interfacing with the opening 1218 in the external fixation 1200. At the distal end of the pin 1300, there is an angled portion 1308 and a flat portion 1310 with a reduced diameter.

Figure 101:
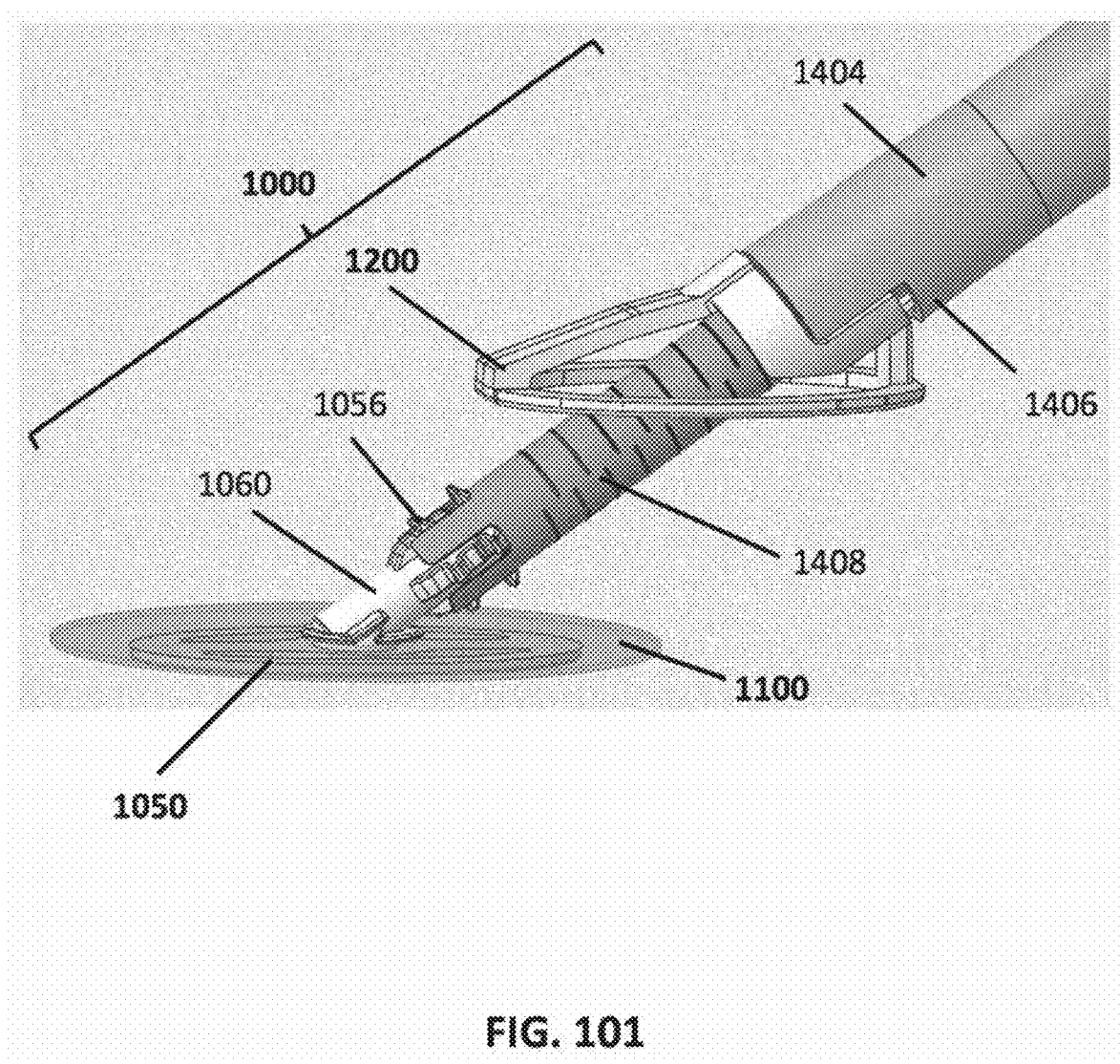
FIG. 101 illustrates a perspective view of a vascular closure device and system with outer shaft engaged with an external fixation, according to aspects of the present embodiments.

FIG. 101 illustrates a perspective view of a vascular closure device 1000 and system with fixation shaft 1404 engaged with an external fixation 1200, according to aspects of the present embodiments. This arrangement shows an example of how the components of the closure device 1000 are assembled during delivery of the closure device 1000. The scaffold 1050 is engaged via the retaining tabs 1056 to the delivery shaft 1408. The patch 1100 is positioned directly above the scaffold 1050 and is engaged at the threaded portion 1073 of the scaffold 1050. The external fixation 1200 is engaged to the fixation shaft 1404 via the L-shaped cylinder-like scaffold neck. The distal end 1406 of the fixation shaft 1404 is shaped to accommodate the L-shaped cylinder-like scaffold neck.

Figure 102:
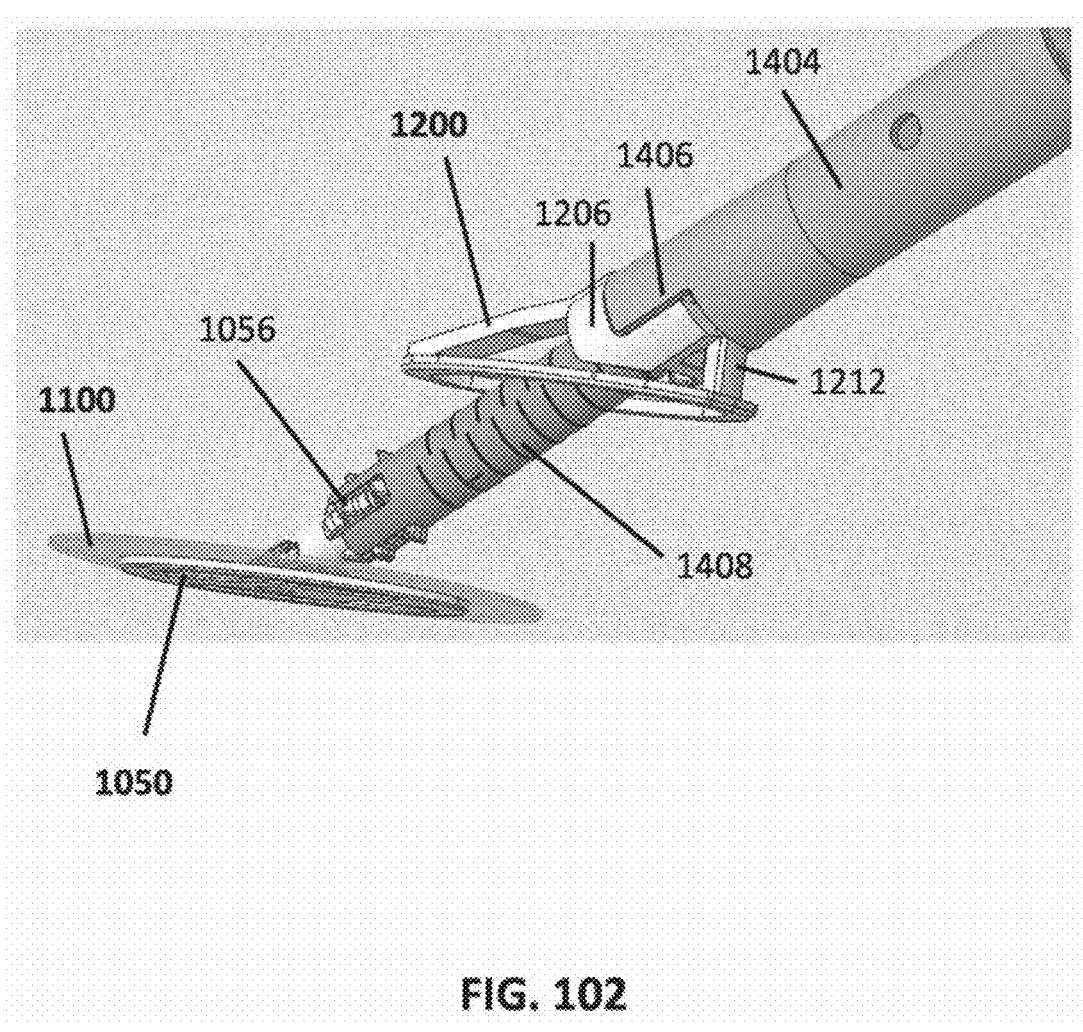
FIG. 102 illustrates a posterior perspective view of a vascular closure device and system with outer shaft engaged with an external fixation, according to aspects of the present embodiments.

FIG. 102 illustrates a posterior perspective view of a vascular closure device 1000 and system with fixation shaft 1404 engaged with an external fixation 1200, according to aspects of the present embodiments. The vertical post 1212 is visible, but the tab 1208 and protrusion 1210 are inside the fixation shaft 1404.

Figure 103:
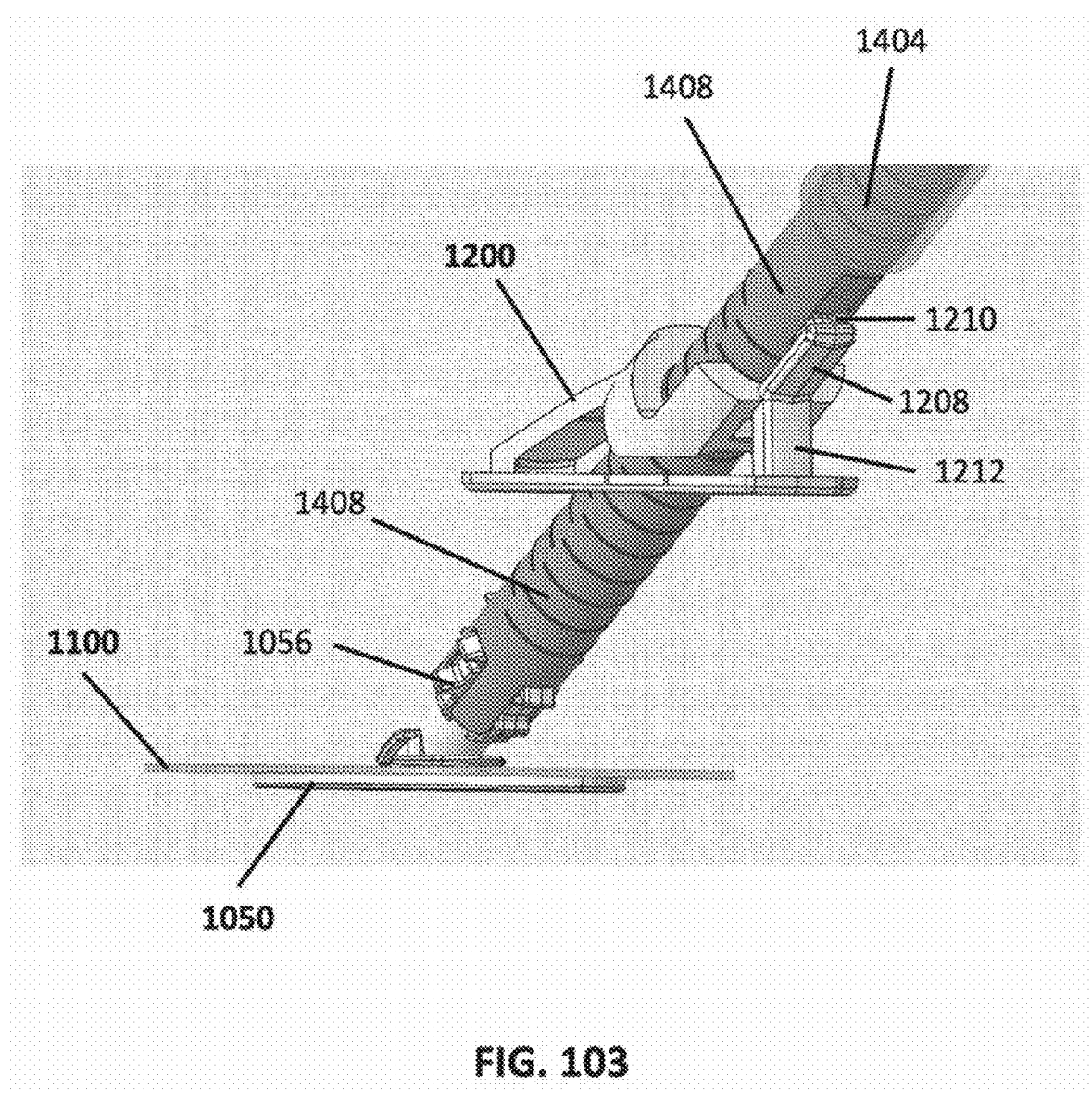
FIG. 103 illustrates a perspective view of a vascular closure device and system with delivery shaft, according to aspects of the present embodiments.

FIG. 103 illustrates a perspective view of a vascular closure device 1000 and system with delivery shaft 1408, according to aspects of the present embodiments. With the fixation shaft 1404 partially retracted, the tab 1208 on the external fixation 1200 is visible. The protrusion 1210 on the external fixation 1200 is engaged with the notch or opening in the delivery shaft 1408.

Figure 104:
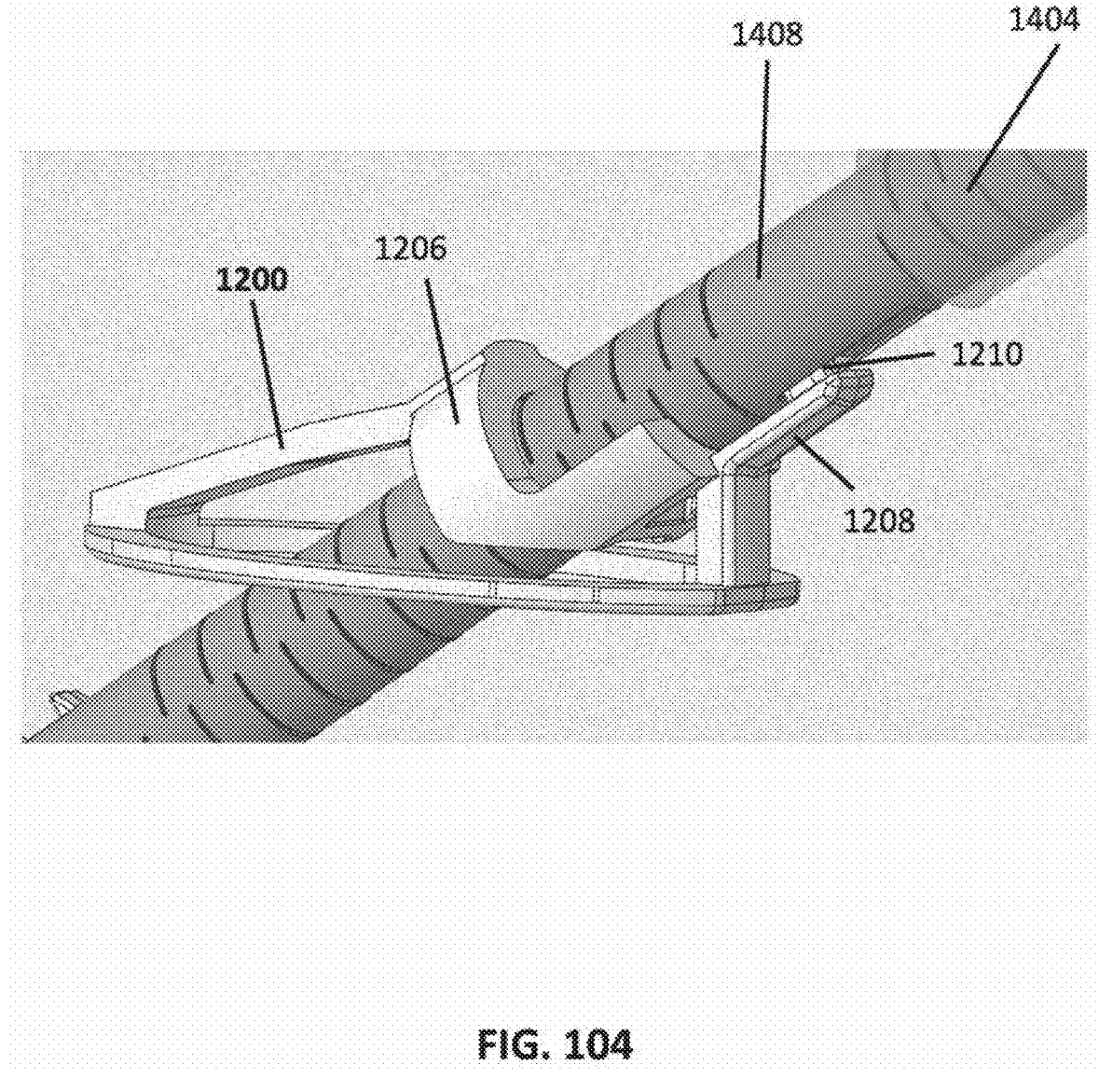
FIG. 104 illustrates a perspective view of a vascular closure device and system with delivery shaft, according to aspects of the present embodiments.

FIG. 104 illustrates a perspective view of a vascular closure device 1000 and system with delivery shaft 1408, according to aspects of the present embodiments. Similar to the view in FIG. 103, the protrusion 1210 on the scaffold 1200 is engaged with a notch in the delivery shaft 1408. The delivery shaft 1408 is disposed through the interior and coaxially with the collar 1206 of the external fixation 1200.

Figure 105:
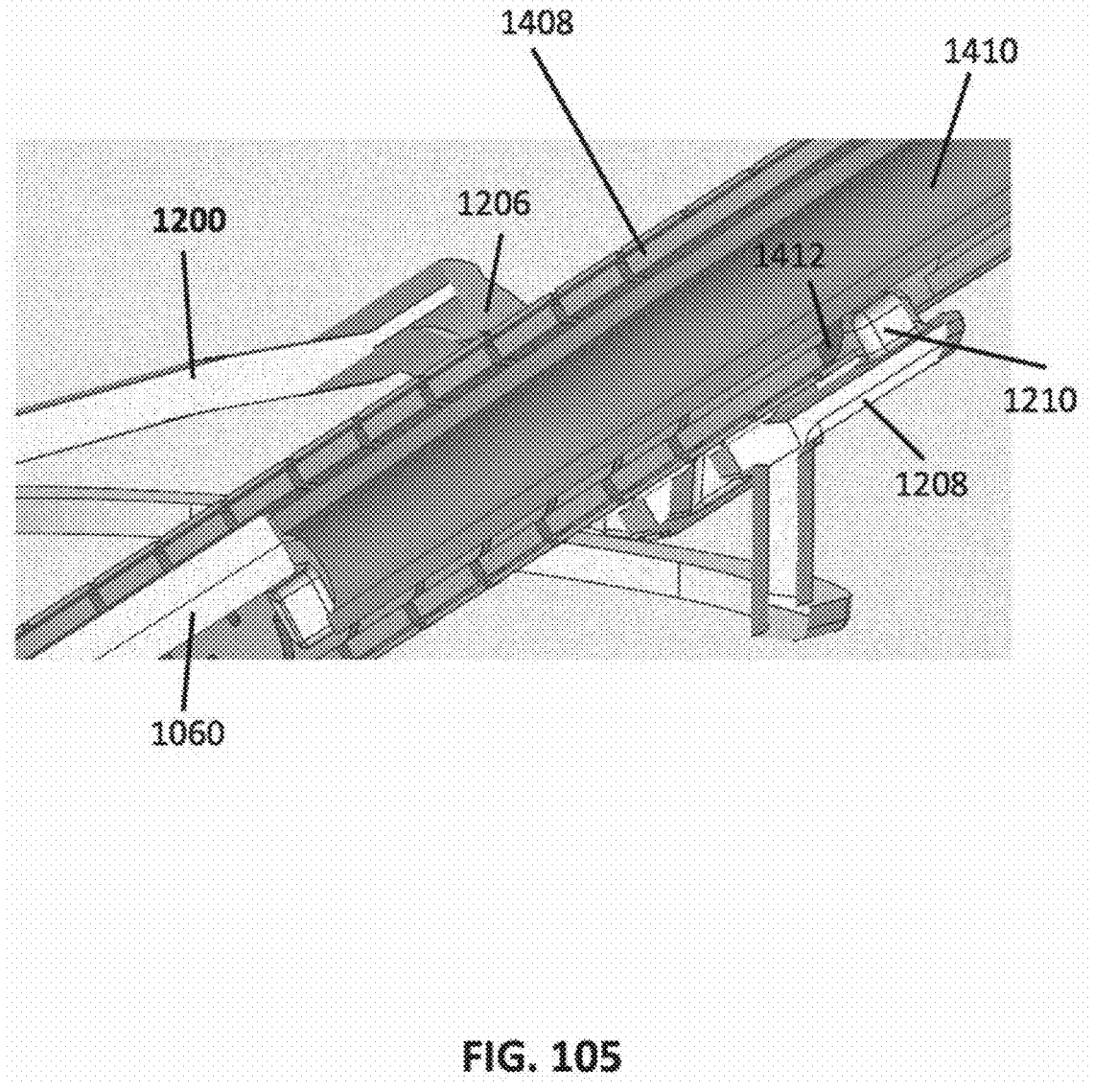
FIG. 105 illustrates a cross-sectional view of a delivery shaft engaged with an external fixation, according to aspects of the present embodiments.

FIG. 105 illustrates a cross-sectional view of a delivery shaft 1408 engaged with an external fixation 1200, according to aspects of the present embodiments. The delivery shaft 1408 passes through the collar 1206 of the external fixation 1200. The push tube 1410 is disposed coaxially within the delivery shaft 1408, and presses against the neck 1060 of the scaffold 1050. An interior lip 1412 presses against the protrusion 1210 during the retraction steps to disengage the delivery system from the closure device 1000.

Figure 106:
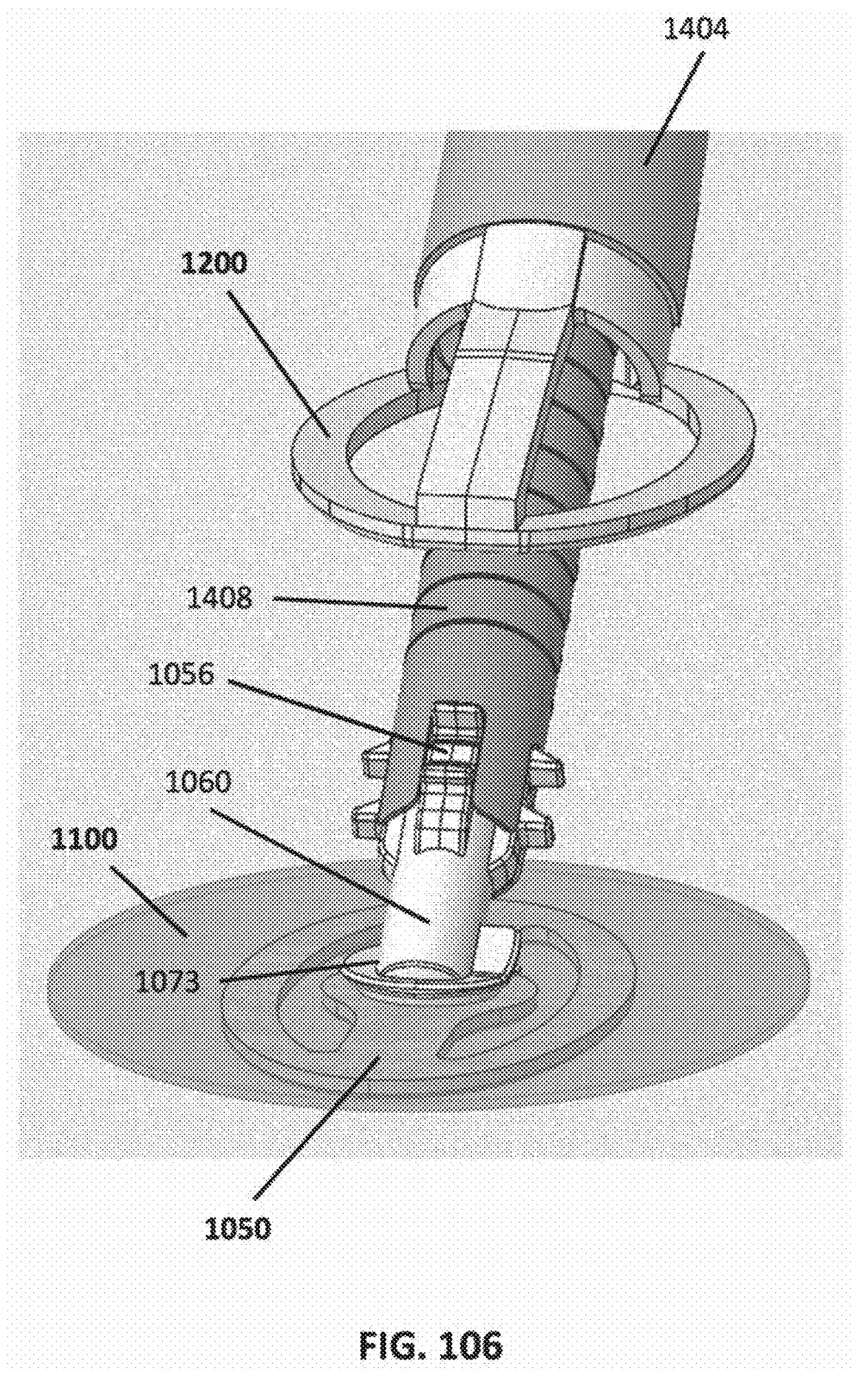
FIG. 106 illustrates a front perspective view of a vascular closure device and system with delivery shaft, according to aspects of the present embodiments.

FIG. 106 illustrates a front perspective view of a vascular closure device 1000 and system with delivery shaft 1408 and fixation shaft 1404, according to aspects of the present embodiments. In this arrangement, the external fixation 1200 is not yet engaged with the scaffold 1050.

Figure 107:
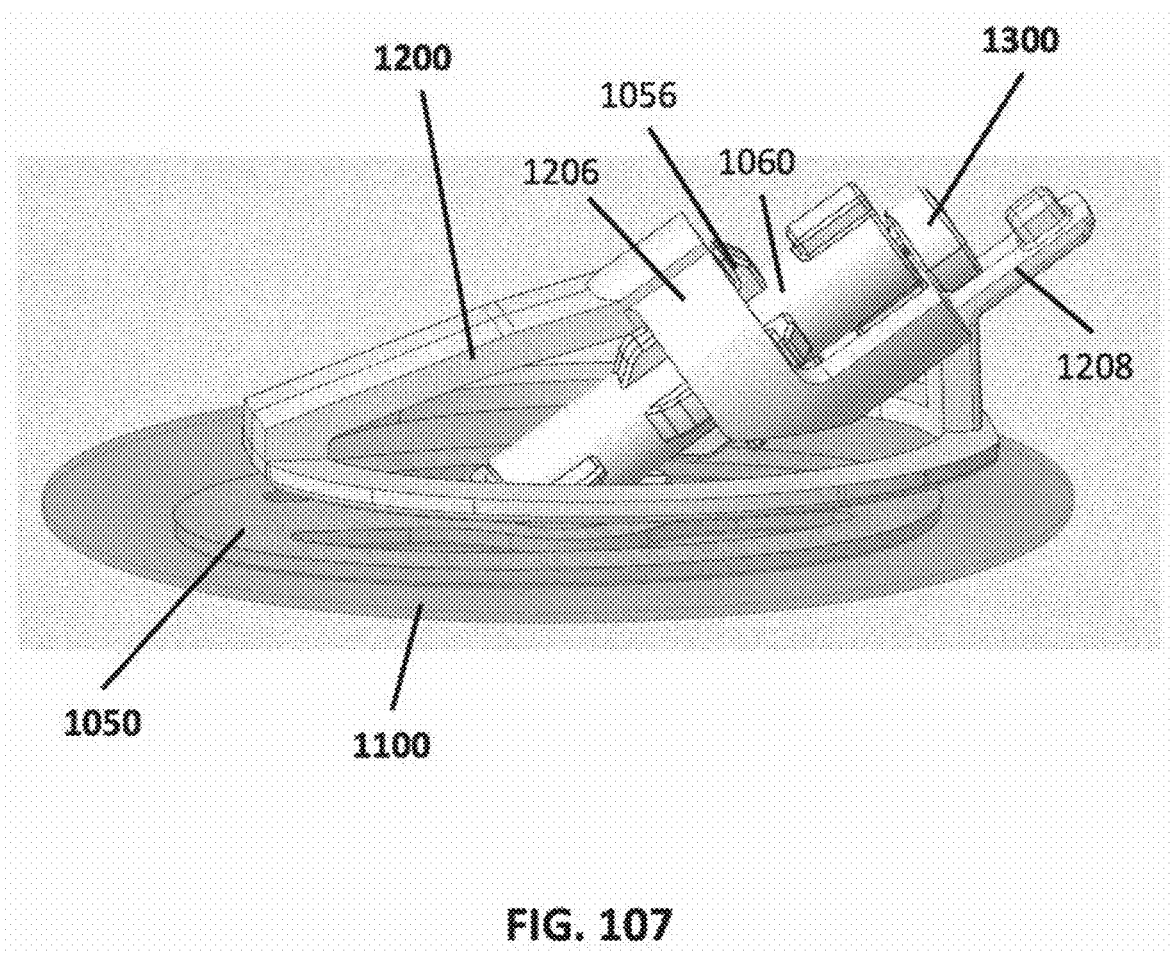
FIG. 107 illustrates a perspective view of an assembled vascular closure device, according to aspects of the present embodiments.

FIG. 107 illustrates a perspective view of an assembled vascular closure device 1000, according to aspects of the present embodiments. In this assembled configuration, the external fixation 1200 is engaged with the scaffold 1050 by insertion of the scaffold neck 1060 through the collar 1206 of the external fixation 1200. The retaining tabs 1056 help hold the external fixation in position so that the wall of the vessel where the opening is being closed and the patch 1100 are clamped between the base ring of the external fixation 1200 and the base plate of the scaffold 1050. The closure pin 1300 is inserted into the opening in the neck 1060 of the scaffold, and helps to close the opening in the neck 1060 after the removal of the guidewire 1001.

Figure 108:
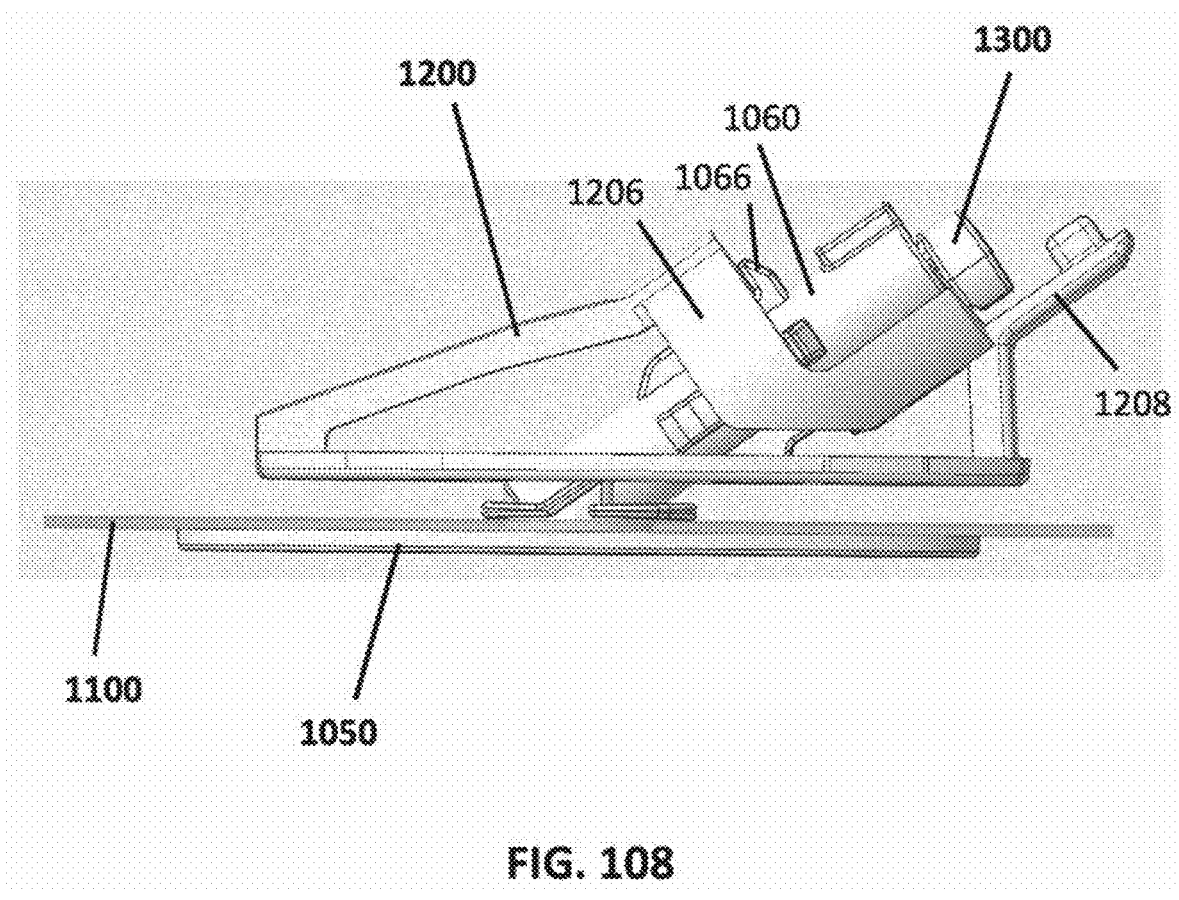
FIG. 108 illustrates a side view of an assembled vascular closure device, according to aspects of the present embodiments.

FIG. 108 illustrates a side view of an assembled vascular closure device, with an external fixation 1200 in a higher position, according to aspects of the present embodiments. The first protrusion 1066 of the retaining tab 1056 is engaged with the collar 1206 of the external fixation 1200. This arrangement is also illustrated in a perspective view in FIG. 110.

Figure 109:
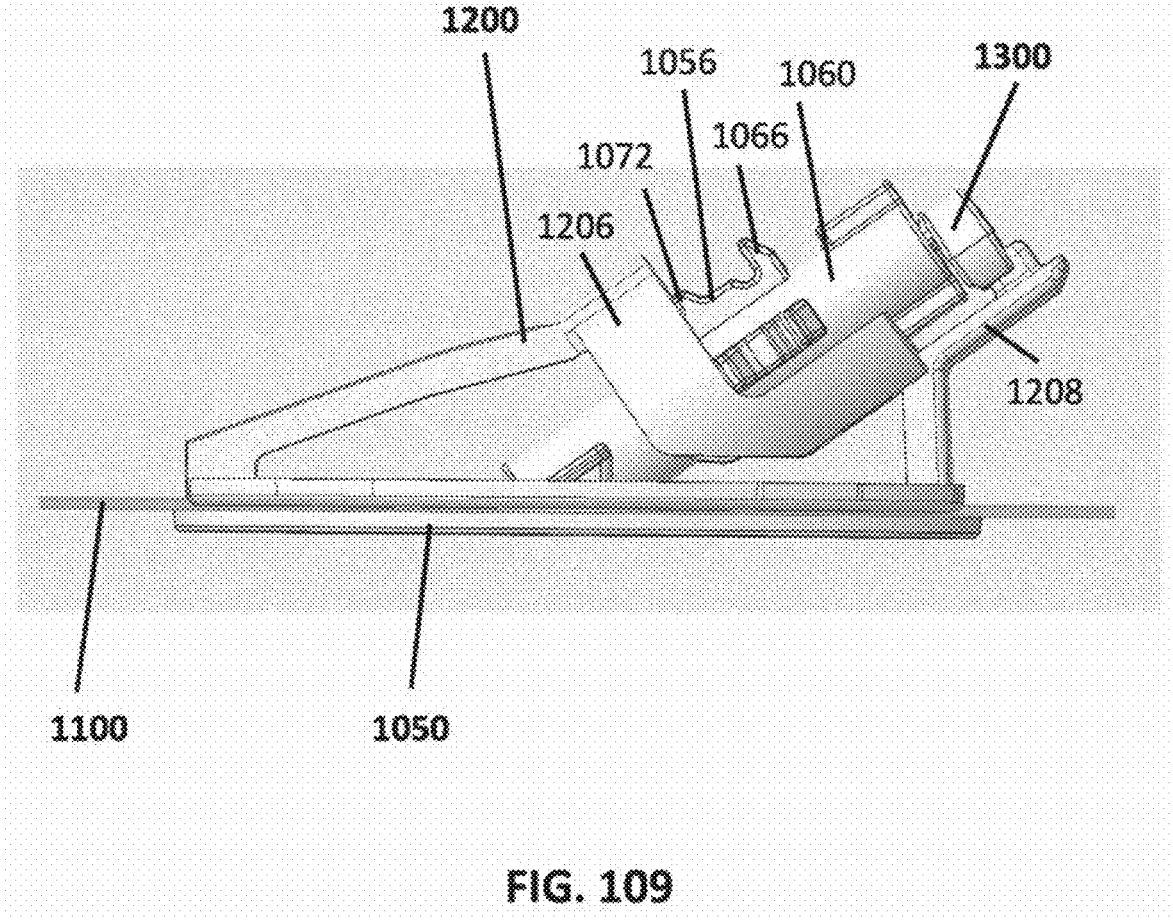
FIG. 109 illustrates a side view of an assembled vascular closure device, according to aspects of the present embodiments.

FIG. 109 illustrates a side view of an assembled vascular closure device, with an external fixation 1200 in a lower position, according to aspects of the present embodiments. The second protrusion 1072 of the retaining tab 1056 is engaged with the collar 1206 of the external fixation 1200, so that the external fixation 1200 is closer to the patch 1100 and base plate of the scaffold 1050.

Figure 110:
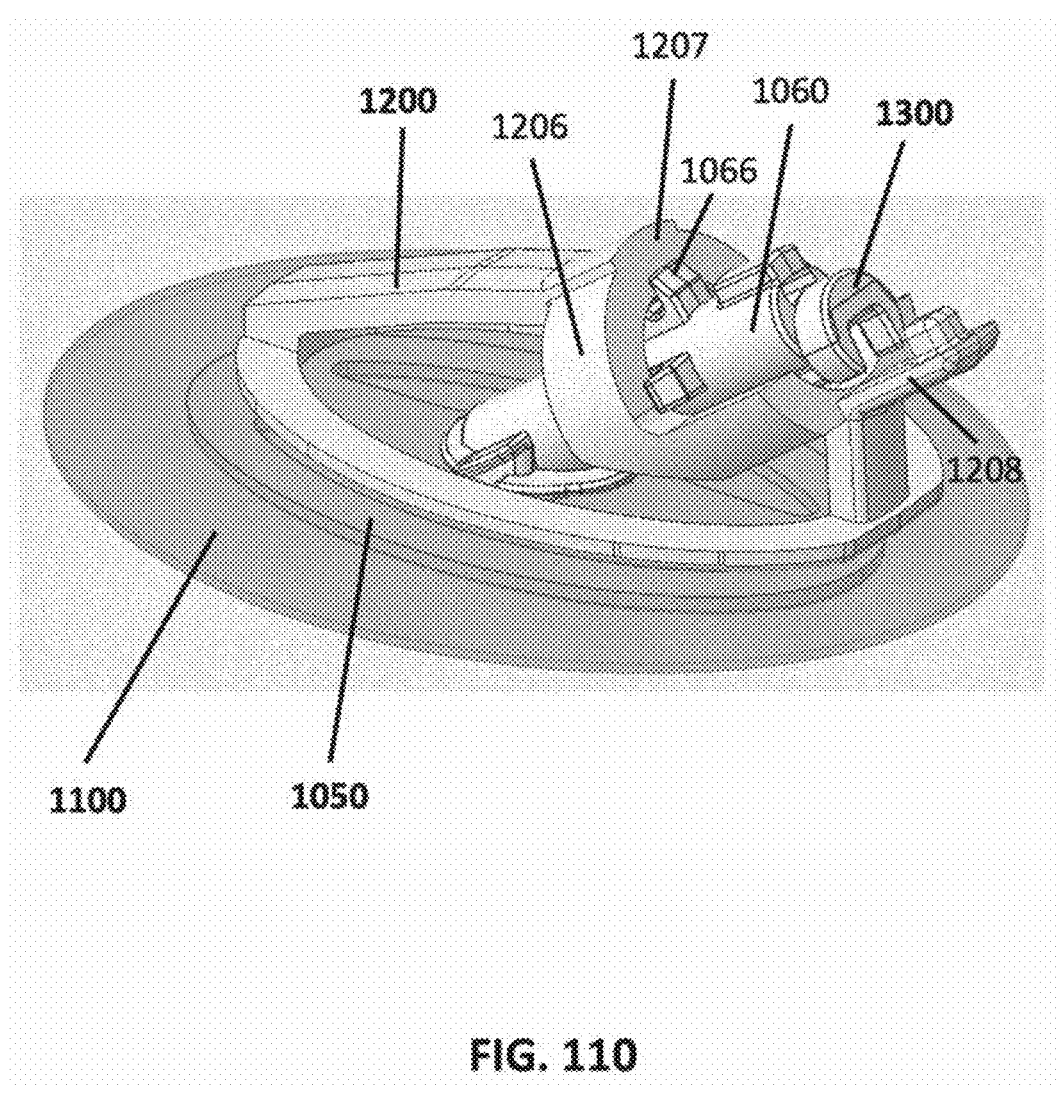
FIG. 110 illustrates a posterior perspective view of an assembled vascular closure device, according to aspects of the present embodiments.

FIG. 110 illustrates a posterior perspective view of an assembled vascular closure device 1000, according to aspects of the present embodiments. The first protrusion 1066 of the retaining tab 1056 is engaged with the collar 1206 of the external fixation 1200, more specifically the protrusion 1066 is essentially hooked on the flat surface 1207. This arrangement is also illustrated in a side view in FIG. 108.

Deployment of Closure Device Using Delivery System with Handle

FIG. 111A through 111L illustrate sequential steps in deployment of a closure device 1000 in a body vessel, according to aspects of the present embodiments. These figures all illustrate the interior view of the lumen 1403 of a body vessel 1401 with an aperture 1405 that is to be closed by the closure device 1000. An introducer sheath 1518 is visible in FIG. 111A through FIG. 111K. The introducer is inserted into a surgical opening of the patient near the aperture 1405 in the body vessel that is to be closed by the closure device 1000.

Figure 111A:
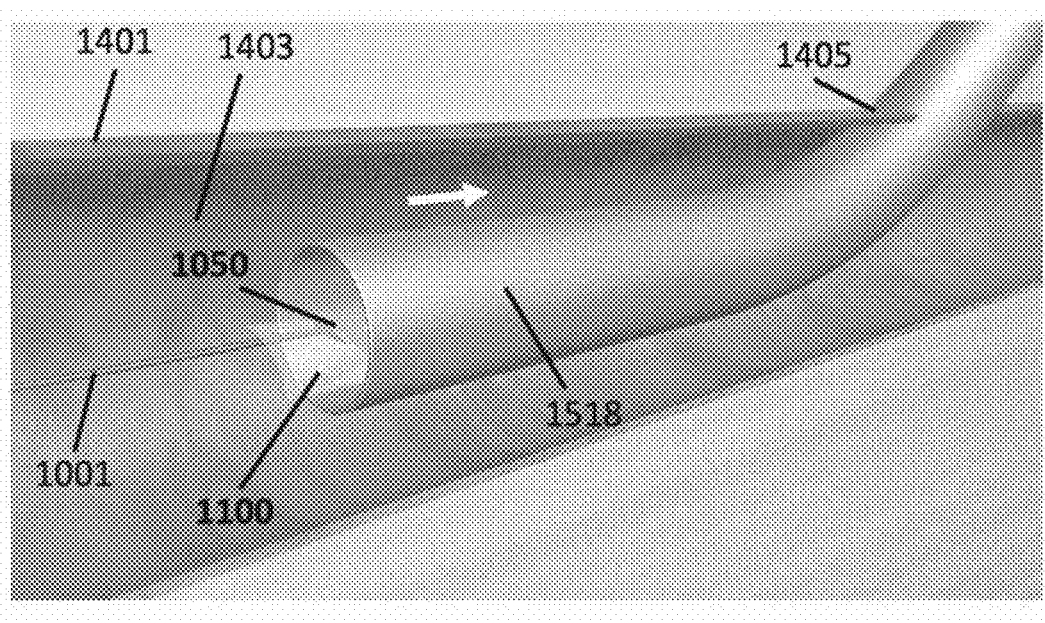
FIG. 111A through 111L illustrate interior views in a body vessel or vessel interior showing sequential steps in deployment of a closure device, according to aspects of the present embodiments.

In FIG. 111A, a guidewire 1001 is disposed through an introducer sheath 1518 and the lumen 1403, and through the rolled interior of a patch 1100. The patch 1100 and scaffold 1050 are visible in their stowed positions within the introducer sheath 1518. During step 1606 of the delivery method 1600 (shown in FIG. 116), the introducer sheath 1518 is retracted pull away from the stowed patch 1100 and scaffold 1050.

Figure 111B:
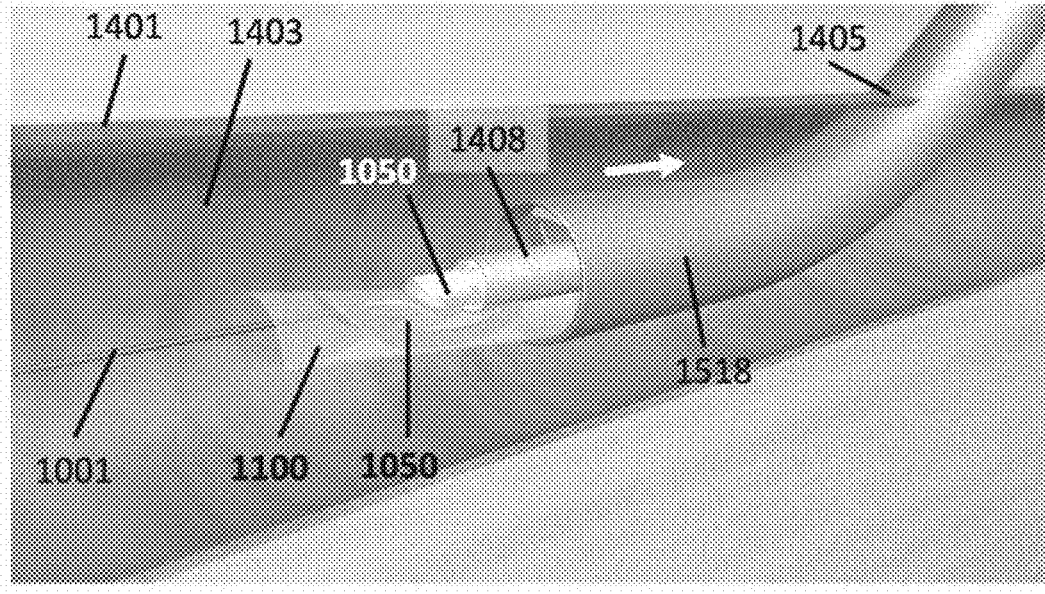

In FIG. 111B, the introducer sheath 1518 continues being retracted, and more of the patch 1100 and scaffold 1050 are visible outside of the introducer sheath 1518.

Figure 111C:
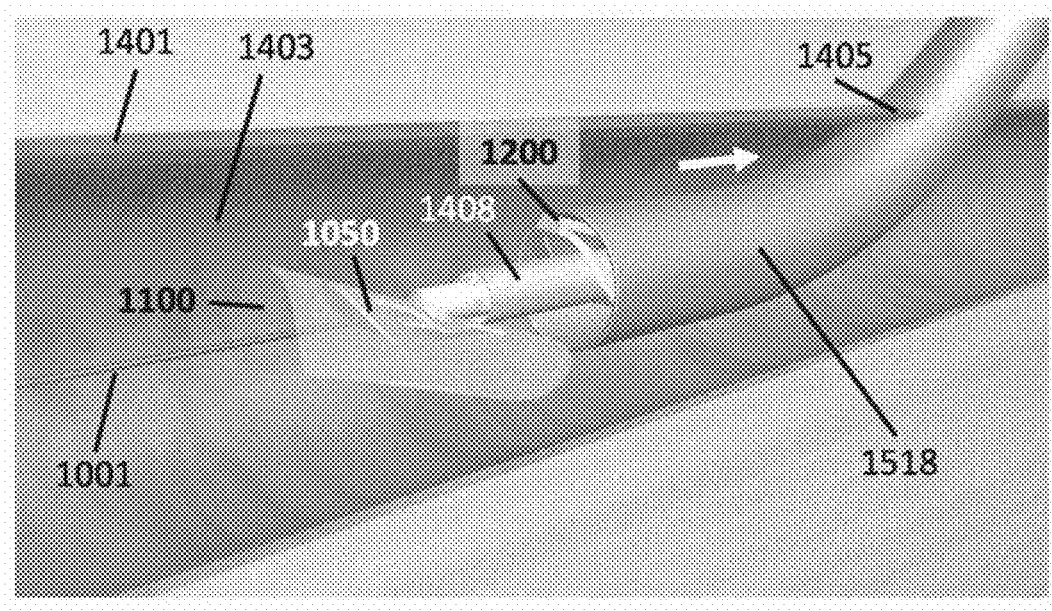

In FIG. 111C, the patch 1100 and scaffold 1050 are completely out of the introducer sheath 1518 and the external fixation 1200 is visible at the entrance of the introducer sheath 1518.

Figure 111D:
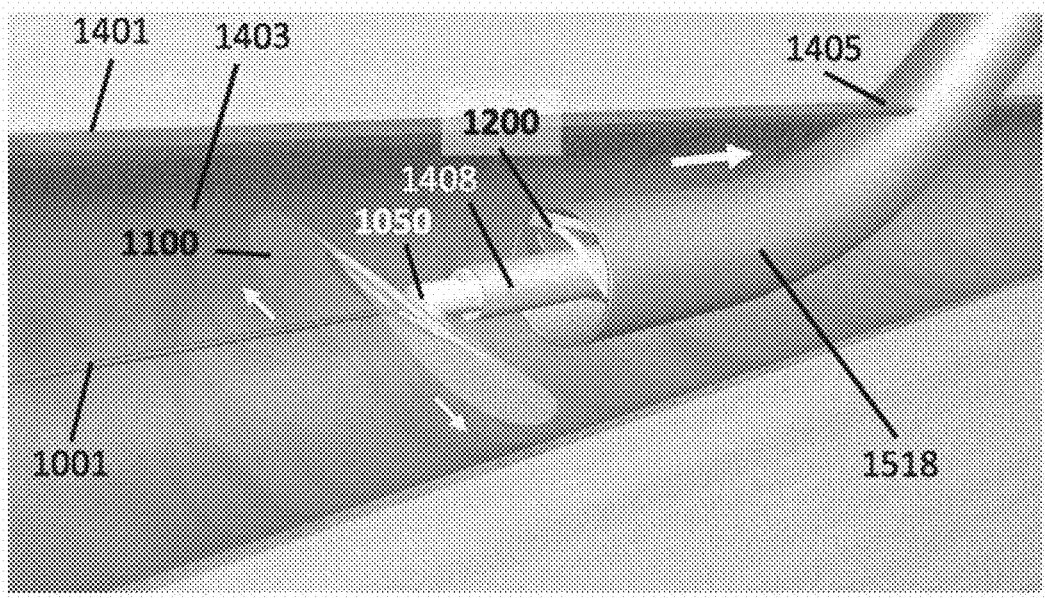

In FIG. 111D, the patch 1100 and scaffold 1050 are unrolled, and become generally flat.

Figures 111E, 111F:
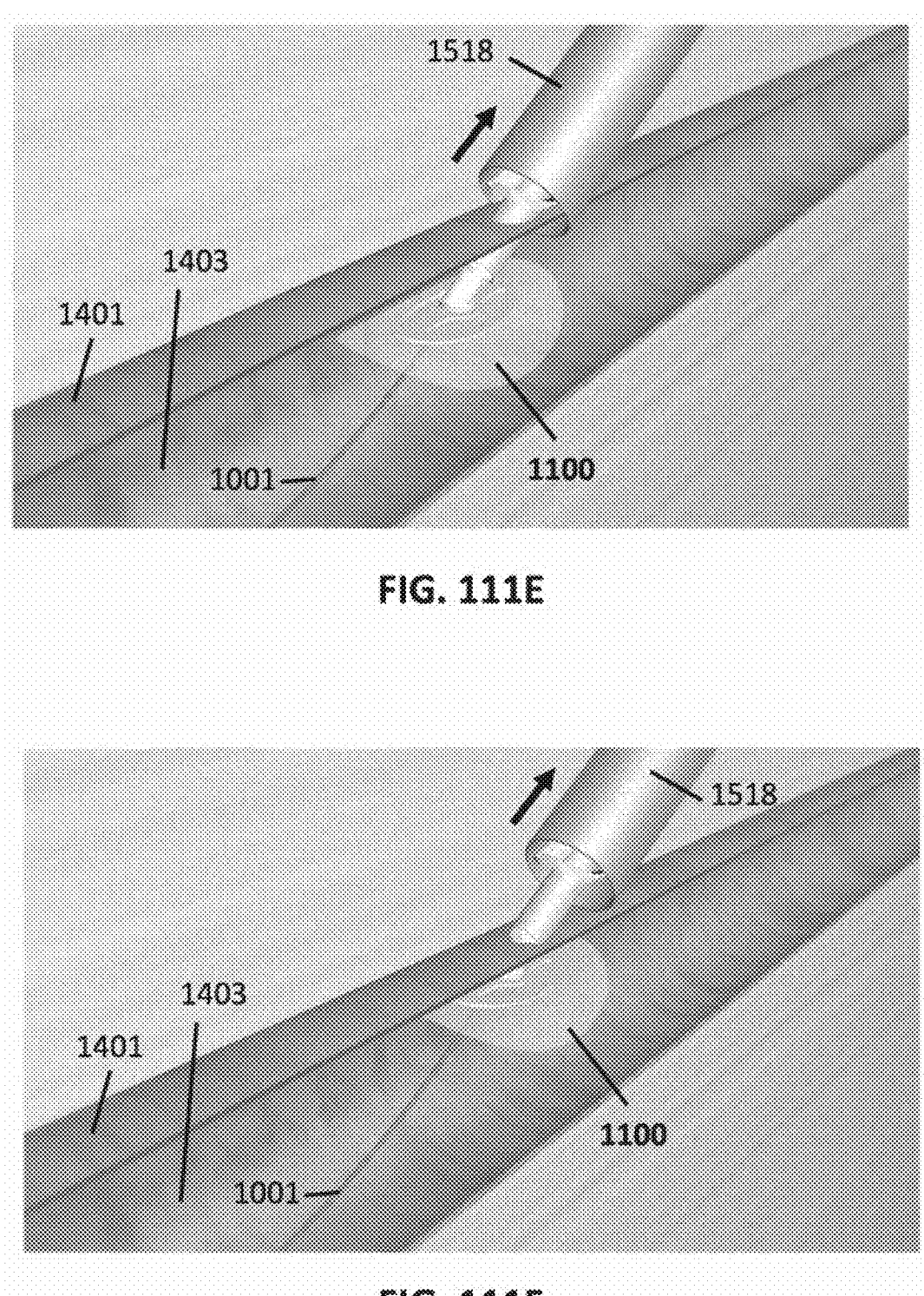

In FIG. 111E and 111F, the delivery device is pulled outward so that the patch 1100 and scaffold 1050 move toward the wall 1401 of the vessel until the top surface of the patch 1100 is in contact with the interior of the wall 1401 (in FIG. 111F).

Figures 111G, 111H:
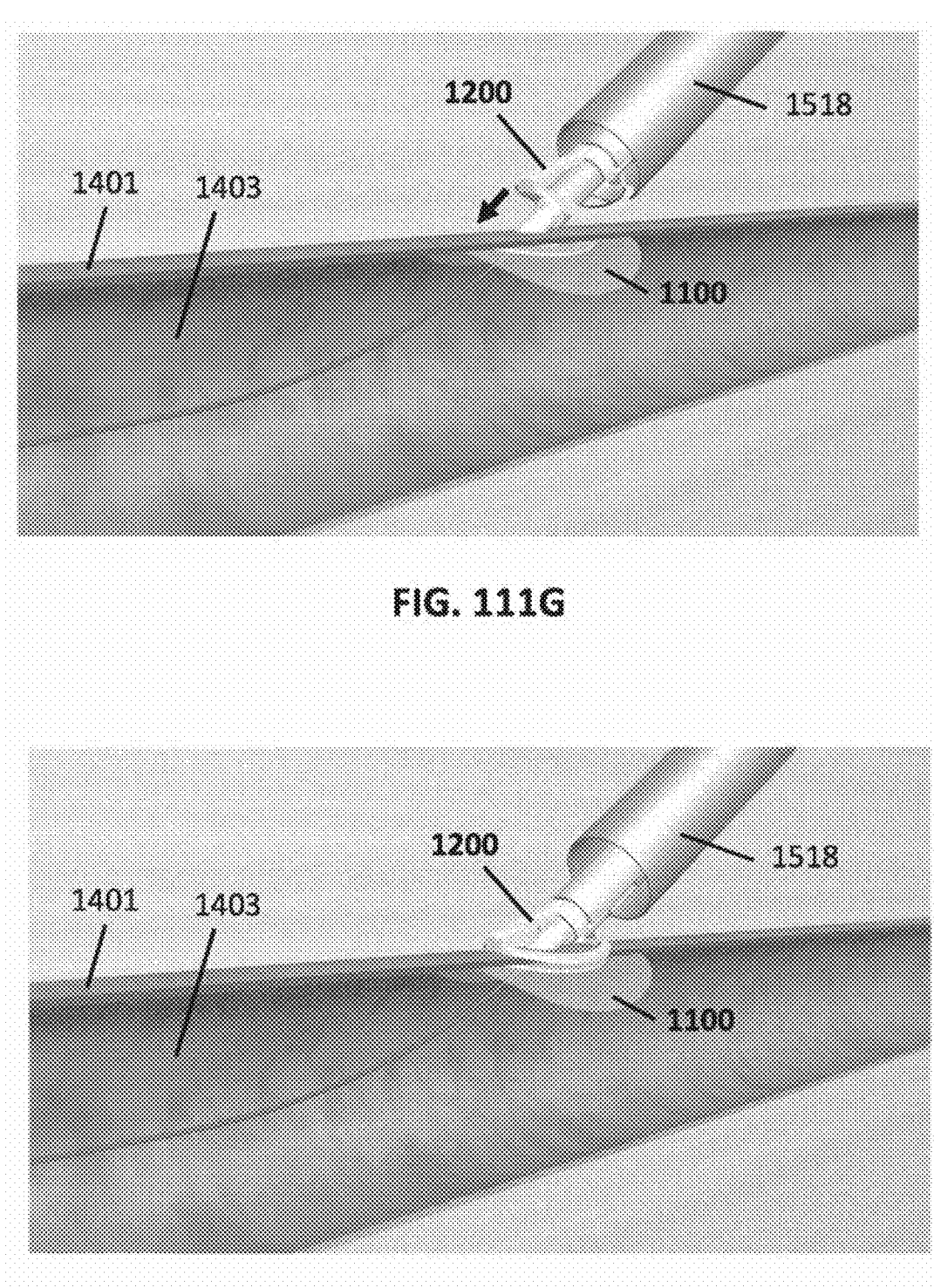

In FIG. 111G, while the patch 1100 and scaffold 1050 are in contact with the interior of the wall 1401, the external fixation 1200 is pushed toward the exterior of the vessel wall 1401 by the fixation shaft 1404.

In FIG. 111H, the external fixation 1200 is in contact with the exterior of the vessel wall 1401. The external fixation 1200 engages with the scaffold 1050.

Figure 111I:
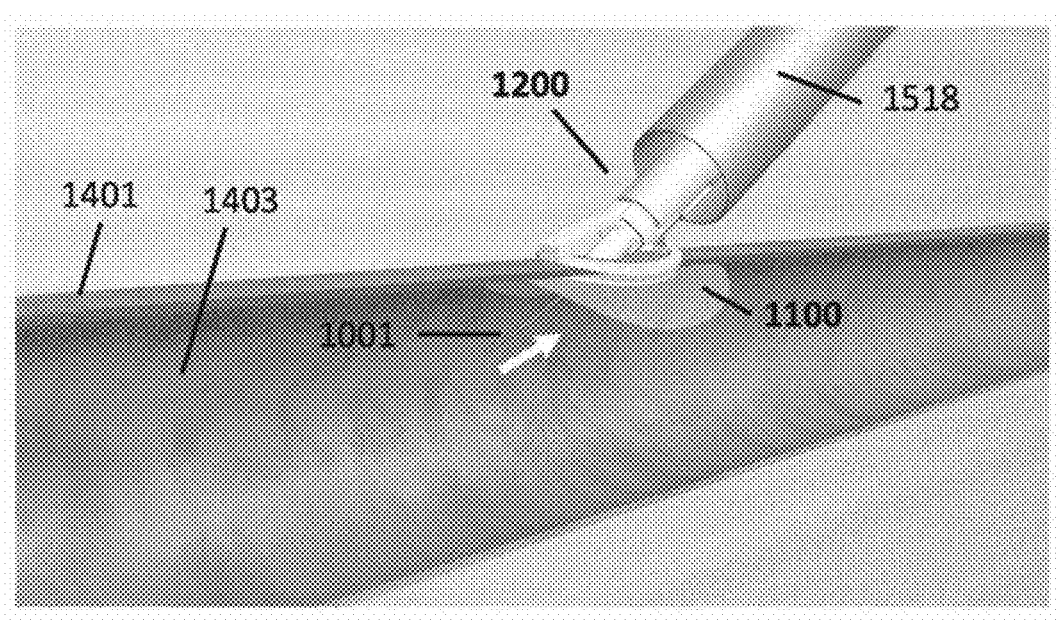
Figure 111J:
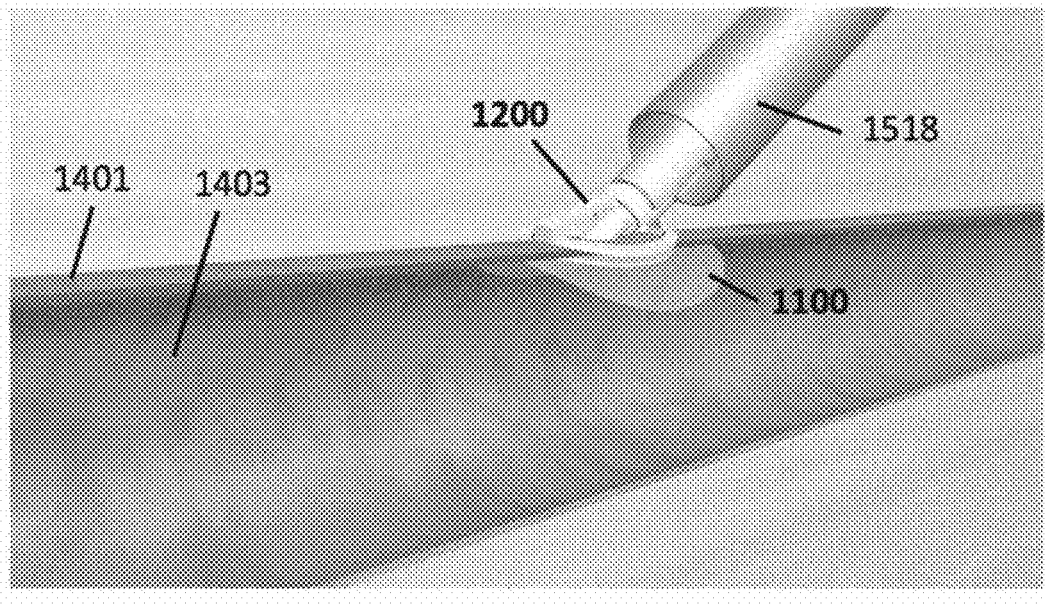

In FIG. 111I, the guidewire 1001 is being retracted. In FIG. 111J the guidewire is fully retracted and no longer visible in the lumen 1403 of the vessel.

Figure 111K:
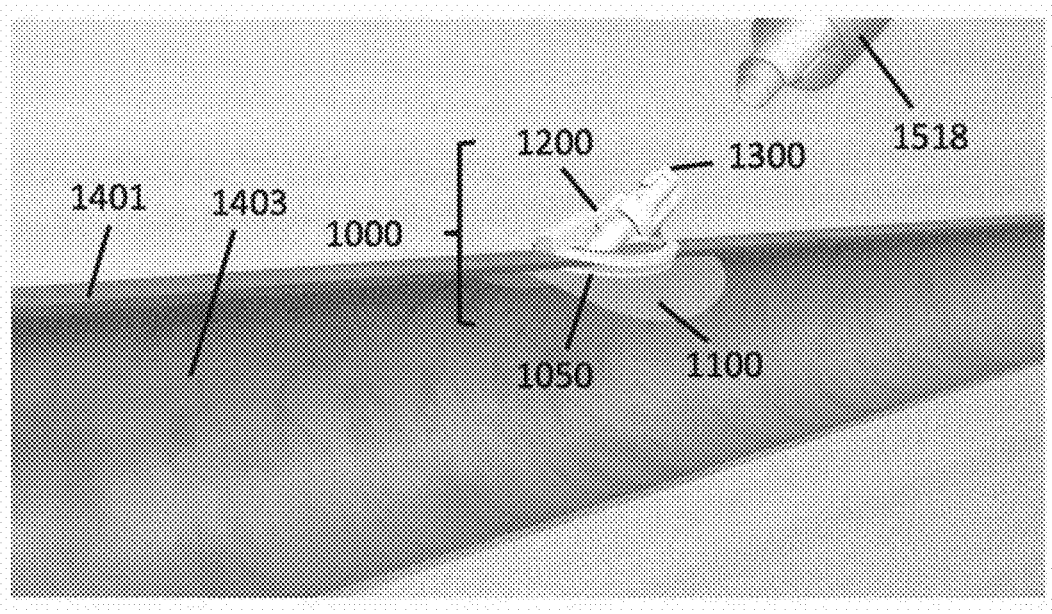

In FIG. 111K, the delivery system is disengaged from closure device 1000, and is moving away.

Figure 111L:
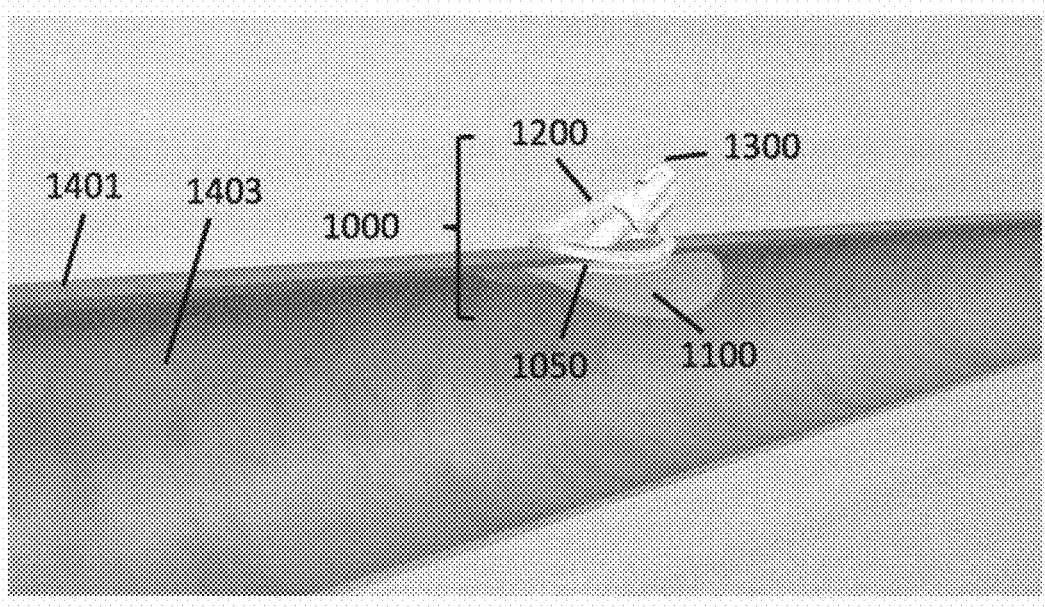

In FIG. 111L, the delivery system is fully removed from the body, and the closure device 1000 remains deployed at the vessel opening site. The patch 1100 is held at the aperture against the vessel wall 1401, sandwiched between the scaffold 1050 and external fixation 1200 which are engaged together, with the closure pin 1300 engaged to close the interior lumen 1064 of the scaffold neck 1060.

Figure 112A:
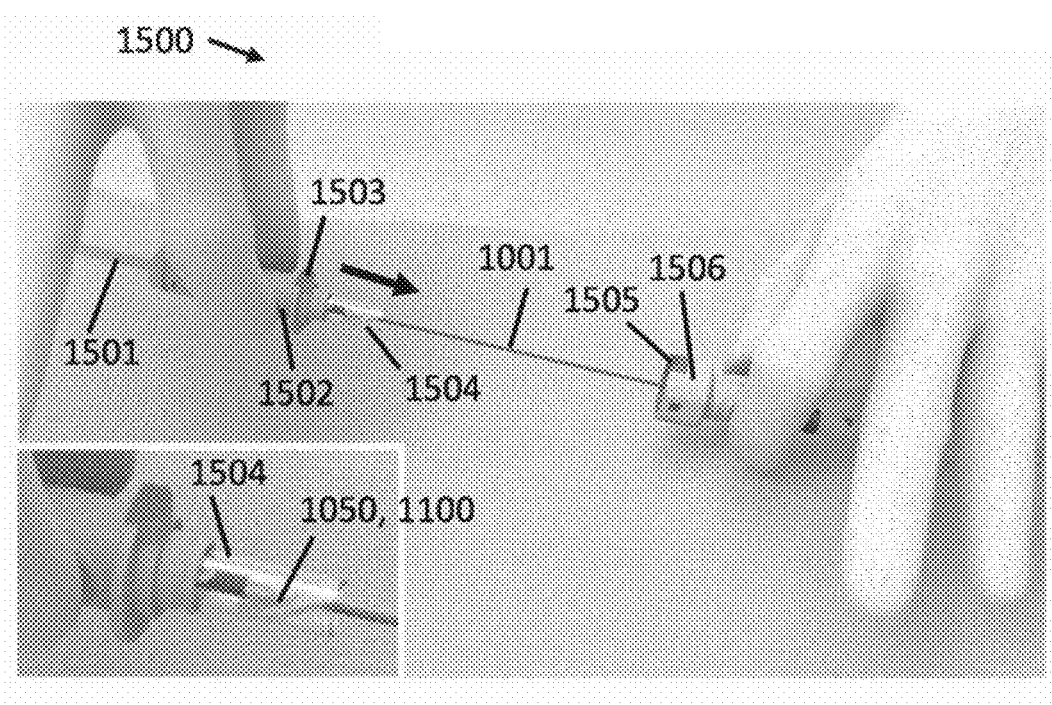
FIG. 112A through 112R illustrate views of a delivery system handle showing sequential steps in deployment of a closure device, according to aspects of the present embodiments.
Figure 112B:
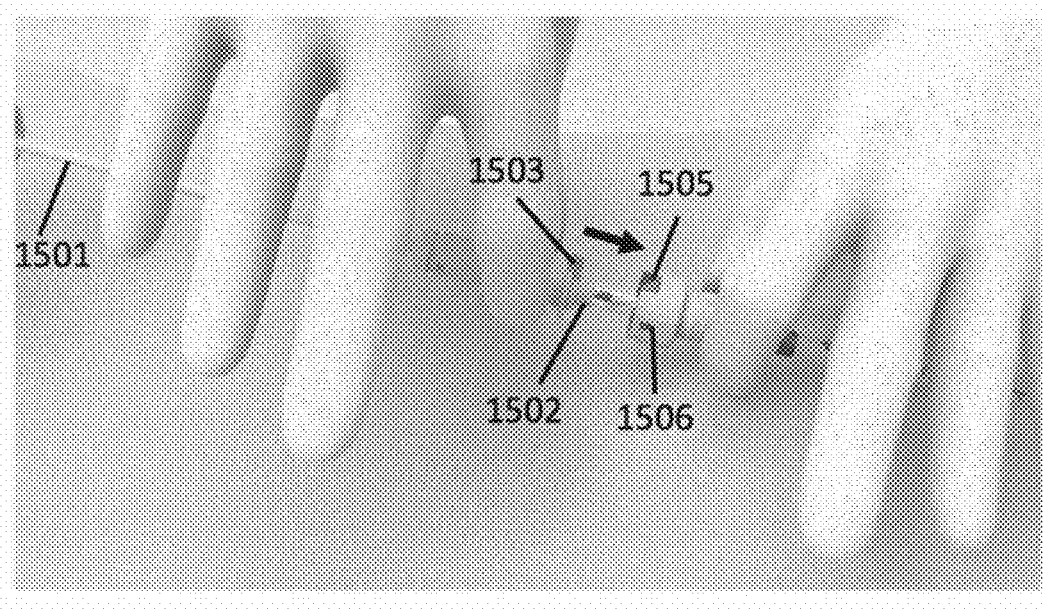
FIG. 112S illustrates a perspective view of the exterior of a delivery system handle, according to aspects of the present embodiments.
FIG. 112T and 112U illustrate views of a delivery system handle near a handle front cap, according to aspects of the present embodiments.
Figure 112C:
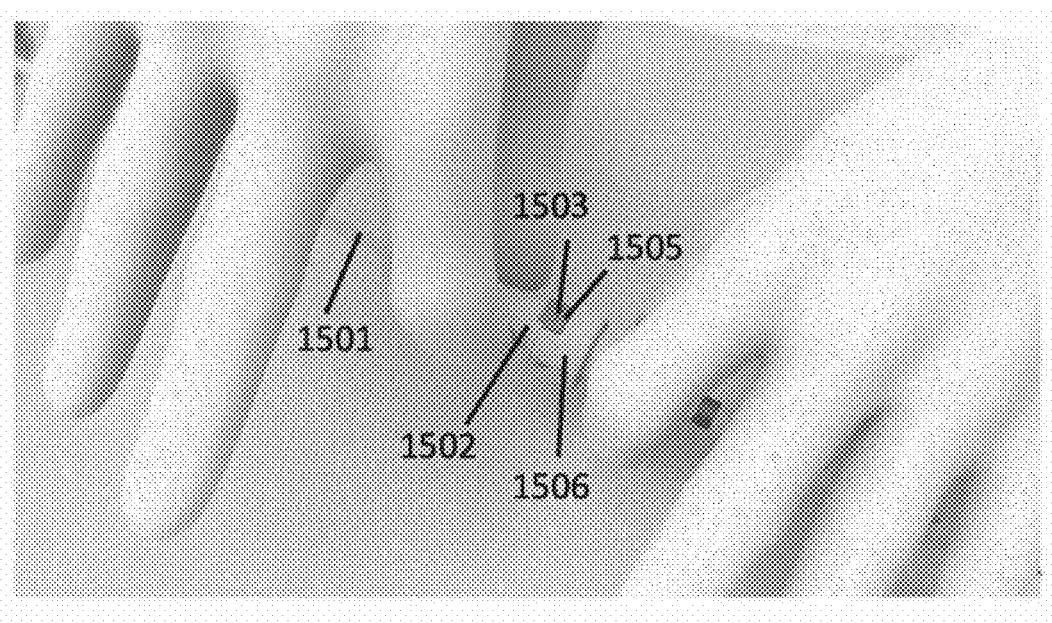
Figure 112D:
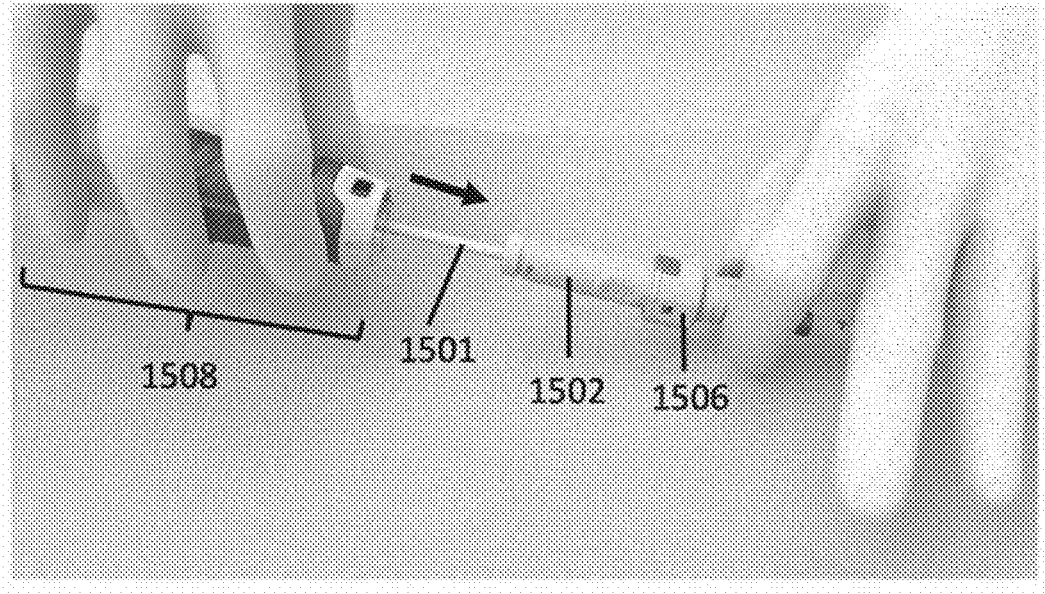
Figure 112E:
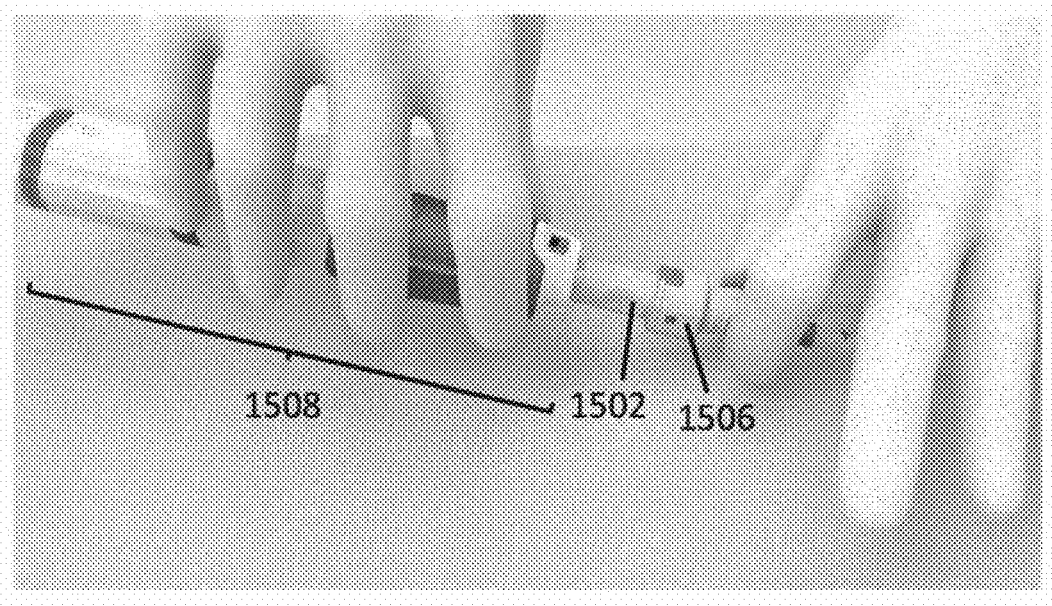
Figure 112F:
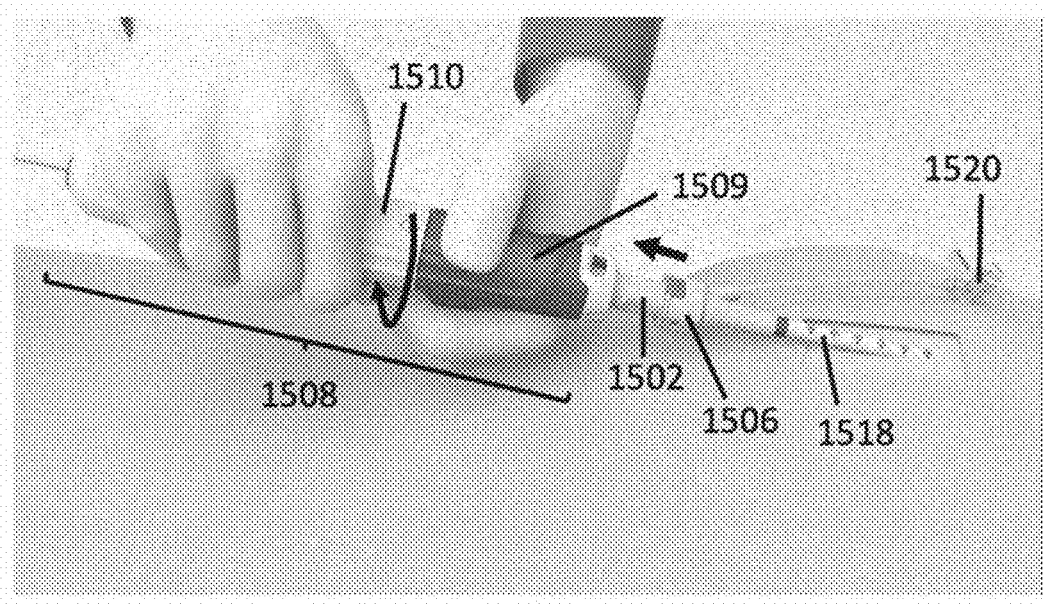
Figure 112G:
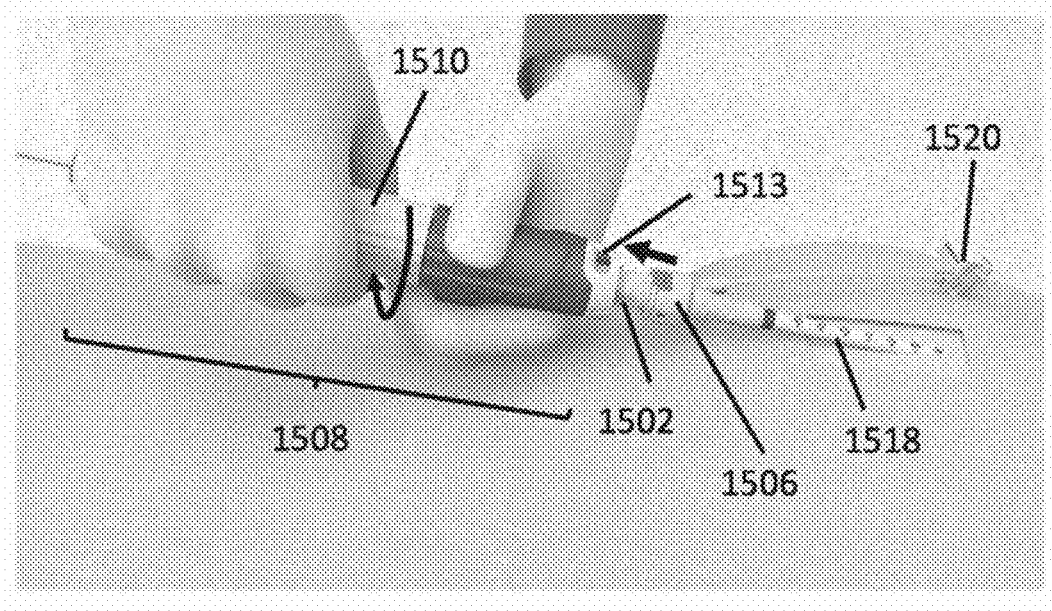
Figure 112H:
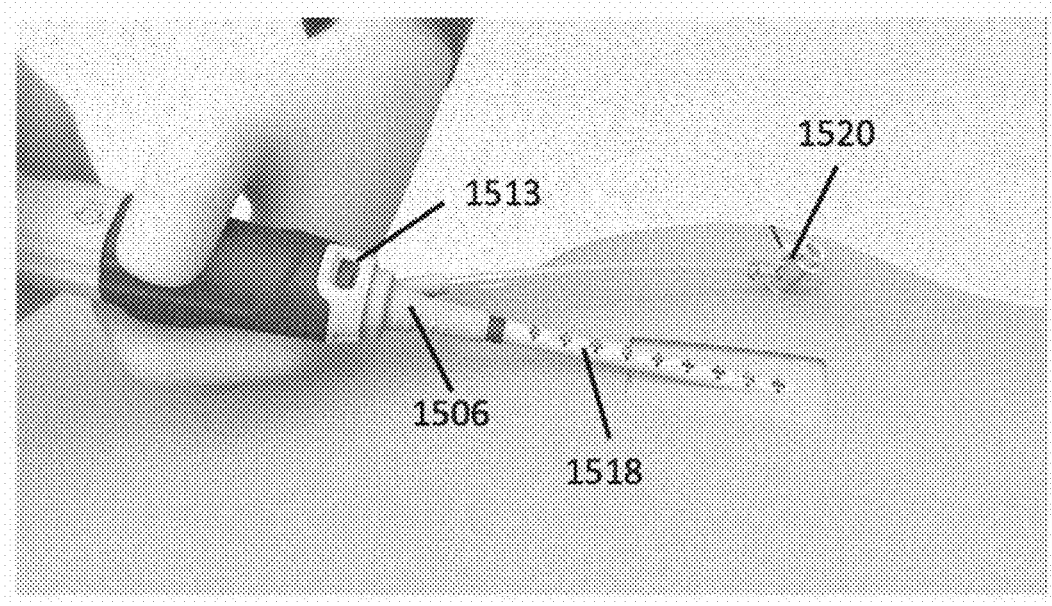
Figure 112I:
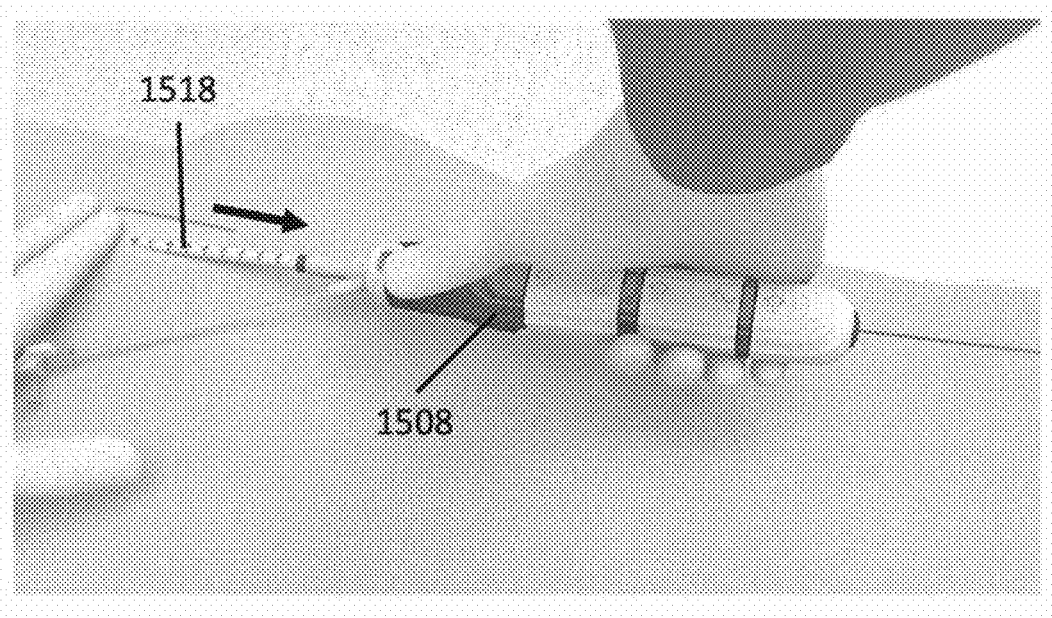
Figure 112J:
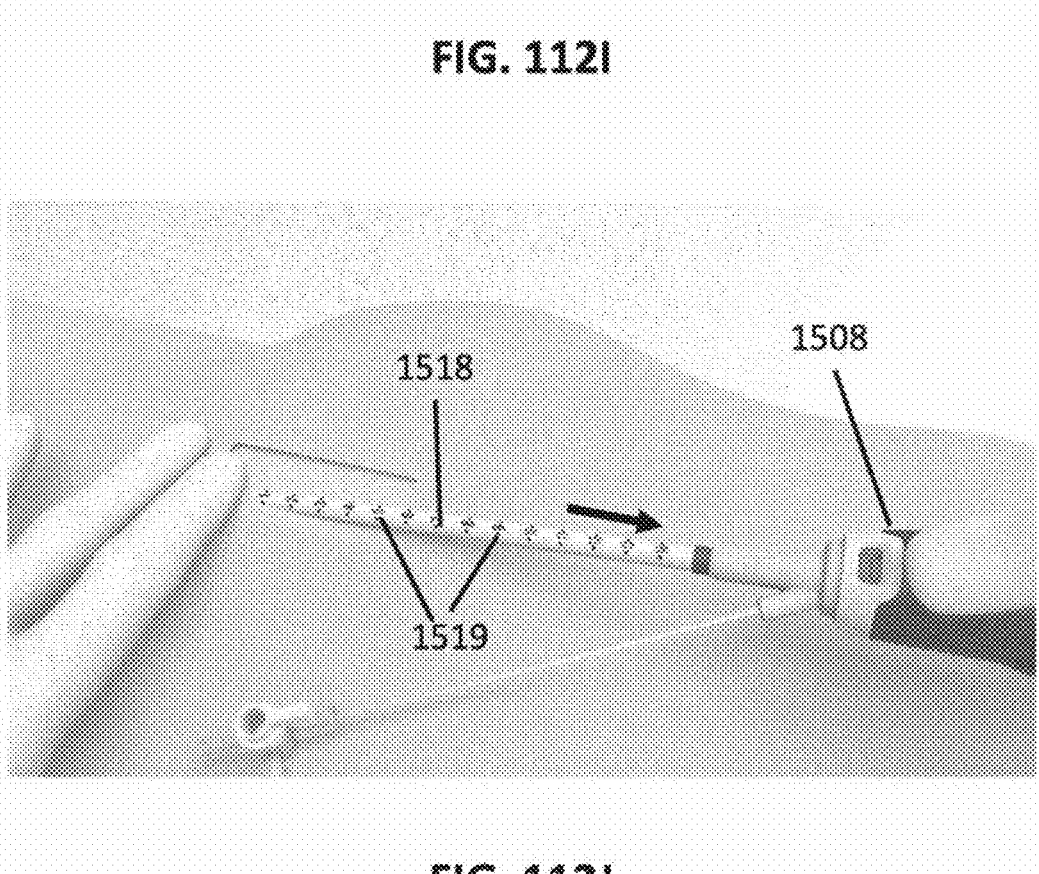
Figure 112K:
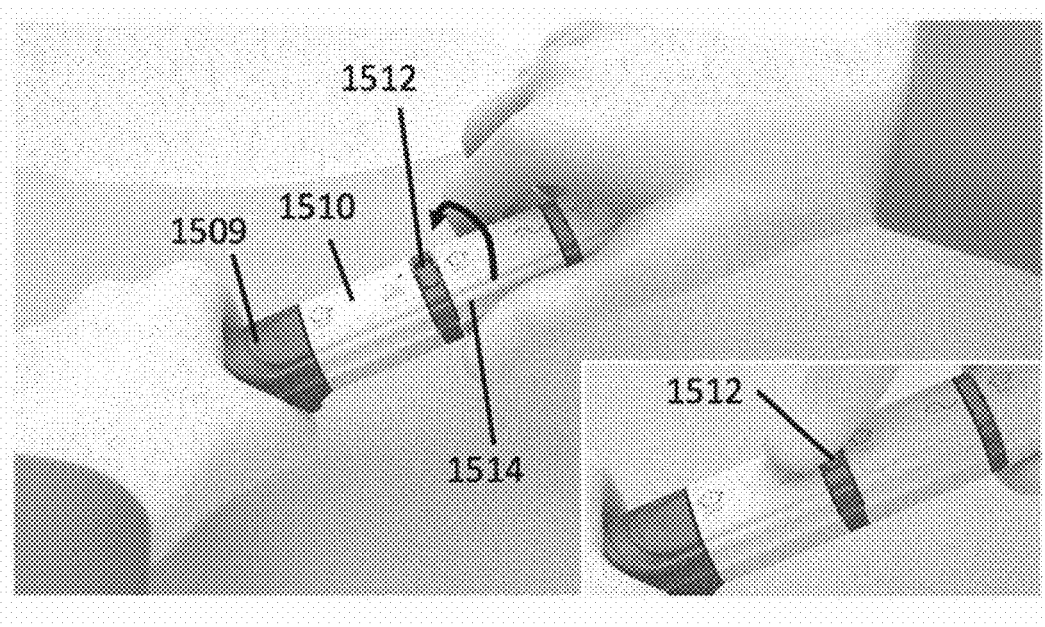
Figure 112L:
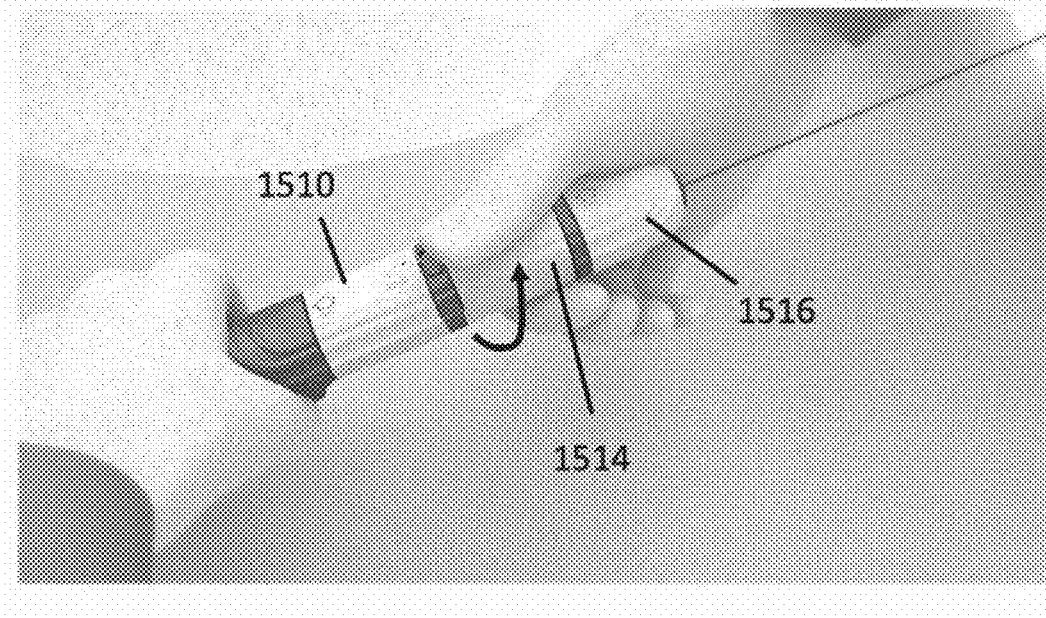
Figures 112M, 112N:
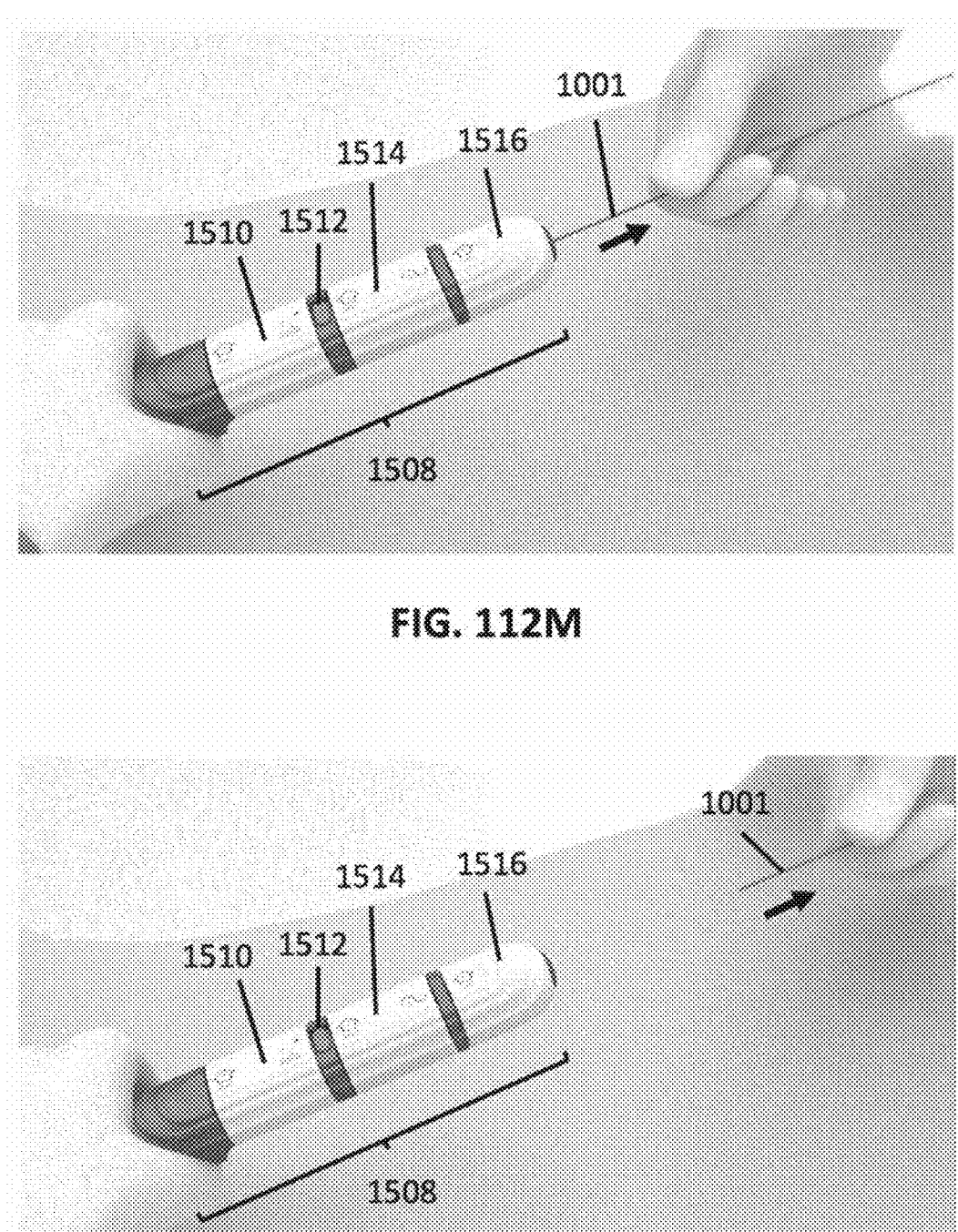
Figure 112O:
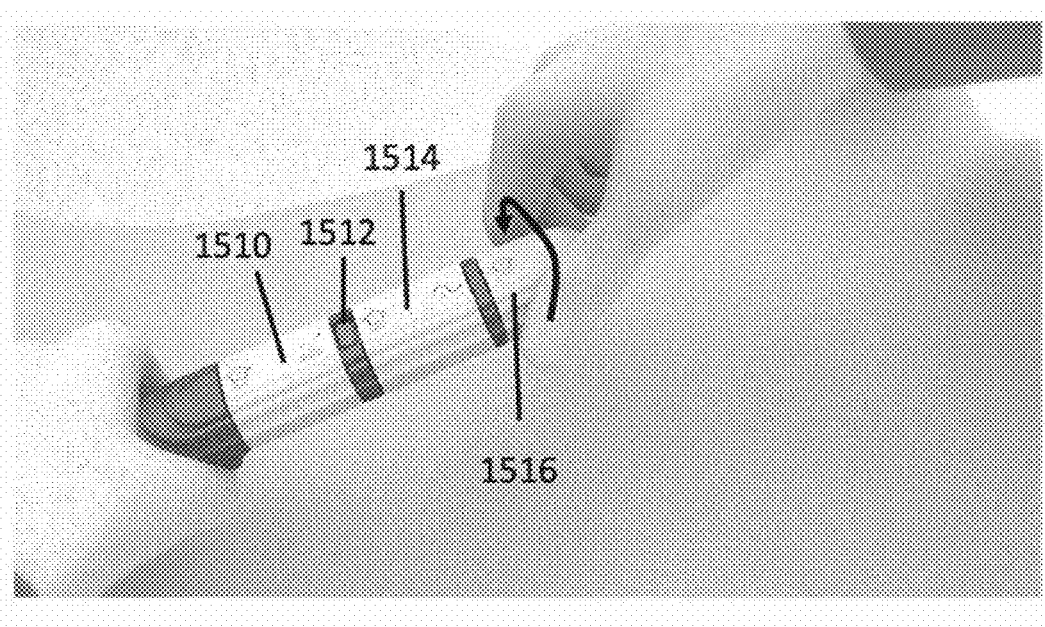
Figure 112P:
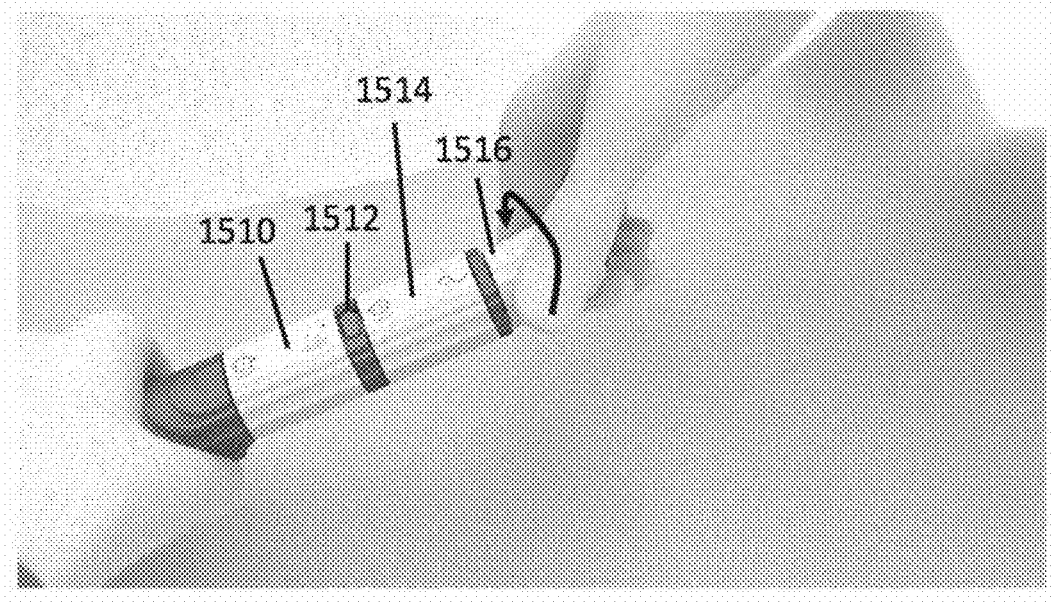
Figure 112Q:
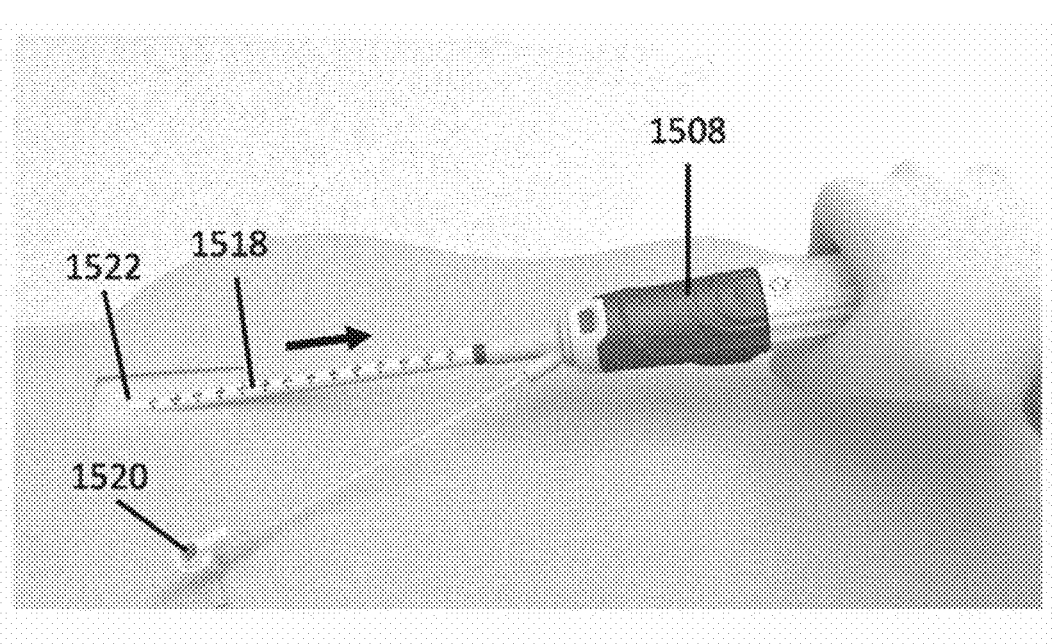
Figure 112R:
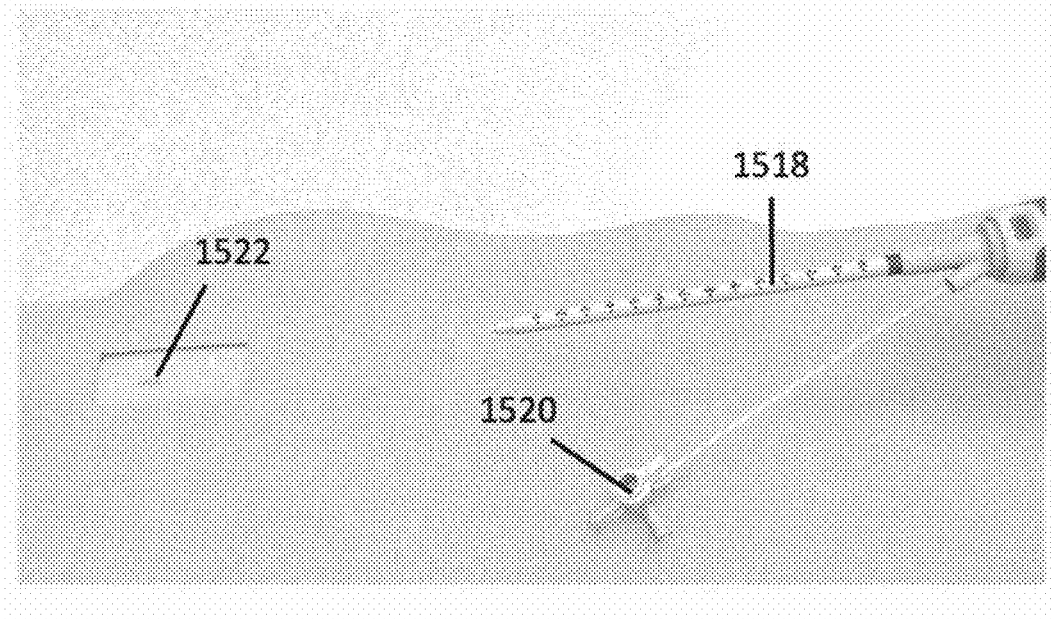

FIG. 112A through 112R illustrate views of a delivery system 1500, which includes a delivery system handle 1508, showing sequential steps in deployment of a closure device 1000, according to aspects of the present embodiments, including a scaffold 1050, a patch 1100, an external fixation 1200, and a closure pin 1300. The delivery system 1500 also includes a loading cannula 1502 and receiving funnel 1506 that is connected to an introducer sheath 1518.

Figure 112S:
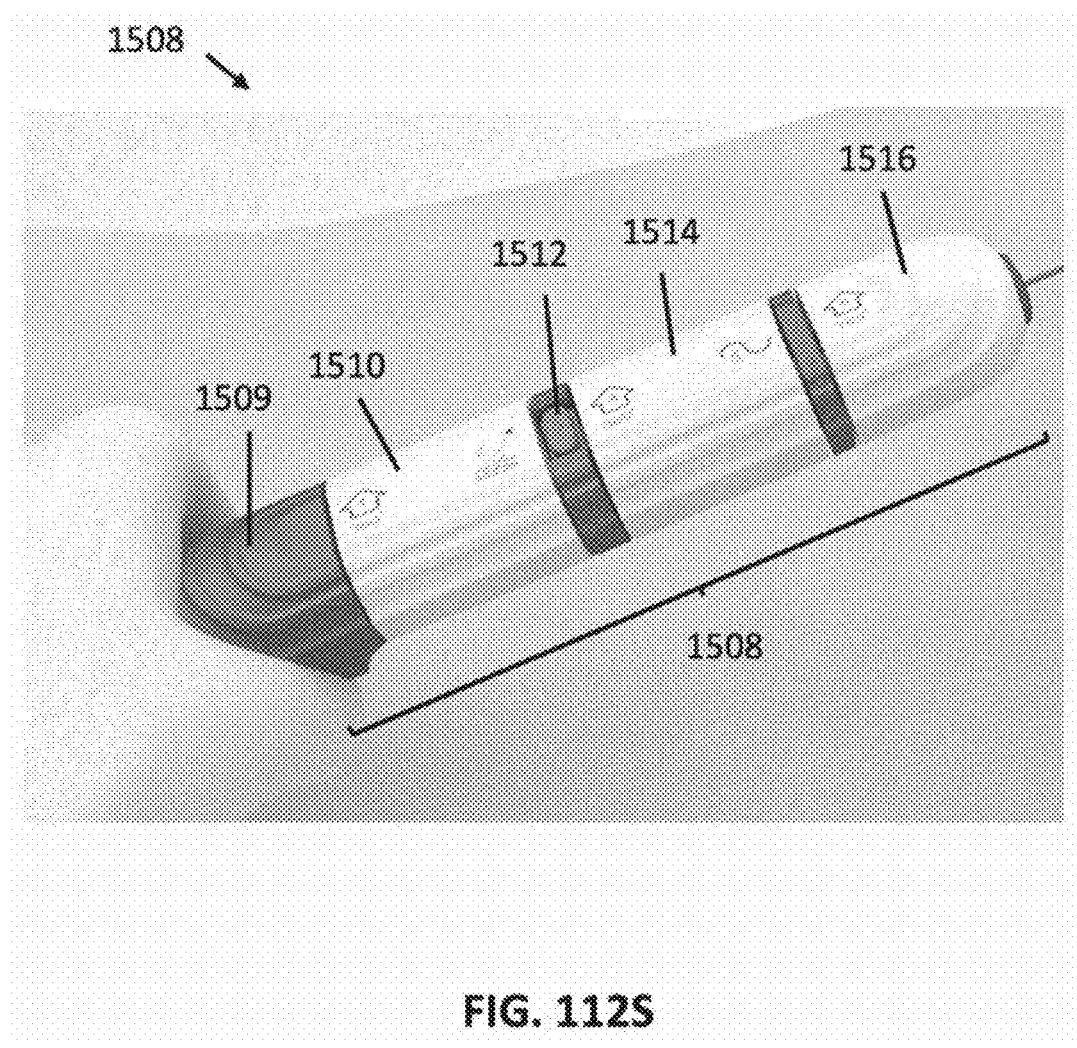
Figure 112T:
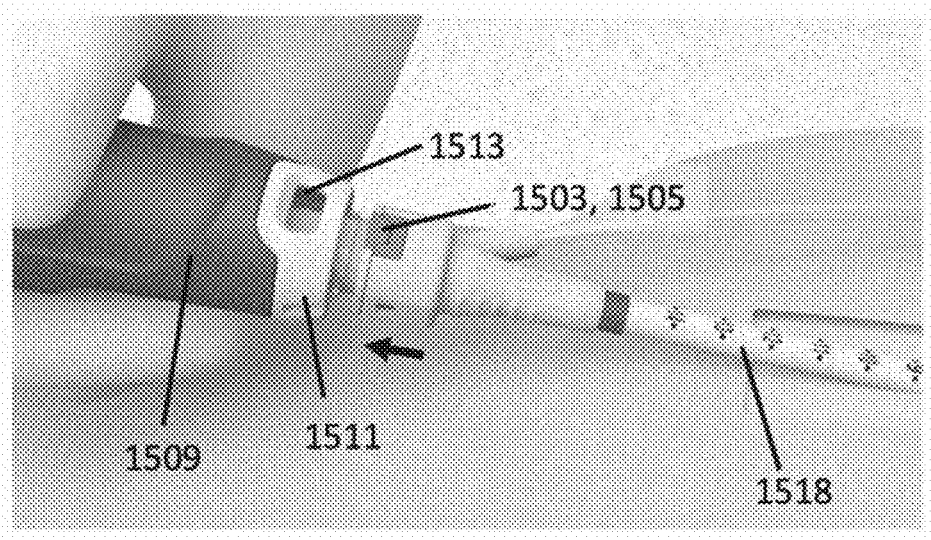
Figure 112U:
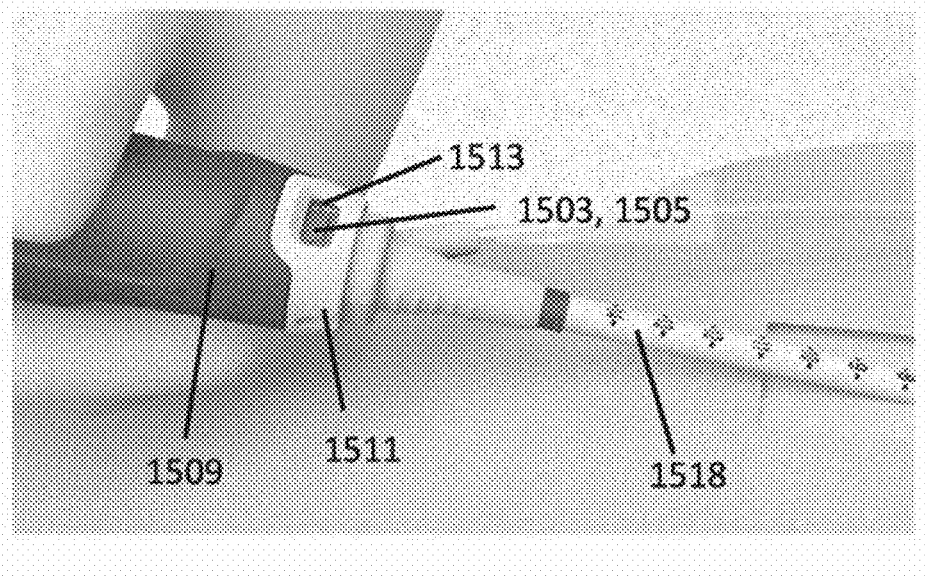

FIG. 112S illustrates a perspective view of the exterior of a delivery system handle 1508, according to aspects of the present embodiments. The handle 1508 may include a handle body 1509, a sheath cam 1510, a cam lock 1512 which may be in the form of a button, a fixation cam 1514, and a release cam 1516. Other features of the handle 1508 are illustrated in FIG. 112T and FIG. 112U, which include a front cap 1511 which includes a window 1513. The operation of the handle 1508 and window 1513 are described in further detail below.

In FIG. 112A, the introducer shaft 1518 is already inserted into a surgical opening in a subject near an aperture in a body vessel that is to be closed. The introducer shaft 1518 terminates in the receiving funnel 1506, which has a colored notch 1505 at its opening. The guidewire 1001 is inserted through the receiving funnel 1506 and the introducer shaft 1518. The loading cannula 1502 is loaded with the closure device 1000 parts (i.e., the scaffold 1050, the patch 1100, the external fixation 1200, and the closure pin 1300), and has a small colored tab 1503 at its distal edge. In the inset image, the cannula tube 1504 of the loading cannula 1502 contains the scaffold 1050 and patch 1100 visible in their stowed configurations. The external fixation 1200 and closure pin 1300 are not visible in this view. An operator or user or surgeon moves the loading cannula 1502 along the guidewire toward the receiving funnel 1506.

In FIG. 112B, the loading cannula 1502 is approaching the receiving funnel 1506.

In FIG. 112C, the loading cannula 1502 engages with the receiving funnel 1506, with the colored tab 1503 on the loading cannula 1502 inserting into the colored notch 1505 on the receiving funnel 1506. The engagement of the colored tab 1503 with the colored notch 1505 indicate to the user that the loading cannula 1502 and the receiving funnel 1506 are correctly connected together.

In FIG. 112D, a delivery system handle 1508 is inserted along a length of tube 1501, and the handle 1508 is pushed toward the loading cannula 1502 and receiving funnel 1506.

In FIG. 112E, the handle 1508 is fully inserted into position and engaged with the loading cannula 1502.

In FIG. 112F, a user rotates the sheath cam 1510 with one hand while holding the handle body 1509 with the other hand. This action causes the introducer sheath 1518 to retract proximally out of the surgical opening in the patient.

In FIG. 112G, as the user continues to rotate the sheath cam 1510, the introducer sheath 1518 continues to retract and the loading cannula 1502 moves into the handle 1508 as indicated by the arrow.

In FIG. 112H, the sheath is fully retracted, corresponding to a full 360° rotation of the sheath cam 1510. The window 1513 is an opening through which the user may see that the colored tab 1503 from the loading cannula 1502 and the colored notch 1505 from the receiving funnel 1506 (see also FIG. 112C) are visible within the window, which occurs when the sheath withdrawal step is complete. The front cap 1511, window 1513, and retraction of the colored tab 1503 and colored notch 1505 are also shown in FIG. 112T and FIG. 112U, which correspond to enlarged views of these steps in the deployment process.

In FIG. 112I, the user pulls on the handle 1508 toward the proximal direction to retract the delivery system. The portion of the sheath 1518 that is visible outside the body of the patient increases.

In FIG. 112J, the delivery system retraction is complete, corresponding to the configuration illustrated in FIG. 111F where the top surface of the patch 1100 and scaffold 1050 are in contact with the interior of the vessel wall 1401.

In FIG. 112K, in the inset image, the user presses the cam lock 1512 button. The cam lock 1512 prevents accidental rotation of the fixation cam 1514, and must be depressed by the user (i.e., by pressing the cam lock 1512 button), in order for the fixation cam 1514 to be rotated. In the main image of FIG. 112K, the user then rotates the fixation cam 1514 with one hand while grasping the handle body 1509 with the other hand. The rotation of the fixation cam 1514 pushes the external fixation 1200 toward the distal direction. This step corresponds to the scenario illustrated in FIG. 111G, as described above, where the external fixation 1200 is moving out of the sheath and toward the wall 1401 of the vessel.

In FIG. 112L, the user continues rotating the fixation cam 1514 until a full 360° is completed, at which point the external fixation 1200 is fully pushed out, corresponding to the scenario illustrated in FIG. 111H. The external fixation 1200 is at this point locked onto the neck 1060 of the scaffold 1050 on the retaining pads 1058 on the neck 1060.

In FIG. 112M, the user pulls the guidewire 1001 using one hand, moving the guidewire 1001 away from the handle 1508 and toward the distal direction, while grasping the handle 1508 with the other hand. In FIG. 112N, the guidewire 1001 is fully removed from the delivery system. The removal of the guidewire 1001 can also be seen in FIG. 111I, where the guidewire 1001 is in the process of being removed when viewed in the interior 1403 of the vessel. In FIG. 111J, the guidewire 1001 is no longer visible in the interior 1403 of the vessel.

In FIG. 112O, the user rotates the release cam 1516 with one hand while grasping the handle body 1509 with the other hand. In FIG. 112P, the user continues rotating the release cam 1516 until a full 180° turn is completed. This motion causes the closure pin 1300 to be pushed into location in the opening 1064 of the neck 1060 of the scaffold 1050 so that the opening 1064 is blocked after removal of the guidewire 1001. This motion also causes rotation of the bayonet hub 1542 (shown in FIG. 113) which results in releasing the closure device 1000 from the delivery system. This scenario also corresponds to the scenario illustrated in FIG. 111K, where the closure pin 1300 is pushed into the scaffold 1050 and the device 1000 is released from the shafts of the delivery system.

In FIG. 112Q, the user grasps the handle 1508 and pulls it away from the patient toward the proximal direction to remove the entire delivery system from the patient. The sheath 1518 is seen being pulled out of the aperture 1522. This scenario also corresponds to the scenario illustrated in FIG. 111K and FIG. 111L where the sheath 1518 is detached from the closure device 1000 and is moving away.

In FIG. 112R, the delivery system is completely removed from the body of the patient, and an aperture 1522 in the skin of the patient is visible.

Referring again to FIG. 112S, there may be several symbols and markings imprinted on the exterior surface of the handle 1508 to guide the user. On the sheath cam 1510, there is printed an arrow with a number 1 and the indication 360°. This indication instructs the user that the $1^{st}$ step is to rotate the sheath cam 1510 along the arrow direction, which is equivalent to a clockwise turn when viewing the handle from the proximal end toward the distal end, and that the rotation is for 360°. The sheath cam 1510 also has an indication with a number 2 and a dashed arrow and a symbolic representation of a heath and aperture. This indication instructs the user that the $2^{nd}$ step is to retract delivery device which results in pulling out of the introducer sheath 1518.

Referring still to FIG. 112S, the cam lock 1512 button has an indication of a number 3, which instructs the user that the $3^{rd}$ step is to press the cam lock 1512 button. The fixation cam 1514 has an indication of an arrow with a number 4 and 360°. This indication instructs the user that the $4^{th}$ step is to rotate the fixation cam 1514 in the direction of the arrow, which is equivalent to a clockwise turn when viewing the handle from the proximal end toward the distal end, and that the rotation is for 360°. The fixation cam also has an indication of a number 5 along with a wavy line, instructing the user that the $5^{th}$ step is to remove the guidewire 1001. Finally, the release cam 1516 has an arrow indicated with a number 6 and a number 180°. This indication instructs the user that the $6^{th}$ step is to rotate the release cam 1516 in the direction of the arrow, which is equivalent to a clockwise turn when viewing the handle from the proximal end toward the distal end, and that the rotation is for 180°.

Figure 113:
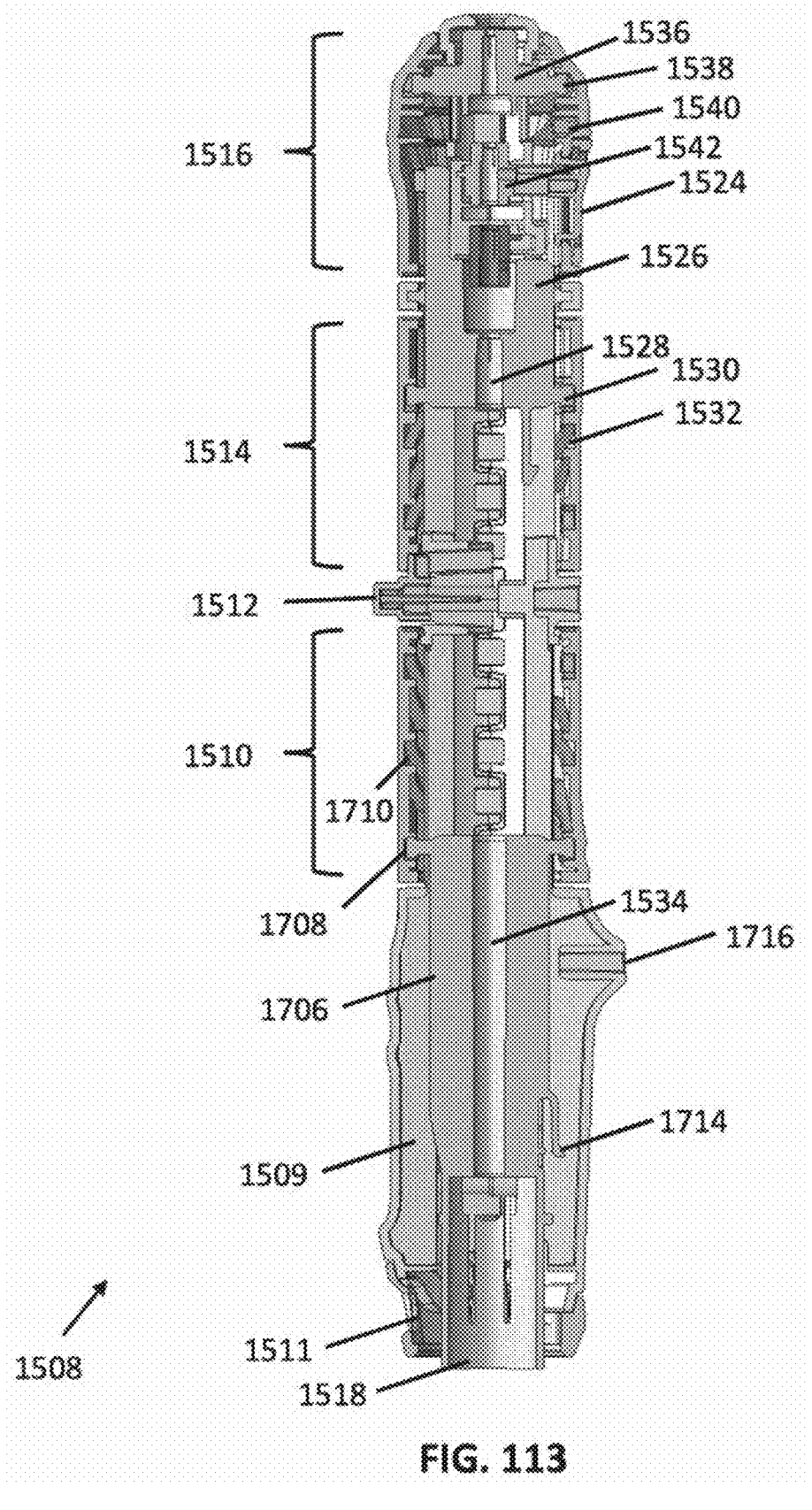
FIG. 113 illustrates a cut-away side view of the interior of a delivery system handle, according to aspects of the present embodiments.

FIG. 113 illustrates a cut-away side view of the interior of a delivery system handle 1508, according to aspects of the present embodiments.

Figure 114:
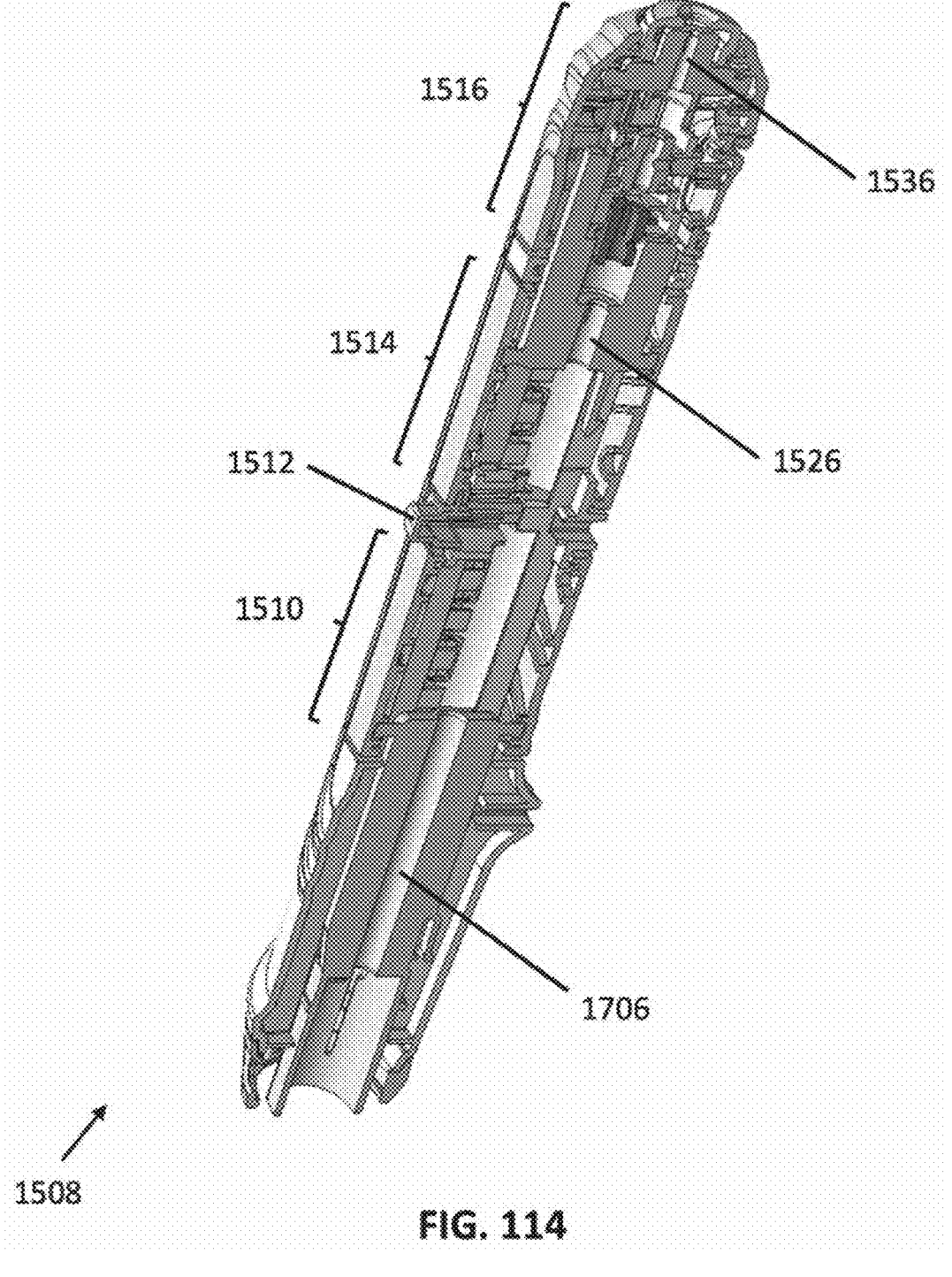
FIG. 114 illustrates a cut-away perspective view of the interior of a delivery system handle, according to aspects of the present embodiments.

FIG. 114 illustrates a cut-away perspective view of the interior of a delivery system handle 1508, according to aspects of the present embodiments.

Figure 115:
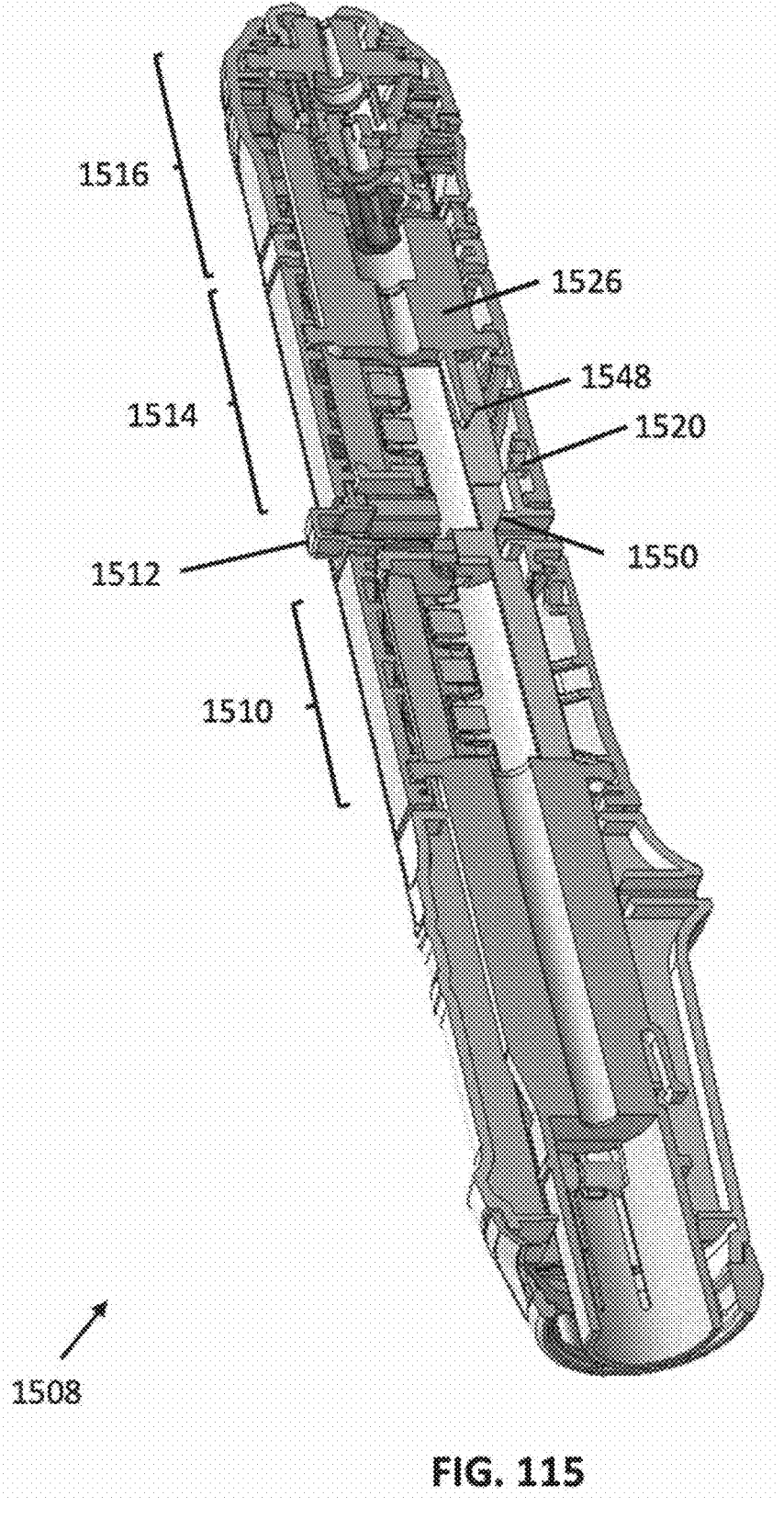

FIG. 115 illustrates another cut-away perspective view of the interior of a delivery system handle 1508, according to aspects of the present embodiments.

FIG. 116 illustrates a method 1600 of sealing an aperture, according to aspects of the present embodiments. At step 1602, the method 1600 may include preliminary implant loading steps. For example, preliminary implant loading steps may include one or more of the following steps: i) disposing the guidewire 1001 into and through the delivery system, the implant, the cannula assembly, and handle, ii) disposing the guidewire 1001 into the wound and/or vessel aperture, iii) disposing the delivery system subcutaneously and into the vessel through the aperture using the guidewire 1001 and using an introducer sheath 1518, and/or iv) loading the implant or closure device 1000 into the cannula assembly, as shown in FIGS. 112A-112C. The handle 1508 may include a handle body 1509 that includes two halves which include a handle body top and a handle body bottom configured to be snapped together, and further held together by a front cap 1511 at the distal end of the handle 1508. At step 1604, the method 1600 may include pushing the handle 1508 distally, forming the handle assembly. By pushing the handle distally, the cannula assembly is pushed distally through the delivery shaft 1408 and into the vessel. At step 1606, the method 1600 may include rotating a sheath cam 1510 (shown in FIG. 113) through an angle of 360 degrees. The sheath cam 1510 may include two semi-cylindrical halves (i.e., a sheath cam top and a sheath cam bottom that are configured to be snapped or held together to form a main chassis of the handle 1508). Step 1606 is illustrated in FIGS. 112F-112H. The direction of rotation of the sheath cam 1510 is clockwise when viewed from the proximal side looking distally. The rotation of the sheath cam 1510 causes retraction (i.e., movement toward the proximal direction) of the introducer sheath 1518, thereby allowing the patch 1100 and scaffold 1050 to expand within the vessel, as shown in FIGS. 111A-111D. The external fixation 1200, however, remains within the delivery shaft as shown in FIGS. 111B-111D.

Referring to FIGS. 111-116, the handle 1508 may include a sheath carriage 1706 coupled to (or monolithic with) the proximal end of the introducer shaft 1518. The sheath carriage 1706 may include a one or more external male threads 1708 which interface with internal female threads 1710 disposed within an interior circumference of the sheath cam 1510. As the sheath cam 1510 is rotated, the one or more external male threads 1708 interface with the internal threads 1710 of the sheath cam 1510, thereby causing the introducer shaft 1518 to retract proximally. Once the introducer shaft 1518 has fully retracted to a proximal-most location, a first prong 1714 interfaces with a first catch 1716, thereby preventing further rotation of the sheath cam 1510.

At step 1608, the method 1600 may include pulling the entire device proximally such that the patch 1100 (with the help of the scaffold 1050) is secured against an inner wall of the vessel 1401, the inner wall surrounding and/or adjacent to the aperture in the vessel 1401. At step 1610, markings 1519 (shown in FIG. 112J) on the exterior of the introducer sheath 1518 may be used to gauge or assess how far the device should be pulled proximally in order to secure the patch 1100 against the inner wall of the vessel 1401. For example, when one of the numerical markings (for example, the line next to the "1" mark) on the introducer sheath 1518 line up with the edge of the skin (for example, at the aperture in the skin), then the device is correctly positioned in order for the patch to be secured against the inner wall of the vessel 1401, as shown in FIGS. 111E-111G (internal illustrations), as well as in FIGS. 112I and 112J (external views). Steps 1608 (pulling the device proximally) and 1610 (using the external markings to assess correct positioning of the patch) may therefore be performed simultaneously, in some embodiments. During steps 1608 and 1610, while the device is being pulled proximally, the external fixation 1200 is pulled back through the aperture of the vessel 1401 such that it is repositioned outside the vessel, as shown in FIGS. 111E-111G, which are in contrast to the position of FIGS. 111C and 111D, in which the external fixation 1200 is positioned within the vessel.

Referring still to FIGS. 112-116, at step 1612, the method may include pressing a release button (i.e., cam lock 1512) shown in FIG. 113. The cam lock 1512 (shown in FIGS. 113 and 112K) may be used to allow a fixation cam 1514 to be rotated. The fixation cam 1514 may be located proximally of the cam lock 1512 (which itself may be disposed proximally from the sheath cam 1510). Whereas the sheath cam 1510 may be used to retract the introducer shaft 1518 in a proximal direction, the fixation cam 1514 may be used to push the fixation cam 1404 distally via an internal rod, linkage, or coupling (not shown) disposed through a large bore 1534 disposed through the center of the sheath cam 1510 (and configured to translate distally therethrough). At step 1614, the method 1600 may include rotating the fixation cam 1514 through an angle of 360 degrees (i.e., in a clockwise direction when viewed from the proximal side looking distally) to push the fixation shaft 1404 (and external fixation 1200 coupled thereto) in a distal direction. The fixation cam 1514 is twistedly coupled to a fixation hub 1526 via one or more male threads 1530 on the fixation hub 1526 and internal female threads 1532 disposed within an interior circumference of the fixation cam. Twisting the fixation cam 1514 advances the external fixation 1200, which is coupled thereto by a second internal rod, linkage, or coupling (not shown) disposed within a medium bore 1528 at the center of the fixation hub 1526. By pushing the external fixation 1200 distally, fixation 1200 may slide along the neck 1060 of the scaffold 1050 in order to interface with corresponding features on the scaffold neck 1060 such that the implant is secured at the aperture (i.e., wound and/or puncture) location, as described herein, and as shown in FIG. 111H. When the implant is securely implanted in its final location, the patch 1100 and scaffold 1050 are pressed up against the inner wall of the vessel, the scaffold neck 1060 extends through the vessel aperture, and the external fixation 1200 presses against the external wall of the vessel 1401 and securely holds the closure device in place, as shown in FIG. 111H. As illustrated in FIG. 115, once the fixation hub 1526 has translated all the way forward (i.e., to a distal-most position) within the handle 1508, a second prong engages

1548 with a second catch 1550 (both shown in FIG. 115), thereby prohibiting further rotation of the fixation cam 1514.

Still referring to FIGS. 112-116, at step 1616, the method 1600 may include removing the guidewire 1001 from the vessel 1401, aperture, and device, by pulling the guidewire 1001 proximally from the proximal end of the handle 1508, as shown in FIGS. 111H-111J, as well as in FIGS. 112M and 112N. At step 1618, the method 1600 may include rotating the release cam 1516 through an angle of 180 degrees to disengage the delivery system from the implant. When the release cam 1516 is rotated 180 degrees clockwise, a push hub 1536 is distally advanced via a third set of male threads 1538 and female threads 1540, thereby pushing the pin 1300 into the interior lumen 1064 of the scaffold neck 1060, in order to minimize leakage through the scaffold neck 1060 once the guidewire 1001 is removed. In connection with the step 1618, a bayonet hub 1542 is rotated (i.e., via rotation of the release cam 1516), thereby causing the release of the implant from the distal tip of the delivery system. At step 1620, the method may include pulling the delivery system away from the implant and patient.

As shown in FIG. 114, each of the sheath carriage 1706, the fixation hub 1526, and the push hub 1536 translate axially (for example, proximally and/or distally) within the handle 1508 when the respective sheath cam 1510, fixation cam 1514, and release cam 1516 are rotated.

FIG. 115 shows another view of the interior of the delivery system handle 1508. The main components as above are also indicated.

Although certain figures and embodiments relate to use of systems and devices for closure of a perforation associated with vascular surgery, one of ordinary skill in the art will appreciate that components of a provided device are not size dependent (i.e., are scalable) and are therefore useful for closure of any perforation in a lumen of a mammal.

Although the present invention has been described with reference to particular examples and exemplary embodiments, it should be understood that the foregoing description is in no manner limiting. Moreover, the features described herein may be used in any combination.

What is claimed is:

1. An implantable device for sealing an aperture in a wall of a body vessel, the implantable device comprising:

an external fixation to be disposed on the outside of the vessel wall;

a scaffold to be disposed on the inside of the vessel wall and interfacing with the external fixation, with at least a portion of the scaffold to be disposed through an aperture in the vessel wall, the scaffold comprising:

a base plate;

a neck extending externally at an angle from the base plate, the neck comprising at least one lumen disposed therethrough; and at least two retaining tabs, wherein the at least two retaining tabs are disposed circumferentially around an exterior of the scaffold neck and extend radially away from the scaffold neck, and wherein the at least two retaining tabs interface with a collar of the external fixation, thereby causing the external fixation to be coupled to the scaffold, wherein the external fixation further comprises a tab disposed at an angle from the collar, the tab comprising a protrusion;

a patch configured to be disposed on the inside of the vessel wall and sandwiched between the external fixation and the scaffold, with the patch capable of substantially covering the full area of the aperture, thereby sealing the aperture; and a closure pin disposed within the scaffold neck for sealing the at least one lumen after a guidewire is removed from the guidewire lumen; the closure pin comprising:

a cylindrical body;

a tip disposed at the distal end of the cylindrical body that comprises at least one of an angled tip and a stepped tapered tip; and a substantially cylindrical head disposed at the proximal end of the cylindrical body and comprising a rectangular cutout, the rectangular cutout interfacing with the protrusion on the external fixation, wherein distally pushing the closure pin into the scaffold neck causes the closure pin to seal the at least one lumen.

2. The device of claim 1, wherein the external fixation comprises:

the collar;

a base ring;

an anterior rib connecting the collar and the base ring; and a posterior post connecting the collar and the base ring.

3. The device of claim 1, wherein the scaffold comprises a threaded portion at the base of the neck, the threads of the threaded portion interacting with the opening of the patch to hold the patch against the upper surface of the base plate of the scaffold.

4. The device of claim 1, wherein the closure pin comprises at least one of a pair of first and second distally extending arms, a rupture portion, an offset bore, an angled pin, a slidable rod, and an L-shaped closure pin.

5. The device of claim 1, wherein the scaffold neck comprises at least one of an internal taper, a gradual tapered portion, a ramp portion, a sleeve portion, an angled surface, and a partial bore.

6. The device of claim 1, wherein the aperture is located in a blood vessel, and a longitudinal axis of the patch is to be aligned with a longitudinal axis of the blood vessel when the device is in a sealing position.

7. The device of claim 1, wherein a longitudinal dimension of the patch is within a range of about 6 to about 29 mm and a lateral dimension of the patch is within a range of about 4 mm to about 22 mm.

8. The device of claim 1, wherein an average thickness of the patch is within a range of 100 μm to 500 μm.

9. The device of claim 1, wherein the patch comprises:

a base layer having a thickness within a range of 190-220 μm; and an electrospun layer having a thickness within a range of 20-80 μm, wherein a total thickness of the patch is within a range of 210-300 μm.

10. The device of claim 1, wherein the patch comprises an opening disposed at the center of the patch, the scaffold neck passing through the opening in the patch.

11. An implantable device for sealing an aperture in a wall of a body vessel, the implantable device comprising:

an external fixation to be disposed on the outside of the vessel wall when in a sealing position;

a scaffold to be disposed on the inside of the vessel wall when in a sealing position and interfacing with the external fixation, with at least a portion of the scaffold to be disposed through an aperture in the vessel wall, the scaffold comprising;

a base plate;

a neck extending externally at an angle from the base plate, the neck comprising at least one lumen disposed therethrough; and at least two retaining tabs, each retaining tab comprising:

a first protrusion;

a notch;

a flat portion; and a second protrusion, wherein the first protrusion, the notch, the flat portion, and the second protrusion are arranged longitudinally within the retaining tab along an axial direction of the scaffold neck, wherein the first protrusion and the second protrusion extend out radially from the surface of the scaffold neck, wherein the first protrusion extends further radially outwardly than the second protrusion, wherein the notch is disposed at a smaller radius than the second protrusion, wherein the at least two retaining tabs are disposed circumferentially around an exterior of the scaffold neck and extend radially away from the scaffold neck, and wherein the at least two retaining tabs interface with a collar of the external fixation, thereby causing the external fixation to be coupled to the scaffold; and a patch to be disposed on the inside of the vessel wall and sandwiched between the external fixation and the scaffold when in a sealing position, with the patch capable of substantially covering the full area of the aperture, thereby sealing the aperture.

* * * * *